US007626001B2

(12) United States Patent
Reed et al.

(10) Patent No.: US 7,626,001 B2
(45) Date of Patent: Dec. 1, 2009

(54) CARD DOMAIN CONTAINING POLYPEPTIDES, ENCODING NUCLEIC ACIDS, AND METHODS OF USE

(75) Inventors: John C. Reed, Rancho Santa Fe, CA (US); Frederick F. Pio, Vancouver (CA); Adam Godzik, San Diego, CA (US); Christian Stehlik, San Diego, CA (US); Jason S. Damiano, La Jolla, CA (US); Sug Hyung Lee, San Diego, CA (US); Vasco A. Oliveira, San Diego, CA (US); Hideki Hayashi, Nagasaki (JP); Kryzysztof Pawlowski, Malmo (SE)

(73) Assignee: Burnham Institute for Medical Research, La Jolla, CA (US)

( * ) Notice: Subject to any disclaimer, the term of this patent is extended or adjusted under 35 U.S.C. 154(b) by 0 days.

(21) Appl. No.: 11/728,892

(22) Filed: Mar. 26, 2007

(65) Prior Publication Data
US 2007/0184480 A1 Aug. 9, 2007

Related U.S. Application Data

(63) Continuation of application No. 09/864,921, filed on May 23, 2001, now Pat. No. 7,196,182.

(60) Provisional application No. 60/275,980, filed on Mar. 14, 2001, provisional application No. 60/367,337, filed on Oct. 10, 2000, provisional application No. 60/325,756, filed on May 24, 2000.

(51) Int. Cl.
*C07K 14/00* (2006.01)
(52) U.S. Cl. .................................................... 530/350
(58) Field of Classification Search ........................ None
See application file for complete search history.

(56) References Cited

U.S. PATENT DOCUMENTS

| 5,223,409 | A  |   | 6/1993 | Ladner et al. |
| 6,858,391 | B2 |   | 2/2005 | Nunez et al. |
| 7,083,944 | B1 | * | 8/2006 | Bertin et al. ............... 435/69.1 |

FOREIGN PATENT DOCUMENTS

| WO | WO 96/12016 | 4/1996 |
| WO | WO 99/40102 | 8/1999 |
| WO | WO 01/00826 | 1/2001 |
| WO | WO 01/18042 | 3/2001 |
| WO | WO 01/30971 | 5/2001 |
| WO | WO 01/66690 | 9/2001 |
| WO | WO 01/72822 | 10/2001 |

OTHER PUBLICATIONS

Rost et al, "Enzyme function less conserved than anticipated", Journal of Molecular Biology (2002) 318:595-608.*
Dujon et al, Trends in Genetics (1996) 12(7):263-270.*
Ahmad et al., "CRADD, a novel human apoptotic adaptor molecule for caspase-2, and FasL/tumor necrosis factor receptor-interacting protein RIP," *Cancer Res.* 57:615-619 (1997).
Altschul et al., "Gapped Blast and PSI-Blast: a new generation of protein database search programs," *Nucleic Acids Res.*, 25:3389-3402 (1997).
Bertin et al., "Human CARD4 Protein Is a Novel CED=4/Apaf-1 Cell Death Family Member That Activates Nf-kB," *Journal of Biological Chemistry* 274(19):12955-12958 (1999).
Bertin et al., "Human CARD4 Protein is a Novel CEO-4/Apaf-1 Cell Death Family Member that Activates Nf-kB*," *J. Biol. Chem.* 274:12955-12958 (1999).
Damiano et al., "CLAN, a Novel Human CED-4-like Gene," *Genomics* 75:77-83 (2001).
DiDonato et al., "A cytokine-responsive IkB kinase that activates the transcription factor NF-kB," *Nature* 388:548-554 (1997).
Dujon, B., "The yeast genome project: what did we learn?" *Trends Genet.* 12(7):263-270 (1996).
Ellerby et al., "Anti-cancer activity of targeted pro-apoptotic peptides," *Nature Med.* 5:1032-1038 (1999).
Enkhbayar et al., "Structural principles of leucine-rich repeat (LRR) proteins," *Proteins* 54:394-403 (2003).
Fletcher et al., "A synthetic inhibitor of interleukin-1 beta converting enzyme prevents endotoxin-induced interleukin-1 beta production in vitro and in vivo," *J. Interferon Cytokine Res.*, 15:243-248 (1995).
Geddes et al., "Human CARD12 Is a Novel CED4/Apaf-1 Family Member That Induces Apoptosis," *Biochemical and Biophysical Research Communications* 284:77-82 (2001).
Gregoriadis, *Liposome Technology*, vols. I to III, 2nd ed., CRC Press, Boca Raton, FL (1993). (Table of contents only).
Hofmann and Bucher, "The CARD domain: a new apoptotic signalling motif," *Trends Biochem. Sci.*, 22:155-156 (1997).
Holinger et al., "Bak BH3 Peptides Antagonize Bcl-x.sub.L Function and Induce Apoptosis through Cytochrome c-independent Activation of Caspases," *J. Biol. Chem.* 274:13298-13304 (1999).
Inohara et al., "Nod1, an Apaf-1-like Activator of Caspase-9 and Nuclear Factor-kB," *J. Biol. Chem.* 274:14560-14567 (1999).
Kobe and Deisenhofer, "Proteins with leucine-rich repeats," *Current Opinion in Structural Biology*, 3(5):409-416 (1995).
Koonin and Aravind, "The NACHT family—a new group of predicted NTPases implicated in apoptosis and MHC transcription activation," *Trends Biochem. Sci.*, 25(5):223-224 (2000).
Li et al., "Cytochrome c and dATP-Dependent Formation of Apaf-I/Caspase-9 Complex Initiate an Apoptotic Protease Cascase," *Cell* 91:479-489 (1997).
Neufeld and Rubin, "The Drosophila peanut Gene Is Required for Cytokinesis and Encodes a Protein Similar to Yeast Putative Bud Neck Filament Proteins," *Cell* 77:371-379 (1994).
Ogura et al., "Nod2, a Nodl/Apaf-1 family member that is restricted to monocytes and activates Nf-.kappa.B", *J. of Biol. Chem.* 276 (7):4812-4818 (2001).

(Continued)

*Primary Examiner*—Kenneth R. Horlick
*Assistant Examiner*—Mark Staples
(74) *Attorney, Agent, or Firm*—McDermott Will & Emery LLP

(57) ABSTRACT

The invention provides caspase recruitment domain (CARD)-containing polypeptides, CARD, NB-ARC, ANGIO-R, LRR and SAM domains therefrom, as well as encoding nucleic acid molecules and specific antibodies. The invention also provides related screening, diagnostic and therapeutic methods.

4 Claims, 6 Drawing Sheets

OTHER PUBLICATIONS

Poyet et al., "Identification of Ipaf, a Human Caspase-1-activating Protein Related to Apaf-1," *Journal of Biological Chemistry* 276:28309-28313 (2001).

Rano et al., "A combinatorial approach for determining protease specificities: application to interleukin-1 beta converting enzyme (ICE)," *Chem. Biol.*, 4:149-155 (1997).

Rodriguez et al., "Dark is a Drosophila homologue of Apaf-1/CEO-4 and functions in an evolutionarily conserved death pathway," *Nature Cell Biol.* 1:272-279 (1999).

Rost et al, "Enzyme function less conserved than anticipated", *Journal of Molecular Biology*, 318:595-608 (2002).

Rothe et al., "The TNFR2-TRAF Signaling Complex Contains Two Novel Proteins Related to Baculoviral Inhibitor of Apoptosis Proteins," *Cell* 83:1243-1252 (1995).

Rotonda et al., "The three-dimensional structure of apopain/CPP32, a key mediator of apoptosis," *Nature Struc. Biol.* 3:619-625 (1996).

Rychlewski et al., "Comparison of sequence profiles. Strategies for structural predictions using sequence information," *Protein Science* 9:232-241 (2000).

Saleh et al., "Cytochrome c and dATP-mediated Oligomerization of Apaf-1 Is a Prerequisite for Procaspase-9 Activation," *J. Biol. Chem.* 274:17941-17945 (1999).

Schwarze et al., "In Vivo Protein Transduction: Delivery of a Biologically Active Protein into the Mouse," *Science* 285:1569-1572 (1999).

Stapleton et al., "The crystal structure of an Eph receptor SAM domain reveals a mechanism for modular dimerization," *Nature Structural Biology* 6(1):44-49 (1999).

Tatusova and Madden, "Blast 2 Sequences, a new tool for comparing protein and nucleotide sequences," *FEMS Microbiol Lett.* 174:247-250 (1999).

Thome et al., "Identification of CARDIAK, a RIP-like kinase that associates with caspase-1," *Curr. Biol.* 8:885-888 (1998).

Thornberry and Molineaux, "Interleukin-1 beta converting enzyme: a novel cysteine protease required for IL-1 beta production and implicated in programmed cell death," *Protein Sci.*, 4:3-12 (1995).

Thornberry et al., "A novel heterodimeric cysteine protease is required for interleukin-1 beta processing in monocytes," *Nature*, 356:768-774 (1992).

Thornberry, Nancy A., "Caspases: key mediators of apoptosis," *Chemistry and Biology* 5:R97-R103 (1998).

Tschopp et al., "Inhibition of Fas death signals by FLIPs," *Curr. Op. Immunol.* 10:552-558 (1998).

van der Biezen and Jones, "The NB-ARC domain: a novel signalling motif shared by plant resistance gene products and regulators of cell death in animals," *Curr. Biol.* 8:R226-R227 (1998).

Vocero-Akbani et al., "Killing HIV-infected cells by transduction with an HIV protease-activated caspase-3 protein," *Nature Med.* 5:29-33 (1999).

Willis et al., "Bc110 is Involved in t(1;14)(p22;q32) of MALT B Cell Lymphoma and Mutated in Multiple Tumor Types," *Cell* 96:35-45 (1999).

Yuan and Horvitz, "The Caenorhabditis elegans cell death gene ced-4 encodes a novel protein and is expressed during the period of extensive programmed cell death," *Development* 116:309-320 (1992).

Zou et al., "An APAF-1 Cytochrome c Multimeric Complex is a Functional Apoptosome that Activates Procaspase-9," *J. Biol. Chem.* 274:11549-11556 (1999).

Zou et al., "Apaf-1, a Human Protein Homologous to C. elegans CED-4, Participates in Cytochrome c-Dependent Activation of Caspase-3," *Cell* 90:405-413 (1997).

Database Accession No. AC007728, Database EMBL, "*Homo sapiens* chromosome 16 clone RP11-327f22, complete sequence" (Jun. 7, 1999).

Database Accession No. AC010968, Database EMBL, "*Homo sapiens* chromosome 2 clone RP11-9302, Working Draft Sequence, 11 unordered pieces" (Sep. 29, 1999).

Database Accession No. AC016492, Database EMBL, "*Homo sapiens* chromosome 4 clone RP11-94C22 map 4, Low-Pass Sequence Sampling" (Dec. 10, 1999).

Database Accession No. AC025758, Database EMBL, "*Homo sapiens* chromosome 5 clone CTD-2235A13, Working Draft Sequence, 16 ordered pieces" (Mar. 16, 2000).

Database Accession No. AC026732, Database EMBL, "*Homo sapiens* chromosome 5 clone CTD-2303L1, complete sequence" (Mar. 24, 2000).

Database Accession No. AQ534686, Database EMBL, "*Homo sapiens* genomic clone RPCI-11-384F21, genomic survey sequence," (May 18, 1999).

Genbank Accession No. AQ309404 (Dec. 22, 1998).

* cited by examiner

```
CLANA   MNFIKDNSRALIQRMGMTVIKQITDDLFVNNVLNREEVNIICCEKVEQDAARGIIHNILKKGSES
CLANB   MNFIKDNSRALIQRMGMTVIKQITDDLFVNNVLNREEVNIICCEKVEQDAARGIIHNILKKGSES
CLANG   MNFIKDNSRALIQRMGMTVIKQITDDLFVNNVLNREEVNIICCEKVEQDAARGIIHNILKKGSES
CLAND   MNFIKDNSRALIQRMGMTVIKQITDDLFVNNVLNREEVNIICCEKVEQDAARGIIHNILKKGSES

CLANA   CNLFLKSLKENNYPLFQDINGQSLPHQFSEGDLDDLAQDLKDLYHTPSFLNEYPLGEDIDIIENL
CLANB   CNLFLKSLKENNYPLFQDINGQ-------------------------------------------
CLANG   CNLFLKSLKENNYPLFQDINGQSLPHQFSEGDLDDLAQDLKDLYHTPSFLNEYPLGEDIDIIENL
CLAND   CNLFLKSLKENNYPLFQDINGQSLPA

CLANA   KSTFTEPVLWRKDQHHHRVEQLTLNGLLQALQSPCIIEGESGKGKSTLLQRIAMLWGSGKCKALT
CLANB   ------------------------------------------------------------------
CLANG   KSTFTEPVLWRKDQHHHRVEQLTLVL

CLANA   KFKFVFPLRLSRAQGGLFETLCDQLLDIFGTIRKQTFMAMLLKLRQRVLFLLDGYNEFKPQNCPE
CLANB   ------------------------------------------------------------------

CLANA   IEALIKENHRFKNMVIVTTTTECLRHIRQPGALTAEVGDMTEDSAQALIREVLIKELAEGLLLQI
CLANB   ------------------------------------------------------------------

CLANA   QKSRCLRNLMKTPLFVVITCAIQMGESEFHSHTQTTLPHTFYDLLIQKNKHKHKGVAASDPIRSL
CLANB   ------------------------------------------------------------------

CLANA   DHRGDLALEGVFSHKPDFELQDVSSVNEDVLLTTGLLCKYTAQRFKPKYKFPHKSFQEYTAGRRL
CLANB   ------------------------------------------------------------------

CLANA   SSLLTSHEPEEVTKGNGYLQKMVSISDITSTYSSLLRYTCGSSVEATRAVMKHLAAVYQHGCLLG
CLANB   ------------------------------------------------------------------

CLANA   LSIAKRPLWRQESLQSVKNTTEQEILKAININSFVECGIHLYQESTSKSALSQEFEAFFQGKSLY
CLANB   ------------------------------------------------------------------

CLANA   INSGNIPDYLFDFPEHLPNCASALDFIKLDFYGGAMASWEKAAEDTGGIHMEEAPETYIPSRAVS
CLANB   ------------------------------------------------------------------

CLANA   LPFNWKQEFRTLEVTLEDFSKLNKQDIRYLGKIFSSATSLRLQIKRCAGVAGSLSLVLSTCKNIY
CLANB   ------------------------------------------------------------------

CLANA   SLMVEASPLTIEDERHITSVTNLKTLSIHDLQNQRLPGGLTDSLGNIKNLIKLIHDNIKMNEEDA
CLANB   -------------------------------------SGLTDSLGNIKNLIKLIHDNIKMNEEDA

CLANA   IKLAEGLKNLKKMCLFHLTHLSDIGEGMDYIVKSLSSEPCDLEEIQLVSCCLSANAVKILAQNLH
CLANB   IKLAEGLKNLKKMCLFHLTHLSDIGEGMDYIVKSLSSEPCDLEEIQLVSCCLSANAVKILAQNLH

CLANA   NLVKLSILDLSENYLEKDGNEALHELIDRMNVLEQLTALMLPHGCDVQGSLSSLLKHLEEVPQLV
CLANB   NLVKLSILDLSENYLEKDGNEALHELIDRMNVLEQLTALMLPHGCDVQGSLSSLLKHLEEVPQLV

CLANA   KIGLKNWRLTDTEIRILGAFFGKNPLKNFQQLNLAGNRVSSDGWLAFMGVFENLKQLVFFDFSTK
CLANB   KIGLKNWRLTDTEIRILGAFFGKNPLKNFQQLNLAGNRVSSDGWLAFMGVFENLKQLVFFDFSTK

CLANA   EFLPDPALVRKLSQVLSKLIFIQEARLVGNQFDDDLSVITGAFKLVTA
CLANB   EFLPDPALVRKLSQVLSKLIFIQEARLVGNQFDDDLSVITGAFKLVTA
```

Fig. 2

XKPGQFWSRRCGAAGLRCCGATGQERVLRSRQSRCCVRAGGGAERPRITRSRSPSRSRSRE
SWRGVGLGVGAQAARG  18030 (76)

CEMCSQEAFQAQRSQLVELLVSGSLEGFESVLDNLLSEVLSRE      CARD-A

DYTGTHLLGQPLSHLARRLLDTVWNKGTWACQKLIAAAQEAQADSQSPKLHGCWDPHSLH

PARDLGSRDAYVRRLESHVEMVDLAEEEVSQLEDFIELPITESQR      CARD-B

ARMADA1

VRANELASFLQRVGHEVPLALPLE

AATCKKIMAKLRTTVSAQSRFLSTVDGAETLCLE
DIYTENVLEVMADVGAGPPQKSPATLGLEELFSTPGHLNQDADTVLVVGEAGSEKSTLL      P-LOOP

QRLHLLVLAGQDQERAFVTPTSRQLQQAAKPLSVRTLLERQCFRDVGQEDIFQLLLKS      NB-ARC

IPERVALIEDEDIEKFRFTDRSREGSPTDPFSVQILARLLQENLLKNARGVVTSRDA

VSALTRGVFRFDTNLKGFSRQGELAILRGRHERGVADRLRLLQFTSAIEGLCHLPVTS

MWRGQPLLLAGESFRVVTDNTTALLQHFMAMVPPRSASPGLGPSLARGVFLLAE

GRLAWFERICGGTVFSAQQLQAQJSPDDISLGFT

Figure 3

```
COP       MADKVLKEKRKLFIHSMGEGTINGLLDELL  30
caspase-1 MADKVLKEKRKLFIRSMGEGTINGLLDELL  30

QTRVLNQEEMEKVKRENATVMDKTRALIDS  60
          QTRVLNKEEMEKVKRENATVMDKTRALIDS  60

VIPKGAQACQICITYICEEDSYLAETLGLS  90
          VIPKGAQACQICITYICEEDSYLAGTLGLS  90

AGPIRGN  97
          ADQTSGN  97
```

Figure 4

```
            M A D K V L L E K R K L L I N S L G E G T I N G L L D E L L E T N V L S Q E D M   Majority
                          10                  20                  30                  40
    1   M A D K V L K E K R K L F I R S M G E G T I N G L L D E L L Q T R V L N K E E M       cas-1
    1   M - - - I L L K K R R L L I N S L G E G T I N G L L D E L L E T N V L S Q E D T       cop-2

E I V K R E N A T V I D K A R A L L D S V I R K G A G A C E I C I T Y I C E E D   Majority
                          50                  60                  70                  80
   41   E K V K R E N A T V M D K T R A L I D S V I P K G A Q A C Q I C I T Y I C E E D       cas-1
   38   E I V K C E N V T V I D K A R D L L D S V I R K G A G A C E I C I T Y I C E E D       cop-2

S Y L A G T L G L S A G N A V Q A G G A C S T S S G Q D L                         Majority
                          90                 100
   81   S Y L A G T L G L S A P Q A V Q D N P A M P T S S G                                   cas-1
   78   R Y L A G T L G L S A G N D Y R A G G I C S P P R A Q D L                             cop-2
```

Figure 5

SEQUENCE LISTING

<160> NUMBER OF SEQ ID NOS: 195

<210> SEQ ID NO 1
<211> LENGTH:
<212> TYPE:
<213> ORGANISM:

<400> SEQUENCE: 1

000

-continued

<210> SEQ ID NO 2
<211> LENGTH:
<212> TYPE:
<213> ORGANISM:

<400> SEQUENCE: 2

000

<210> SEQ ID NO 3
<211> LENGTH:
<212> TYPE:
<213> ORGANISM:

<400> SEQUENCE: 3

000

<210> SEQ ID NO 4
<211> LENGTH:
<212> TYPE:
<213> ORGANISM:

<400> SEQUENCE: 4

000

<210> SEQ ID NO 5
<211> LENGTH:
<212> TYPE:
<213> ORGANISM:

<400> SEQUENCE: 5

000

<210> SEQ ID NO 6
<211> LENGTH:
<212> TYPE:
<213> ORGANISM:

<400> SEQUENCE: 6

000

<210> SEQ ID NO 7
<211> LENGTH:
<212> TYPE:
<213> ORGANISM:

<400> SEQUENCE: 7

000

<210> SEQ ID NO 8
<211> LENGTH:
<212> TYPE:
<213> ORGANISM:

<400> SEQUENCE: 8

000

<210> SEQ ID NO 9
<211> LENGTH:
<212> TYPE:
<213> ORGANISM:

<400> SEQUENCE: 9

000

<210> SEQ ID NO 10
<211> LENGTH:
<212> TYPE:
<213> ORGANISM:

<400> SEQUENCE: 10

000

<210> SEQ ID NO 11
<211> LENGTH: 1038
<212> TYPE: DNA
<213> ORGANISM: Homo sapien
<220> FEATURE:
<221> NAME/KEY: CDS
<222> LOCATION: (1)...(930)

<400> SEQUENCE: 11

```
atg gct acc gag agt act ccc tca gag atc ata gaa aga gaa aga aaa      48
Met Ala Thr Glu Ser Thr Pro Ser Glu Ile Ile Glu Arg Glu Arg Lys
1               5                   10                  15 aag ttg ctt gaa atc ctt caa cat gat cct gat tct atc tta gac acg      96
Lys Leu Leu Glu Ile Leu Gln His Asp Pro Asp Ser Ile Leu Asp Thr
            20                  25                  30 tta act tct cgg agg ctg att tct gag gaa gag tat gag act ctg gag    144
Leu Thr Ser Arg Arg Leu Ile Ser Glu Glu Glu Tyr Glu Thr Leu Glu
        35                  40                  45 aat gtt aca gat ctc ctg aag aaa agt cgg aag ctg tta att ttg gta    192
Asn Val Thr Asp Leu Leu Lys Lys Ser Arg Lys Leu Leu Ile Leu Val
    50                  55                  60 cag aaa aag gga gag gcg acc tgt cag cat ttt ctc aag tgt tta ttt    240
Gln Lys Lys Gly Glu Ala Thr Cys Gln His Phe Leu Lys Cys Leu Phe
65                  70                  75                  80 agt act ttt cca cag tca gct gcc att tgc ggc tta agg cat gaa gtt    288
Ser Thr Phe Pro Gln Ser Ala Ala Ile Cys Gly Leu Arg His Glu Val
                85                  90                  95 tta aaa cat gag aat aca gta cct cct caa tct atg ggg gca agc agt    336
Leu Lys His Glu Asn Thr Val Pro Pro Gln Ser Met Gly Ala Ser Ser
            100                 105                 110 aat tca gaa gat gct ttt tct cct gga ata aaa cag cct gaa gcc cct    384
Asn Ser Glu Asp Ala Phe Ser Pro Gly Ile Lys Gln Pro Glu Ala Pro
        115                 120                 125 gag atc aca gtg ttc ttc agt gag aag gaa cac ttg gat ttg gaa acc    432
Glu Ile Thr Val Phe Phe Ser Glu Lys Glu His Leu Asp Leu Glu Thr
    130                 135                 140 tct gag ttt ttc agg gac aag aaa act agt tat agg gaa aca gct ttg    480
Ser Glu Phe Phe Arg Asp Lys Lys Thr Ser Tyr Arg Glu Thr Ala Leu
145                 150                 155                 160 tct gcc agg aag aat gag aag gaa tat gac aca cca gaa gtc aca tta    528
Ser Ala Arg Lys Asn Glu Lys Glu Tyr Asp Thr Pro Glu Val Thr Leu
                165                 170                 175 tca tat tca gtt gag aaa gtt gga tgt gaa gtt cca gca act att aca    576
Ser Tyr Ser Val Glu Lys Val Gly Cys Glu Val Pro Ala Thr Ile Thr
            180                 185                 190 tat ata aaa gat gga cag aga tat gag gag cta gat gat tct tta tac    624
Tyr Ile Lys Asp Gly Gln Arg Tyr Glu Glu Leu Asp Asp Ser Leu Tyr
        195                 200                 205 tta gga aaa gag gaa tat cta gga tct gtt gac acc cct gaa gat gca    672
Leu Gly Lys Glu Glu Tyr Leu Gly Ser Val Asp Thr Pro Glu Asp Ala
    210                 215                 220 gaa gcc act gtg gaa gag gag gtt tat gat gac cca gag cac gtt gga    720
Glu Ala Thr Val Glu Glu Glu Val Tyr Asp Asp Pro Glu His Val Gly
225                 230                 235                 240
```

```
tat gat ggt gaa gag gac ttc gag aat tca gaa acc aca gag ttc tct        768
Tyr Asp Gly Glu Glu Asp Phe Glu Asn Ser Glu Thr Thr Glu Phe Ser
            245                 250                 255 ggt gaa gaa cca agt tat gag gga tca gaa acc agc ctt tca ttg gag        816
Gly Glu Glu Pro Ser Tyr Glu Gly Ser Glu Thr Ser Leu Ser Leu Glu
        260                 265                 270 gag gaa cag gag aaa agt ata gaa ggc tgg tct cga act cat ggg ctt        864
Glu Glu Gln Glu Lys Ser Ile Glu Gly Trp Ser Arg Thr His Gly Leu
    275                 280                 285 aag cga tcc tcc cac gtt ggc ctc cca aag tgc tgg gat tac agg cgt        912
Lys Arg Ser Ser His Val Gly Leu Pro Lys Cys Trp Asp Tyr Arg Arg
290                 295                 300 gag cca ccc tgc ctg gcc tgaaaattct gcctcaaaca tctcaaacat               960
Glu Pro Pro Cys Leu Ala
305                 310 ccatttatat tttgtacaag aaagtaaata aaatttttct ttttaacatt aaaaaaaaaa     1020
aaaaaaaaaa aatctaga                                                  1038

<210> SEQ ID NO 12
<211> LENGTH: 310
<212> TYPE: PRT
<213> ORGANISM: Homo sapien

<400> SEQUENCE: 12

Met Ala Thr Glu Ser Thr Pro Ser Glu Ile Ile Glu Arg Glu Arg Lys
1               5                   10                  15

Lys Leu Leu Glu Ile Leu Gln His Asp Pro Asp Ser Ile Leu Asp Thr
            20                  25                  30

Leu Thr Ser Arg Arg Leu Ile Ser Glu Glu Tyr Glu Thr Leu Glu
        35                  40                  45

Asn Val Thr Asp Leu Leu Lys Lys Ser Arg Lys Leu Leu Ile Leu Val
    50                  55                  60

Gln Lys Lys Gly Glu Ala Thr Cys Gln His Phe Leu Lys Cys Leu Phe
65                  70                  75                  80

Ser Thr Phe Pro Gln Ser Ala Ala Ile Cys Gly Leu Arg His Glu Val
                85                  90                  95

Leu Lys His Glu Asn Thr Val Pro Pro Gln Ser Met Gly Ala Ser Ser
            100                 105                 110

Asn Ser Glu Asp Ala Phe Ser Pro Gly Ile Lys Gln Pro Glu Ala Pro
        115                 120                 125

Glu Ile Thr Val Phe Phe Ser Glu Lys Glu His Leu Asp Leu Glu Thr
    130                 135                 140

Ser Glu Phe Phe Arg Asp Lys Lys Thr Ser Tyr Arg Glu Thr Ala Leu
145                 150                 155                 160

Ser Ala Arg Lys Asn Glu Lys Glu Tyr Asp Thr Pro Glu Val Thr Leu
                165                 170                 175

Ser Tyr Ser Val Glu Lys Val Gly Cys Glu Val Pro Ala Thr Ile Thr
            180                 185                 190

Tyr Ile Lys Asp Gly Gln Arg Tyr Glu Glu Leu Asp Asp Ser Leu Tyr
        195                 200                 205

Leu Gly Lys Glu Glu Tyr Leu Gly Ser Val Asp Thr Pro Glu Asp Ala
    210                 215                 220

Glu Ala Thr Val Glu Glu Val Tyr Asp Asp Pro Glu His Val Gly
225                 230                 235                 240

Tyr Asp Gly Glu Glu Asp Phe Glu Asn Ser Glu Thr Thr Glu Phe Ser
                245                 250                 255
```

Gly Glu Glu Pro Ser Tyr Glu Gly Ser Glu Thr Ser Leu Ser Leu Glu
            260                 265                 270

Glu Glu Gln Glu Lys Ser Ile Glu Gly Trp Ser Arg Thr His Gly Leu
        275                 280                 285

Lys Arg Ser Ser His Val Gly Leu Pro Lys Cys Trp Asp Tyr Arg Arg
290                 295                 300

Glu Pro Pro Cys Leu Ala
305                 310

<210> SEQ ID NO 13
<211> LENGTH:
<212> TYPE:
<213> ORGANISM:

<400> SEQUENCE: 13

000

<210> SEQ ID NO 14
<211> LENGTH:
<212> TYPE:
<213> ORGANISM:

<400> SEQUENCE: 14

000

<210> SEQ ID NO 15
<211> LENGTH:
<212> TYPE:
<213> ORGANISM:

<400> SEQUENCE: 15

000

<210> SEQ ID NO 16
<211> LENGTH:
<212> TYPE:
<213> ORGANISM:

<400> SEQUENCE: 16

000

<210> SEQ ID NO 17
<211> LENGTH:
<212> TYPE:
<213> ORGANISM:

<400> SEQUENCE: 17

000

<210> SEQ ID NO 18
<211> LENGTH:
<212> TYPE:
<213> ORGANISM:

<400> SEQUENCE: 18

000

<210> SEQ ID NO 19
<211> LENGTH:
<212> TYPE:
<213> ORGANISM:

```
<400> SEQUENCE: 19

000

<210> SEQ ID NO 20
<211> LENGTH:
<212> TYPE:
<213> ORGANISM:

<400> SEQUENCE: 20

000

<210> SEQ ID NO 21
<211> LENGTH:
<212> TYPE:
<213> ORGANISM:

<400> SEQUENCE: 21

000

<210> SEQ ID NO 22
<211> LENGTH:
<212> TYPE:
<213> ORGANISM:

<400> SEQUENCE: 22

000

<210> SEQ ID NO 23
<211> LENGTH:
<212> TYPE:
<213> ORGANISM:

<400> SEQUENCE: 23

000

<210> SEQ ID NO 24
<211> LENGTH:
<212> TYPE:
<213> ORGANISM:

<400> SEQUENCE: 24

000

<210> SEQ ID NO 25
<211> LENGTH:
<212> TYPE:
<213> ORGANISM:

<400> SEQUENCE: 25

000

<210> SEQ ID NO 26
<211> LENGTH:
<212> TYPE:
<213> ORGANISM:

<400> SEQUENCE: 26

000

<210> SEQ ID NO 27
<211> LENGTH:
<212> TYPE:
<213> ORGANISM:
```

-continued

```
<400> SEQUENCE: 27

000

<210> SEQ ID NO 28
<211> LENGTH:
<212> TYPE:
<213> ORGANISM:

<400> SEQUENCE: 28

000

<210> SEQ ID NO 29
<211> LENGTH:
<212> TYPE:
<213> ORGANISM:

<400> SEQUENCE: 29

000

<210> SEQ ID NO 30
<211> LENGTH:
<212> TYPE:
<213> ORGANISM:

<400> SEQUENCE: 30

000

<210> SEQ ID NO 31
<211> LENGTH:
<212> TYPE:
<213> ORGANISM:

<400> SEQUENCE: 31

000

<210> SEQ ID NO 32
<211> LENGTH:
<212> TYPE:
<213> ORGANISM:

<400> SEQUENCE: 32

000

<210> SEQ ID NO 33
<211> LENGTH:
<212> TYPE:
<213> ORGANISM:

<400> SEQUENCE: 33

000

<210> SEQ ID NO 34
<211> LENGTH:
<212> TYPE:
<213> ORGANISM:

<400> SEQUENCE: 34

000

<210> SEQ ID NO 35
<211> LENGTH:
<212> TYPE:
<213> ORGANISM:
```

-continued

```
<400> SEQUENCE: 35

000

<210> SEQ ID NO 36
<211> LENGTH:
<212> TYPE:
<213> ORGANISM:

<400> SEQUENCE: 36

000

<210> SEQ ID NO 37
<211> LENGTH:
<212> TYPE:
<213> ORGANISM:

<400> SEQUENCE: 37

000

<210> SEQ ID NO 38
<211> LENGTH:
<212> TYPE:
<213> ORGANISM:

<400> SEQUENCE: 38

000

<210> SEQ ID NO 39
<211> LENGTH:
<212> TYPE:
<213> ORGANISM:

<400> SEQUENCE: 39

000

<210> SEQ ID NO 40
<211> LENGTH:
<212> TYPE:
<213> ORGANISM:

<400> SEQUENCE: 40

000

<210> SEQ ID NO 41
<211> LENGTH:
<212> TYPE:
<213> ORGANISM:

<400> SEQUENCE: 41

000

<210> SEQ ID NO 42
<211> LENGTH:
<212> TYPE:
<213> ORGANISM:

<400> SEQUENCE: 42

000

<210> SEQ ID NO 43
<211> LENGTH:
<212> TYPE:
<213> ORGANISM:
```

```
<400> SEQUENCE: 43

000

<210> SEQ ID NO 44
<211> LENGTH:
<212> TYPE:
<213> ORGANISM:

<400> SEQUENCE: 44

000

<210> SEQ ID NO 45
<211> LENGTH:
<212> TYPE:
<213> ORGANISM:

<400> SEQUENCE: 45

000

<210> SEQ ID NO 46
<211> LENGTH:
<212> TYPE:
<213> ORGANISM:

<400> SEQUENCE: 46

000

<210> SEQ ID NO 47
<211> LENGTH:
<212> TYPE:
<213> ORGANISM:

<400> SEQUENCE: 47

000

<210> SEQ ID NO 48
<211> LENGTH:
<212> TYPE:
<213> ORGANISM:

<400> SEQUENCE: 48

000

<210> SEQ ID NO 49
<211> LENGTH:
<212> TYPE:
<213> ORGANISM:

<400> SEQUENCE: 49

000

<210> SEQ ID NO 50
<211> LENGTH:
<212> TYPE:
<213> ORGANISM:

<400> SEQUENCE: 50

000

<210> SEQ ID NO 51
<211> LENGTH:
<212> TYPE:
<213> ORGANISM:
```

-continued

```
<400> SEQUENCE: 51

000

<210> SEQ ID NO 52
<211> LENGTH:
<212> TYPE:
<213> ORGANISM:

<400> SEQUENCE: 52

000

<210> SEQ ID NO 53
<211> LENGTH:
<212> TYPE:
<213> ORGANISM:

<400> SEQUENCE: 53

000

<210> SEQ ID NO 54
<211> LENGTH:
<212> TYPE:
<213> ORGANISM:

<400> SEQUENCE: 54

000

<210> SEQ ID NO 55
<211> LENGTH:
<212> TYPE:
<213> ORGANISM:

<400> SEQUENCE: 55

000

<210> SEQ ID NO 56
<211> LENGTH:
<212> TYPE:
<213> ORGANISM:

<400> SEQUENCE: 56

000

<210> SEQ ID NO 57
<211> LENGTH:
<212> TYPE:
<213> ORGANISM:

<400> SEQUENCE: 57

000

<210> SEQ ID NO 58
<211> LENGTH:
<212> TYPE:
<213> ORGANISM:

<400> SEQUENCE: 58

000

<210> SEQ ID NO 59
<211> LENGTH:
<212> TYPE:
<213> ORGANISM:
```

-continued

```
<400> SEQUENCE: 59

000

<210> SEQ ID NO 60
<211> LENGTH:
<212> TYPE:
<213> ORGANISM:

<400> SEQUENCE: 60

000

<210> SEQ ID NO 61
<211> LENGTH:
<212> TYPE:
<213> ORGANISM:

<400> SEQUENCE: 61

000

<210> SEQ ID NO 62
<211> LENGTH:
<212> TYPE:
<213> ORGANISM:

<400> SEQUENCE: 62

000

<210> SEQ ID NO 63
<211> LENGTH:
<212> TYPE:
<213> ORGANISM:

<400> SEQUENCE: 63

000

<210> SEQ ID NO 64
<211> LENGTH:
<212> TYPE:
<213> ORGANISM:

<400> SEQUENCE: 64

000

<210> SEQ ID NO 65
<211> LENGTH:
<212> TYPE:
<213> ORGANISM:

<400> SEQUENCE: 65

000

<210> SEQ ID NO 66
<211> LENGTH:
<212> TYPE:
<213> ORGANISM:

<400> SEQUENCE: 66

000

<210> SEQ ID NO 67
<211> LENGTH:
<212> TYPE:
<213> ORGANISM:
```

```
<400> SEQUENCE: 67

000

<210> SEQ ID NO 68
<211> LENGTH:
<212> TYPE:
<213> ORGANISM:

<400> SEQUENCE: 68

000

<210> SEQ ID NO 69
<211> LENGTH:
<212> TYPE:
<213> ORGANISM:

<400> SEQUENCE: 69

000

<210> SEQ ID NO 70
<211> LENGTH:
<212> TYPE:
<213> ORGANISM:

<400> SEQUENCE: 70

000

<210> SEQ ID NO 71
<211> LENGTH:
<212> TYPE:
<213> ORGANISM:

<400> SEQUENCE: 71

000

<210> SEQ ID NO 72
<211> LENGTH:
<212> TYPE:
<213> ORGANISM:

<400> SEQUENCE: 72

000

<210> SEQ ID NO 73
<211> LENGTH:
<212> TYPE:
<213> ORGANISM:

<400> SEQUENCE: 73

000

<210> SEQ ID NO 74
<211> LENGTH: 19
<212> TYPE: DNA
<213> ORGANISM: Artificial Sequence
<220> FEATURE:
<223> OTHER INFORMATION: Primer

<400> SEQUENCE: 74
tacttacttt gtcccttca                                            19
```

```
<210> SEQ ID NO 75
<211> LENGTH: 19
<212> TYPE: DNA
<213> ORGANISM: Artificial Sequence
<220> FEATURE:
<223> OTHER INFORMATION: Primer

<400> SEQUENCE: 75
tatttgtccc catctcgtc                                                    19

<210> SEQ ID NO 76
<211> LENGTH: 28
<212> TYPE: DNA
<213> ORGANISM: Artificial Sequence
<220> FEATURE:
<223> OTHER INFORMATION: Primer

<400> SEQUENCE: 76
cggaattcat ggctaccgag agtactcc                                          28

<210> SEQ ID NO 77
<211> LENGTH: 17
<212> TYPE: DNA
<213> ORGANISM: Artificial Sequence
<220> FEATURE:
<223> OTHER INFORMATION: Primer

<400> SEQUENCE: 77
gtaaaacgac ggccagt                                                      17

<210> SEQ ID NO 78
<211> LENGTH: 27
<212> TYPE: DNA
<213> ORGANISM: Artificial Sequence
<220> FEATURE:
<223> OTHER INFORMATION: Primer

<400> SEQUENCE: 78
gcagaagcca ctgtggaaga ggaggtt                                           27

<210> SEQ ID NO 79
<211> LENGTH: 28
<212> TYPE: DNA
<213> ORGANISM: Artificial Sequence
<220> FEATURE:
<223> OTHER INFORMATION: Primer

<400> SEQUENCE: 79
atacgactca ctatagggcg aattggcc                                          28

<210> SEQ ID NO 80
<211> LENGTH:
<212> TYPE:
<213> ORGANISM:
<220> FEATURE:
<223> OTHER INFORMATION: Primer

<400> SEQUENCE: 80

000

<210> SEQ ID NO 81
<211> LENGTH:
<212> TYPE:
<213> ORGANISM:
<220> FEATURE:
<223> OTHER INFORMATION: Primer
```

<400> SEQUENCE: 81

000

<210> SEQ ID NO 82
<211> LENGTH: 3030
<212> TYPE: DNA
<213> ORGANISM: Homo sapien
<220> FEATURE:
<221> NAME/KEY: CDS
<222> LOCATION: (1)...(1680)

<400> SEQUENCE: 82

| tgt | gaa | atg | tgc | tcg | cag | gag | gct | ttt | cag | gca | cag | agg | agc | cag | ctg | 48 |
|---|---|---|---|---|---|---|---|---|---|---|---|---|---|---|---|---|
| Cys | Glu | Met | Cys | Ser | Gln | Glu | Ala | Phe | Gln | Ala | Gln | Arg | Ser | Gln | Leu | |
| 1 | | | | 5 | | | | | 10 | | | | | 15 | | |

| gtc | gag | ctg | ctg | gtc | tca | ggg | tcc | ctg | gaa | ggc | ttc | gag | agt | gtc | ctg | 96 |
|---|---|---|---|---|---|---|---|---|---|---|---|---|---|---|---|---|
| Val | Glu | Leu | Leu | Val | Ser | Gly | Ser | Leu | Glu | Gly | Phe | Glu | Ser | Val | Leu | |
| | | | 20 | | | | | 25 | | | | | 30 | | | |

| gac | tgg | ctg | ctg | tcc | tgg | gag | gtc | ctc | tcc | tgg | gag | gac | tac | gag | ggc | 144 |
|---|---|---|---|---|---|---|---|---|---|---|---|---|---|---|---|---|
| Asp | Trp | Leu | Leu | Ser | Trp | Glu | Val | Leu | Ser | Trp | Glu | Asp | Tyr | Glu | Gly | |
| | | | 35 | | | | | 40 | | | | | 45 | | | |

| ttc | cac | ctc | ctg | ggc | cag | cct | ctc | tcc | cac | ttg | gcc | agg | cgc | ctt | ctg | 192 |
|---|---|---|---|---|---|---|---|---|---|---|---|---|---|---|---|---|
| Phe | His | Leu | Leu | Gly | Gln | Pro | Leu | Ser | His | Leu | Ala | Arg | Arg | Leu | Leu | |
| | 50 | | | | | 55 | | | | | 60 | | | | | |

| gac | acc | gtc | tgg | aat | aag | ggt | act | tgg | gcc | tgt | cag | aag | ctc | atc | gcg | 240 |
|---|---|---|---|---|---|---|---|---|---|---|---|---|---|---|---|---|
| Asp | Thr | Val | Trp | Asn | Lys | Gly | Thr | Trp | Ala | Cys | Gln | Lys | Leu | Ile | Ala | |
| 65 | | | | | 70 | | | | | 75 | | | | | 80 | |

| gct | gcc | caa | gaa | gcc | cag | gcc | gac | agc | cag | tcc | ccc | aag | ctg | cat | ggc | 288 |
|---|---|---|---|---|---|---|---|---|---|---|---|---|---|---|---|---|
| Ala | Ala | Gln | Glu | Ala | Gln | Ala | Asp | Ser | Gln | Ser | Pro | Lys | Leu | His | Gly | |
| | | | | 85 | | | | | 90 | | | | | 95 | | |

| tgc | tgg | gac | ccc | cac | tcg | ctc | cac | cca | gcc | cga | gac | ctg | cag | agt | cac | 336 |
|---|---|---|---|---|---|---|---|---|---|---|---|---|---|---|---|---|
| Cys | Trp | Asp | Pro | His | Ser | Leu | His | Pro | Ala | Arg | Asp | Leu | Gln | Ser | His | |
| | | | 100 | | | | | 105 | | | | | 110 | | | |

| cgg | cca | gcc | att | gtc | agg | agg | ctc | cac | agc | cat | gtg | gag | aac | atg | ctg | 384 |
|---|---|---|---|---|---|---|---|---|---|---|---|---|---|---|---|---|
| Arg | Pro | Ala | Ile | Val | Arg | Arg | Leu | His | Ser | His | Val | Glu | Asn | Met | Leu | |
| | | 115 | | | | | 120 | | | | | 125 | | | | |

| gac | ctg | gca | tgg | gag | cgg | ggt | ttc | gtc | agc | cag | tat | gaa | tgt | gat | gaa | 432 |
|---|---|---|---|---|---|---|---|---|---|---|---|---|---|---|---|---|
| Asp | Leu | Ala | Trp | Glu | Arg | Gly | Phe | Val | Ser | Gln | Tyr | Glu | Cys | Asp | Glu | |
| | 130 | | | | | 135 | | | | | 140 | | | | | |

| atc | agg | ttg | ccg | atc | ttc | aca | ccg | tcc | cag | agg | gca | aga | agg | ctg | ctt | 480 |
|---|---|---|---|---|---|---|---|---|---|---|---|---|---|---|---|---|
| Ile | Arg | Leu | Pro | Ile | Phe | Thr | Pro | Ser | Gln | Arg | Ala | Arg | Arg | Leu | Leu | |
| 145 | | | | | 150 | | | | | 155 | | | | | 160 | |

| gat | ctt | gcc | acg | gtg | aaa | gcg | aat | gga | ttg | gct | gcc | ttc | ctt | cta | caa | 528 |
|---|---|---|---|---|---|---|---|---|---|---|---|---|---|---|---|---|
| Asp | Leu | Ala | Thr | Val | Lys | Ala | Asn | Gly | Leu | Ala | Ala | Phe | Leu | Leu | Gln | |
| | | | | 165 | | | | | 170 | | | | | 175 | | |

| cat | gtt | cag | gaa | tta | cca | gtc | cca | ttg | gcc | ctg | cct | ttg | gaa | gct | gcc | 576 |
|---|---|---|---|---|---|---|---|---|---|---|---|---|---|---|---|---|
| His | Val | Gln | Glu | Leu | Pro | Val | Pro | Leu | Ala | Leu | Pro | Leu | Glu | Ala | Ala | |
| | | | 180 | | | | | 185 | | | | | 190 | | | |

| aca | tgc | aag | aag | tat | atg | gcc | aag | ctg | agg | acc | acg | gtg | tct | gct | cag | 624 |
|---|---|---|---|---|---|---|---|---|---|---|---|---|---|---|---|---|
| Thr | Cys | Lys | Lys | Tyr | Met | Ala | Lys | Leu | Arg | Thr | Thr | Val | Ser | Ala | Gln | |
| | | 195 | | | | | 200 | | | | | 205 | | | | |

| tct | cgc | ttc | ctc | agt | acc | tat | gat | gga | gca | gag | acg | ctc | tgc | ctg | gag | 672 |
|---|---|---|---|---|---|---|---|---|---|---|---|---|---|---|---|---|
| Ser | Arg | Phe | Leu | Ser | Thr | Tyr | Asp | Gly | Ala | Glu | Thr | Leu | Cys | Leu | Glu | |
| | 210 | | | | | 215 | | | | | 220 | | | | | |

| gac | ata | tac | aca | gag | aat | gtc | ctg | gag | gtc | tgg | gca | gat | gtg | ggc | atg | 720 |
|---|---|---|---|---|---|---|---|---|---|---|---|---|---|---|---|---|
| Asp | Ile | Tyr | Thr | Glu | Asn | Val | Leu | Glu | Val | Trp | Ala | Asp | Val | Gly | Met | |
| 225 | | | | | 230 | | | | | 235 | | | | | 240 | |

| gct | gga | ccc | ccg | cag | aag | agc | cca | gcc | acc | ctg | ggc | ctg | gag | gag | ctc | 768 |
|---|---|---|---|---|---|---|---|---|---|---|---|---|---|---|---|---|
| Ala | Gly | Pro | Pro | Gln | Lys | Ser | Pro | Ala | Thr | Leu | Gly | Leu | Glu | Glu | Leu | |
| | | | | 245 | | | | | 250 | | | | | 255 | | |

-continued

| | |
|---|---|
| ttc agc acc cct ggc cac ctc aat gac gat gcg gac act gtg ctg gtg<br>Phe Ser Thr Pro Gly His Leu Asn Asp Asp Ala Asp Thr Val Leu Val<br>260                                 265                            270 | 816 |
| gtg ggt gag gcg ggc agt ggc aag agc acg ctc ctg cag cgg ctg cac<br>Val Gly Glu Ala Gly Ser Gly Lys Ser Thr Leu Leu Gln Arg Leu His<br>275                                280                          285 | 864 |
| ttg ctg tgg gct gca ggg caa gac ttc cag gaa ttt ctc ttt gtc ttc<br>Leu Leu Trp Ala Ala Gly Gln Asp Phe Gln Glu Phe Leu Phe Val Phe<br>290                                295                          300 | 912 |
| cca ttc agc tgc cgg cag ctg cag tgc atg gcc aaa cca ctc tct gtg<br>Pro Phe Ser Cys Arg Gln Leu Gln Cys Met Ala Lys Pro Leu Ser Val<br>305                                310                         315                 320 | 960 |
| cgg act cta ctc ttt gag cac tgc tgt tgg cct gat gtt ggt caa gaa<br>Arg Thr Leu Leu Phe Glu His Cys Cys Trp Pro Asp Val Gly Gln Glu<br>325                                330                         335 | 1008 |
| gac atc ttc cag tta ctc ctt gac cac cct gac cgt gtc ctg tta acc<br>Asp Ile Phe Gln Leu Leu Leu Asp His Pro Asp Arg Val Leu Leu Thr<br>340                                345                         350 | 1056 |
| ttt gat ggc ttt gac gag ttc aag ttc agg ttc acg gat cgt gaa cgc<br>Phe Asp Gly Phe Asp Glu Phe Lys Phe Arg Phe Thr Asp Arg Glu Arg<br>355                                360                         365 | 1104 |
| cac tgc tcc ccg acc gac ccc acc tct gtc cag acc ctg ctc ttc aac<br>His Cys Ser Pro Thr Asp Pro Thr Ser Val Gln Thr Leu Leu Phe Asn<br>370                                375                         380 | 1152 |
| ctt ctg cag ggc aac ctg ctg aag aat gcc cgc aag gtg gtg acc agc<br>Leu Leu Gln Gly Asn Leu Leu Lys Asn Ala Arg Lys Val Val Thr Ser<br>385                                390                         395                 400 | 1200 |
| cgt ccg gcc gct gtg tcg gcg ttc ctc agg aag tac atc cgc acc gag<br>Arg Pro Ala Ala Val Ser Ala Phe Leu Arg Lys Tyr Ile Arg Thr Glu<br>405                                410                         415 | 1248 |
| ttc aac ctc aag ggc ttc tct gaa cag ggc atc gag ctg tac ctg agg<br>Phe Asn Leu Lys Gly Phe Ser Glu Gln Gly Ile Glu Leu Tyr Leu Arg<br>420                                425                         430 | 1296 |
| aag cgc cat cat gag ccc ggg gtg gcg gac cgc ctc atc cgc ctg ctc<br>Lys Arg His His Glu Pro Gly Val Ala Asp Arg Leu Ile Arg Leu Leu<br>435                                440                         445 | 1344 |
| caa gag acc tca gcc ctg cac ggt ttg tgc cac ctg cct gtc ttc tca<br>Gln Glu Thr Ser Ala Leu His Gly Leu Cys His Leu Pro Val Phe Ser<br>450                                455                         460 | 1392 |
| tgg atg gtg tcc aaa tgc cac cag gaa ctg ttg ctg cag gag ggg ggg<br>Trp Met Val Ser Lys Cys His Gln Glu Leu Leu Leu Gln Glu Gly Gly<br>465                                470                         475                 480 | 1440 |
| tcc cca aag acc act aca gat atg tac ctg ctg att ctg cag cat ttt<br>Ser Pro Lys Thr Thr Thr Asp Met Tyr Leu Leu Ile Leu Gln His Phe<br>                           485                         490                         495 | 1488 |
| ctg ctg cat gcc acc ccc cca gac tca gct tcc caa ggt ctg gga ccc<br>Leu Leu His Ala Thr Pro Pro Asp Ser Ala Ser Gln Gly Leu Gly Pro<br>                         500                         505                         510 | 1536 |
| agt ctt ctt cgg ggc cgc ctc ccc acc ctc ctg cac ctg ggc aga ctg<br>Ser Leu Leu Arg Gly Arg Leu Pro Thr Leu Leu His Leu Gly Arg Leu<br>                         515                         520                         525 | 1584 |
| gct ctg tgg ggc ctg ggc atg tgc tgc tac gtg ttc tca gcc cag cag<br>Ala Leu Trp Gly Leu Gly Met Cys Cys Tyr Val Phe Ser Ala Gln Gln<br>                         530                         535                         540 | 1632 |
| ctc cag gca gca cag gtc agc cct gat gac att tct ctt ggc ttc ctg<br>Leu Gln Ala Ala Gln Val Ser Pro Asp Asp Ile Ser Leu Gly Phe Leu<br>545                                550                         555                         560 | 1680 |
| gtgcgtgcca aggtgtcgt gccagggagt acgcgcccc tggaattcct tcacatcact | 1740 |
| ttccagtgct tctttgccgc gttctacctg gcactcagtg ctgatgtgcc accagctttg | 1800 |

```
ctcagacacc tcttcaattg tggcaggcca ggcaactcac caatggccag gctcctgccc    1860
acgatgtgca tccaggcctc ggagggaaag gacagcagcg tggcagcttt gctgcagaag    1920
gccgagccgc acaaccttca gatcacagca gccttcctgg cagggctgtt gtcccgggag    1980
cactggggcc tgctggctga gtgccagaca tctgagaagg ccctgctccg cgccaggcc     2040
tgtgcccgct ggtgtctggc ccgcagcctc cgcaagcact ccactccat cccgccagct     2100
gcaccgggtg aggccaagag cgtgcatgcc atgcccgggt tcatctggct catccggagc    2160
ctgtacgaga tgcaggagga gcggctggct cggaaggctg cacgtggcct gaatgttggg    2220
cacctcaagt tgacattttg cagtgtgggc cccactgagt gtgctgccct ggcctttgtg    2280
ctgcagcacc tccggcggcc cgtggccctg cagctggact acaactctgt gggtgacatt    2340
ggcgtggagc agctgctgcc ttgccttggt gtctgcaagg ctctgtattt gcgcgataac    2400
aatatctcag accgaggcat ctgcaagctc attgaatgtg ctcttcactg cgagcaattg    2460
cagaagttag cgctggggaa taactacatc actgccgcgg gagcccaagt gctggccgag    2520
gggctccgag gcaacacctc cttgcagttc ctgggattct ggggcaacag agtgggtgac    2580
gagggggccc aggccctggc tgaagccttg ggtgatcacc agagcttgag gtggctcagc    2640
ctggtgggga caacattgg cagtgtgggt gcccaagcct tggcactgat gctggcaaag    2700
aacgtcatgc tagaagaact ctgcctggag gagaaccatc tccaggatga aggtgtatgt    2760
tctctcgcag aaggactgaa gaaaaattca gtttgaaaa tcctgaacat aaaaattcat    2820
gcttcgggat tcaacaaact cttggaaagc attttctgca tcctcctggt tgtggaagca    2880
ttttcctgc agaaagttgt caagattctt gaagaaatgg tagtcagttg gctagaggtc    2940
aggttgtcca ataactgcat cacctaccta ggggcagaag ccctcctgca ggcccttgaa    3000
aggaatgaca ccatcctgga agtctggtaa                                    3030
```

<210> SEQ ID NO 83
<211> LENGTH: 560
<212> TYPE: PRT
<213> ORGANISM: Homo sapien

<400> SEQUENCE: 83

```
Cys Glu Met Cys Ser Gln Glu Ala Phe Gln Ala Gln Arg Ser Gln Leu
 1               5                  10                  15

Val Glu Leu Leu Val Ser Gly Ser Leu Glu Gly Phe Glu Ser Val Leu
             20                  25                  30

Asp Trp Leu Leu Ser Trp Glu Val Leu Ser Trp Glu Asp Tyr Glu Gly
         35                  40                  45

Phe His Leu Leu Gly Gln Pro Leu Ser His Leu Ala Arg Arg Leu Leu
     50                  55                  60

Asp Thr Val Trp Asn Lys Gly Thr Trp Ala Cys Gln Lys Leu Ile Ala
 65                  70                  75                  80

Ala Ala Gln Glu Ala Gln Ala Asp Ser Gln Ser Pro Lys Leu His Gly
                 85                  90                  95

Cys Trp Asp Pro His Ser Leu His Pro Ala Arg Asp Leu Gln Ser His
            100                 105                 110

Arg Pro Ala Ile Val Arg Arg Leu His Ser His Val Glu Asn Met Leu
        115                 120                 125

Asp Leu Ala Trp Glu Arg Gly Phe Val Ser Gln Tyr Glu Cys Asp Glu
    130                 135                 140

Ile Arg Leu Pro Ile Phe Thr Pro Ser Gln Arg Ala Arg Arg Leu Leu
145                 150                 155                 160
```

```
Asp Leu Ala Thr Val Lys Ala Asn Gly Leu Ala Ala Phe Leu Leu Gln
                165                 170                 175

His Val Gln Glu Leu Pro Val Pro Leu Ala Leu Pro Leu Glu Ala Ala
            180                 185                 190

Thr Cys Lys Lys Tyr Met Ala Lys Leu Arg Thr Thr Val Ser Ala Gln
        195                 200                 205

Ser Arg Phe Leu Ser Thr Tyr Asp Gly Ala Glu Thr Leu Cys Leu Glu
    210                 215                 220

Asp Ile Tyr Thr Glu Asn Val Leu Glu Val Trp Ala Asp Val Gly Met
225                 230                 235                 240

Ala Gly Pro Pro Gln Lys Ser Pro Ala Thr Leu Gly Leu Glu Glu Leu
                245                 250                 255

Phe Ser Thr Pro Gly His Leu Asn Asp Asp Ala Asp Thr Val Leu Val
            260                 265                 270

Val Gly Glu Ala Gly Ser Gly Lys Ser Thr Leu Leu Gln Arg Leu His
        275                 280                 285

Leu Leu Trp Ala Ala Gly Gln Asp Phe Gln Glu Phe Leu Phe Val Phe
    290                 295                 300

Pro Phe Ser Cys Arg Gln Leu Gln Cys Met Ala Lys Pro Leu Ser Val
305                 310                 315                 320

Arg Thr Leu Leu Phe Glu His Cys Cys Trp Pro Asp Val Gly Gln Glu
                325                 330                 335

Asp Ile Phe Gln Leu Leu Leu Asp His Pro Asp Arg Val Leu Leu Thr
            340                 345                 350

Phe Asp Gly Phe Asp Glu Phe Lys Phe Arg Phe Thr Asp Arg Glu Arg
        355                 360                 365

His Cys Ser Pro Thr Asp Pro Thr Ser Val Gln Thr Leu Leu Phe Asn
    370                 375                 380

Leu Leu Gln Gly Asn Leu Leu Lys Asn Ala Arg Lys Val Val Thr Ser
385                 390                 395                 400

Arg Pro Ala Ala Val Ser Ala Phe Leu Arg Lys Tyr Ile Arg Thr Glu
                405                 410                 415

Phe Asn Leu Lys Gly Phe Ser Glu Gln Gly Ile Glu Leu Tyr Leu Arg
            420                 425                 430

Lys Arg His Glu Pro Gly Val Ala Asp Arg Leu Ile Arg Leu Leu
        435                 440                 445

Gln Glu Thr Ser Ala Leu His Gly Leu Cys His Leu Pro Val Phe Ser
    450                 455                 460

Trp Met Val Ser Lys Cys His Gln Glu Leu Leu Leu Gln Glu Gly Gly
465                 470                 475                 480

Ser Pro Lys Thr Thr Thr Asp Met Tyr Leu Leu Ile Leu Gln His Phe
                485                 490                 495

Leu Leu His Ala Thr Pro Pro Asp Ser Ala Ser Gln Gly Leu Gly Pro
            500                 505                 510

Ser Leu Leu Arg Gly Arg Leu Pro Thr Leu Leu His Leu Gly Arg Leu
        515                 520                 525

Ala Leu Trp Gly Leu Gly Met Cys Cys Tyr Val Phe Ser Ala Gln Gln
    530                 535                 540

Leu Gln Ala Ala Gln Val Ser Pro Asp Asp Ile Ser Leu Gly Phe Leu
545                 550                 555                 560
```

<210> SEQ ID NO 84
<211> LENGTH: 1107
<212> TYPE: DNA
<213> ORGANISM: Homo sapien

<400> SEQUENCE: 84

```
attcttttt    taacttttac    ttattcatta    ggatgatttc    ataatatatt    tcctggttta        60
gaggaaacag    gaacaatggc    taccgagagt    actccctcag    agatcataga    aagagaaaga      120
aaaagttgc     ttgaaatcct    tcaacatgat    cctgattcta    tcttagacac    gttaacttct      180
cggaggctga    tttctgagga    agagtatgag    actctggaga    atgttacaga    tctcctgaag      240
aaaagtcgga    agctgttaat    tttggtacag    aaaaagggag    aggcgacctg    tcagcatttt      300
ctcaagtgtt    tatttagtac    ttttccacag    tcagctgcca    tttgcggctt    aaggcatgaa      360
gttttaaaac    atgagaatac    agtacctcct    caatctatgg    gggcaagcag    taattcagaa      420
gatgcttttt    ctcctggaat    aaaacagcct    gaagcccctg    agatcacagt    gttcttcagt      480
gagaaggaac    acttggattt    ggaaacctct    gagttttca    gggacaagaa    aactagttat       540
agggaaacag    ctttgtctgc    caggaagaat    gagaaggaat    atgacacacc    agaagtcaca      600
ttatcatatt    cagttgagaa    agttggatgt    gaagttccag    caactattac    atatataaaa      660
gatggacaga    gatatgagga    gctagatgat    tctttatact    taggaaaaga    ggaatatcta      720
ggatctgttg    acaccccctga   agatgcagaa    gccactgtgg    aagaggaggt    ttatgatgac      780
ccagagcacg    ttggatatga    tggtgaagag    gacttcgaga    attcagaaac    cacagagttc      840
tctggtgaag    aaccaagtta    tgagggatca    gaaaccagcc    tttcattgga    ggaggaacag      900
gagaaaagta    tagaaggctg    gtctcgaact    catgggctta    gcgatcctc     ccacgttggc      960
ctcccaaagt    gctgggatta    caggcgtgag    ccacccctgcc   tggcctgaaa    attctgcctc     1020
aaacatctca    aacatccatt    tatattttgt    acaagaaagt    aaataaaatt    tttctttta     1080
acattaaaaa    aaaaaaaaaa    aaaaaaa                                                  1107
```

<210> SEQ ID NO 85
<211> LENGTH: 510
<212> TYPE: DNA
<213> ORGANISM: Homo sapien
<220> FEATURE:
<221> NAME/KEY: CDS
<222> LOCATION: (15)...(305)

<400> SEQUENCE: 85

```
aggagagaaa  agcc  atg  gcc  gac  aag  gtc  ctg  aag  gag  aag  aga  aag  ctg           50
                  Met  Ala  Asp  Lys  Val  Leu  Lys  Glu  Lys  Arg  Lys  Leu
                  1                 5                         10 ttt  atc  cat  tcc  atg  ggt  gaa  ggt  aca  ata  aat  ggc  tta  ctg  gat  gaa          98
Phe  Ile  His  Ser  Met  Gly  Glu  Gly  Thr  Ile  Asn  Gly  Leu  Leu  Asp  Glu
         15                      20                       25 tta  tta  cag  aca  agg  gtg  ctg  aac  cag  gaa  gag  atg  gag  aaa  gta  aaa         146
Leu  Leu  Gln  Thr  Arg  Val  Leu  Asn  Gln  Glu  Glu  Met  Glu  Lys  Val  Lys
     30                      35                       40 cgt  gaa  aat  gct  aca  gtt  atg  gat  aag  acc  cga  gct  ttg  att  gac  tcc         194
Arg  Glu  Asn  Ala  Thr  Val  Met  Asp  Lys  Thr  Arg  Ala  Leu  Ile  Asp  Ser
45                   50                       55                       60 gtt  att  ccg  aaa  ggg  gca  cag  gca  tgc  caa  att  tgc  atc  aca  tac  att         242
Val  Ile  Pro  Lys  Gly  Ala  Gln  Ala  Cys  Gln  Ile  Cys  Ile  Thr  Tyr  Ile
              65                       70                       75 tgt  gaa  gaa  gac  agt  tac  ctg  gca  gag  acg  ctg  gga  ctc  tca  gca  ggt         290
Cys  Glu  Glu  Asp  Ser  Tyr  Leu  Ala  Glu  Thr  Leu  Gly  Leu  Ser  Ala  Gly
         80                      85                       90
```

-continued

```
ccg ata cct gga aat tagcttagct tagtacacaa gactcccaat tactattttc    345
Pro Ile Pro Gly Asn
        95 ttccttccca gctcttcagg cagtgcagga caacccagct atgcccacat gctcaagccc    405 agaaggcaga atcaagcttt gctttctaga agacgctcaa aggatatgga aacaaaagtt    465 gcagaggtgc catgttcaga atacaataat aaagtggagt aaaga                   510
```

<210> SEQ ID NO 86
<211> LENGTH: 97
<212> TYPE: PRT
<213> ORGANISM: Homo sapien

<400> SEQUENCE: 86

Met Ala Asp Lys Val Leu Lys Glu Lys Arg Lys Leu Phe Ile His Ser
 1               5                  10                  15

Met Gly Glu Gly Thr Ile Asn Gly Leu Leu Asp Glu Leu Leu Gln Thr
            20                  25                  30

Arg Val Leu Asn Gln Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Glu Thr Leu Gly Leu Ser Ala Gly Pro Ile Pro Gly
                85                  90                  95

Asn

<210> SEQ ID NO 87
<211> LENGTH: 97
<212> TYPE: PRT
<213> ORGANISM: Homo sapien

<400> SEQUENCE: 87

Met Ala Asp Lys Val Leu Lys Glu Lys Arg Lys Leu Phe Ile Arg Ser
 1               5                  10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn

<210> SEQ ID NO 88
<211> LENGTH:
<212> TYPE:
<213> ORGANISM:

<400> SEQUENCE: 88

000

<210> SEQ ID NO 89
<211> LENGTH: 321
<212> TYPE: DNA
<213> ORGANISM: Homo sapien
<220> FEATURE:
<221> NAME/KEY: CDS
<222> LOCATION: (1)...(318)

<400> SEQUENCE: 89

```
atg atc ctc ctg aag aag aga cgg ctg ctt atc aat tca ttg ggt gaa      48
Met Ile Leu Leu Lys Lys Arg Arg Leu Leu Ile Asn Ser Leu Gly Glu
1               5                   10                  15 ggt aca ata aat ggc tta ctg gat gaa tta ttg gag aca aat gtg ctg      96
Gly Thr Ile Asn Gly Leu Leu Asp Glu Leu Leu Glu Thr Asn Val Leu
            20                  25                  30 agc cag gaa gac aca gag ata gta aaa tgt gaa aat gtt aca gtt atc     144
Ser Gln Glu Asp Thr Glu Ile Val Lys Cys Glu Asn Val Thr Val Ile
        35                  40                  45 gat aag gcc cga gat ttg ctt gac tct gtt att cgg aaa ggg gca ggg     192
Asp Lys Ala Arg Asp Leu Leu Asp Ser Val Ile Arg Lys Gly Ala Gly
    50                  55                  60 gca tgt gaa att tgc atc aca tac att tgt gaa gaa gac agg tac ctg     240
Ala Cys Glu Ile Cys Ile Thr Tyr Ile Cys Glu Glu Asp Arg Tyr Leu
65                  70                  75                  80 gca ggg acg ctg gga ctc tca gca gga aat gac tac aga gct gga ggc     288
Ala Gly Thr Leu Gly Leu Ser Ala Gly Asn Asp Tyr Arg Ala Gly Gly
                85                  90                  95 att tgc tca ccg ccc aga gca caa gac ctc tga                         321
Ile Cys Ser Pro Pro Arg Ala Gln Asp Leu
            100                 105
```

<210> SEQ ID NO 90
<211> LENGTH: 106
<212> TYPE: PRT
<213> ORGANISM: Homo sapien

<400> SEQUENCE: 90

```
Met Ile Leu Leu Lys Lys Arg Arg Leu Leu Ile Asn Ser Leu Gly Glu
1               5                   10                  15

Gly Thr Ile Asn Gly Leu Leu Asp Glu Leu Leu Glu Thr Asn Val Leu
            20                  25                  30

Ser Gln Glu Asp Thr Glu Ile Val Lys Cys Glu Asn Val Thr Val Ile
        35                  40                  45

Asp Lys Ala Arg Asp Leu Leu Asp Ser Val Ile Arg Lys Gly Ala Gly
    50                  55                  60

Ala Cys Glu Ile Cys Ile Thr Tyr Ile Cys Glu Glu Asp Arg Tyr Leu
65                  70                  75                  80

Ala Gly Thr Leu Gly Leu Ser Ala Gly Asn Asp Tyr Arg Ala Gly Gly
                85                  90                  95

Ile Cys Ser Pro Pro Arg Ala Gln Asp Leu
            100                 105
```

<210> SEQ ID NO 91
<211> LENGTH: 108
<212> TYPE: PRT
<213> ORGANISM: Homo sapien

<400> SEQUENCE: 91

| | | | | | | | | | | | | | | | |
|---|---|---|---|---|---|---|---|---|---|---|---|---|---|---|---|
| Met | Ala | Asp | Lys | Val | Leu | Leu | Glu | Lys | Arg | Lys | Leu | Leu | Ile | Asn | Ser |
| 1 | | | | 5 | | | | | 10 | | | | | 15 | |

Leu Gly Glu Gly Thr Ile Asn Gly Leu Leu Asp Glu Leu Leu Glu Thr
            20                      25                    30

Asn Val Leu Ser Gln Glu Asp Glu Ile Val Lys Arg Glu Asn Ala Thr
               35                      40                    45

Val Ile Asp Lys Ala Arg Ala Leu Leu Asp Ser Val Ile Arg Lys Gly
     50                   55                    60

Ala Gly Ala Cys Glu Ile Cys Ile Thr Tyr Ile Cys Gly Glu Asp Ser
65                 70                      75                    80

Tyr Leu Ala Gly Thr Leu Gly Leu Ser Ala Gly Asn Ala Val Gln Ala
               85                      90                    95

Gly Gly Ala Cys Ser Thr Ser Ser Gly Gln Asp Leu
            100                    105

<210> SEQ ID NO 92
<211> LENGTH:
<212> TYPE:
<213> ORGANISM:

<400> SEQUENCE: 92

000

<210> SEQ ID NO 93
<211> LENGTH:
<212> TYPE:
<213> ORGANISM:

<400> SEQUENCE: 93

000

<210> SEQ ID NO 94
<211> LENGTH:
<212> TYPE:
<213> ORGANISM:

<400> SEQUENCE: 94

000

<210> SEQ ID NO 95
<211> LENGTH:
<212> TYPE:
<213> ORGANISM:

<400> SEQUENCE: 95

000

<210> SEQ ID NO 96
<211> LENGTH: 3396
<212> TYPE: DNA
<213> ORGANISM: Homo sapien
<220> FEATURE:
<221> NAME/KEY: CDS
<222> LOCATION: (277)...(3348)

<400> SEQUENCE: 96
cgcccgggca ggtgtttata ctccggaggg tgtccccgtg cgtcatcggt ggagtggacc     60
aaaactggtg atctgtttgc cctgtgtgac cttgcccaga accctgctga ctgagagaac   120
acatctgctg gaagtcctct gggattcaag gtacagggaa tgaagagtag ttttacagaa   180

```
aaaagaggac aatattggga tcacctttga cctttccatt tggaaataat attttctatt      240
gtgttataga aaggtgggaa gctttcatcc agaaca atg aat ttc ata aag gac        294
                                         Met Asn Phe Ile Lys Asp
                                          1               5 aat agc cga gcc ctt att caa aga atg gga atg act gtt ata aag caa        342
Asn Ser Arg Ala Leu Ile Gln Arg Met Gly Met Thr Val Ile Lys Gln
            10                  15                  20 atc aca gat gac cta ttt gta tgg aat gtt ctg aat cgc gaa gaa gta        390
Ile Thr Asp Asp Leu Phe Val Trp Asn Val Leu Asn Arg Glu Glu Val
            25                  30                  35 aac atc att tgc tgc gag aag gtg gag cag gat gct gct aga ggg atc        438
Asn Ile Ile Cys Cys Glu Lys Val Glu Gln Asp Ala Ala Arg Gly Ile
    40                  45                  50 att cac atg att ttg aaa aag ggt tca gag tcc tgt aac ctc ttt ctt        486
Ile His Met Ile Leu Lys Lys Gly Ser Glu Ser Cys Asn Leu Phe Leu
55                  60                  65                  70 aaa tcc ctt aag gag tgg aac tat cct cta ttt cag gac ttg aat gga        534
Lys Ser Leu Lys Glu Trp Asn Tyr Pro Leu Phe Gln Asp Leu Asn Gly
                75                  80                  85 caa agt ctt ttt cat cag aca tca gaa gga gac ttg gac gat ttg gct        582
Gln Ser Leu Phe His Gln Thr Ser Glu Gly Asp Leu Asp Asp Leu Ala
            90                  95                  100 cag gat tta aag gac ttg tac cat acc cca tct ttt ctg aac ttt tat        630
Gln Asp Leu Lys Asp Leu Tyr His Thr Pro Ser Phe Leu Asn Phe Tyr
            105                 110                 115 ccc ctt ggt gaa gat att gac att att ttt aac ttg aaa agc acc ttc        678
Pro Leu Gly Glu Asp Ile Asp Ile Ile Phe Asn Leu Lys Ser Thr Phe
120                 125                 130 aca gaa cct atc ctg tgg agg aag gac caa cac cat cac cgc gtg gag        726
Thr Glu Pro Ile Leu Trp Arg Lys Asp Gln His His His Arg Val Glu
135                 140                 145                 150 cag ctg acc ctg aat ggc ctc ctg cag gct ctt cag agc ccc tgc atc        774
Gln Leu Thr Leu Asn Gly Leu Leu Gln Ala Leu Gln Ser Pro Cys Ile
                155                 160                 165 att gaa ggg gaa tct ggc aaa ggc aag tcc act ctg ctg cag cgc att        822
Ile Glu Gly Glu Ser Gly Lys Gly Lys Ser Thr Leu Leu Gln Arg Ile
            170                 175                 180 gcc atg ctc tgg ggc tcc gga aag tgc aag gct ctg acc aag ttc aaa        870
Ala Met Leu Trp Gly Ser Gly Lys Cys Lys Ala Leu Thr Lys Phe Lys
            185                 190                 195 ttc gtc ttc ttc ctc cgt ctc agc agg gcc cag ggt gga ctt ttt gaa        918
Phe Val Phe Phe Leu Arg Leu Ser Arg Ala Gln Gly Gly Leu Phe Glu
200                 205                 210 acc ctc tgt gat caa ctc ctg gat ata cct ggc aca atc agg aag cag        966
Thr Leu Cys Asp Gln Leu Leu Asp Ile Pro Gly Thr Ile Arg Lys Gln
215                 220                 225                 230 aca ttc atg gcc atg ctg ctg aag ctg cgg cag agg gtt ctt ttc ctt        1014
Thr Phe Met Ala Met Leu Leu Lys Leu Arg Gln Arg Val Leu Phe Leu
                235                 240                 245 ctt gat ggc tac aat gaa ttc aag ccc cag aac tgc cca gaa atc gaa        1062
Leu Asp Gly Tyr Asn Glu Phe Lys Pro Gln Asn Cys Pro Glu Ile Glu
            250                 255                 260 gcc ctg ata aag gaa aac cac cgc ttc aag aac atg gtc atc gtc acc        1110
Ala Leu Ile Lys Glu Asn His Arg Phe Lys Asn Met Val Ile Val Thr
            265                 270                 275 act acc act gag tgc ctg agg cac ata cgg cag ttt ggt gcc ctg act        1158
Thr Thr Thr Glu Cys Leu Arg His Ile Arg Gln Phe Gly Ala Leu Thr
280                 285                 290
```

```
gct gag gtg ggg gat atg aca gaa gac agc gcc cag gct ctc atc cga    1206
Ala Glu Val Gly Asp Met Thr Glu Asp Ser Ala Gln Ala Leu Ile Arg
295                 300                 305                 310 gaa gtg ctg atc aag gag ctt gct gaa ggc ttg ttg ctc caa att cag    1254
Glu Val Leu Ile Lys Glu Leu Ala Glu Gly Leu Leu Leu Gln Ile Gln
            315                 320                 325 aaa tcc agg tgc ttg agg aat ctc atg aag acc cct ctc ttt gtg gtc    1302
Lys Ser Arg Cys Leu Arg Asn Leu Met Lys Thr Pro Leu Phe Val Val
                330                 335                 340 atc act tgt gca atc cag atg ggt gaa agt gag ttc cac tct cac aca    1350
Ile Thr Cys Ala Ile Gln Met Gly Glu Ser Glu Phe His Ser His Thr
            345                 350                 355 caa aca acg ctg ttc cat acc ttc tat gat ctg tta ata cag aaa aac    1398
Gln Thr Thr Leu Phe His Thr Phe Tyr Asp Leu Leu Ile Gln Lys Asn
360                 365                 370 aaa cac aaa cat aaa ggt gtg gct gca agt gac ttc att cgg agc ctg    1446
Lys His Lys His Lys Gly Val Ala Ala Ser Asp Phe Ile Arg Ser Leu
375                 380                 385                 390 gac cac cgt gga gac cta gct ctg gag ggt gtg ttc tcc cac aag ttt    1494
Asp His Arg Gly Asp Leu Ala Leu Glu Gly Val Phe Ser His Lys Phe
                395                 400                 405 gat ttc gaa ctg cag gat gtg tcc agc gtg aat gag gat gtc ctg ctg    1542
Asp Phe Glu Leu Gln Asp Val Ser Ser Val Asn Glu Asp Val Leu Leu
            410                 415                 420 aca act ggg ctc ctc tgt aaa tat aca gct caa agg ttc aag cca aag    1590
Thr Thr Gly Leu Leu Cys Lys Tyr Thr Ala Gln Arg Phe Lys Pro Lys
                425                 430                 435 tat aaa ttc ttt cac aag tca ttc cag gag tac aca gca gga cga aga    1638
Tyr Lys Phe Phe His Lys Ser Phe Gln Glu Tyr Thr Ala Gly Arg Arg
440                 445                 450 ctc agc agt tta ttg acg tct cat gag cca gag gag gtg acc aag ggg    1686
Leu Ser Ser Leu Leu Thr Ser His Glu Pro Glu Glu Val Thr Lys Gly
455                 460                 465                 470 aat ggt tac ttg cag aaa atg gtt tcc att tcg gac att aca tcc act    1734
Asn Gly Tyr Leu Gln Lys Met Val Ser Ile Ser Asp Ile Thr Ser Thr
                475                 480                 485 tat agc agc ctg ctc cgg tac acc tgt ggg tca tct gtg gaa gcc acc    1782
Tyr Ser Ser Leu Leu Arg Tyr Thr Cys Gly Ser Ser Val Glu Ala Thr
            490                 495                 500 agg gct gtt atg aag cac ctc gca gca gtg tat caa cac ggc tgc ctt    1830
Arg Ala Val Met Lys His Leu Ala Ala Val Tyr Gln His Gly Cys Leu
                505                 510                 515 ctc gga ctt tcc atc gcc aag agg cct ctc tgg aga cag gaa tct ttg    1878
Leu Gly Leu Ser Ile Ala Lys Arg Pro Leu Trp Arg Gln Glu Ser Leu
520                 525                 530 caa agt gtg aaa aac acc act gag caa gaa att ctg aaa gcc ata aac    1926
Gln Ser Val Lys Asn Thr Thr Glu Gln Glu Ile Leu Lys Ala Ile Asn
535                 540                 545                 550 atc aat tcc ttt gta gag tgt ggc atc cat tta tat caa gag agt aca    1974
Ile Asn Ser Phe Val Glu Cys Gly Ile His Leu Tyr Gln Glu Ser Thr
                555                 560                 565 tcc aaa tca gcc ctg agc caa gaa ttt gaa gct ttc ttt caa ggt aaa    2022
Ser Lys Ser Ala Leu Ser Gln Glu Phe Glu Ala Phe Phe Gln Gly Lys
            570                 575                 580 agc tta tat atc aac tca ggg aac atc ccc gat tac tta ttt gac ttc    2070
Ser Leu Tyr Ile Asn Ser Gly Asn Ile Pro Asp Tyr Leu Phe Asp Phe
                585                 590                 595 ttt gaa cat ttg ccc aat tgt gca agt gcc ctg gac ttc att aaa ctg    2118
Phe Glu His Leu Pro Asn Cys Ala Ser Ala Leu Asp Phe Ile Lys Leu
                600                 605                 610
```

```
gac ttt tat ggg gga gct atg gct tca tgg gaa aag gct gca gaa gac     2166
Asp Phe Tyr Gly Gly Ala Met Ala Ser Trp Glu Lys Ala Ala Glu Asp
615                 620                 625                 630 aca ggt gga atc cac atg gaa gag gcc cca gaa acc tac att ccc agc     2214
Thr Gly Gly Ile His Met Glu Glu Ala Pro Glu Thr Tyr Ile Pro Ser
                635                 640                 645 agg gct gta tct ttg ttc ttc aac tgg aag cag gaa ttc agg act ctg     2262
Arg Ala Val Ser Leu Phe Phe Asn Trp Lys Gln Glu Phe Arg Thr Leu
            650                 655                 660 gag gtc aca ctc cgg gat ttc agc aag ttg aat aag caa gat atc aga     2310
Glu Val Thr Leu Arg Asp Phe Ser Lys Leu Asn Lys Gln Asp Ile Arg
        665                 670                 675 tat ctg ggg aaa ata ttc agc tct gcc aca agc ctc agg ctg caa ata     2358
Tyr Leu Gly Lys Ile Phe Ser Ser Ala Thr Ser Leu Arg Leu Gln Ile
    680                 685                 690 aag aga tgt gct ggt gtg gct gga agc ctc agt ttg gtc ctc agc acc     2406
Lys Arg Cys Ala Gly Val Ala Gly Ser Leu Ser Leu Val Leu Ser Thr
695                 700                 705                 710 tgt aag aac att tat tct ctc atg gtg gaa gcc agt ccc ctc acc ata     2454
Cys Lys Asn Ile Tyr Ser Leu Met Val Glu Ala Ser Pro Leu Thr Ile
                715                 720                 725 gaa gat gag agg cac atc aca tct gta aca aac ctg aaa acc ttg agt     2502
Glu Asp Glu Arg His Ile Thr Ser Val Thr Asn Leu Lys Thr Leu Ser
            730                 735                 740 att cat gac cta cag aat caa cgg ctg ccg ggt ggt ctg act gac agc     2550
Ile His Asp Leu Gln Asn Gln Arg Leu Pro Gly Gly Leu Thr Asp Ser
        745                 750                 755 ttg ggt aac ttg aag aac ctt aca aag ctc ata atg gat aac ata aag     2598
Leu Gly Asn Leu Lys Asn Leu Thr Lys Leu Ile Met Asp Asn Ile Lys
    760                 765                 770 atg aat gaa gaa gat gct ata aaa cta gct gaa ggc ctg aaa aac ctg     2646
Met Asn Glu Glu Asp Ala Ile Lys Leu Ala Glu Gly Leu Lys Asn Leu
775                 780                 785                 790 aag aag atg tgt tta ttt cat ttg acc cac ttg tct gac att gga gag     2694
Lys Lys Met Cys Leu Phe His Leu Thr His Leu Ser Asp Ile Gly Glu
                795                 800                 805 gga atg gat tac ata gtc aag tct ctg tca agt gaa ccc tgt gac ctt     2742
Gly Met Asp Tyr Ile Val Lys Ser Leu Ser Ser Glu Pro Cys Asp Leu
            810                 815                 820 gaa gaa att caa tta gtc tcc tgc tgc ttg tct gca aat gca gtg aaa     2790
Glu Glu Ile Gln Leu Val Ser Cys Cys Leu Ser Ala Asn Ala Val Lys
        825                 830                 835 atc cta gct cag aat ctt cac aat ttg gtc aaa ctg agc att ctt gat     2838
Ile Leu Ala Gln Asn Leu His Asn Leu Val Lys Leu Ser Ile Leu Asp
    840                 845                 850 tta tca gaa aat tac ctg gaa aaa gat gga aat gaa gct ctt cat gaa     2886
Leu Ser Glu Asn Tyr Leu Glu Lys Asp Gly Asn Glu Ala Leu His Glu
855                 860                 865                 870 ctg atc gac agg atg aac gtg cta gaa cag ctc acc gca ctg atg ctg     2934
Leu Ile Asp Arg Met Asn Val Leu Glu Gln Leu Thr Ala Leu Met Leu
                875                 880                 885 ccc tgg ggc tgt gac gtg caa ggc agc ctg agc agc ctg ttg aaa cat     2982
Pro Trp Gly Cys Asp Val Gln Gly Ser Leu Ser Ser Leu Leu Lys His
            890                 895                 900 ttg gag gag gtc cca caa ctc gtc aag ctt ggg ttg aaa aac tgg aga     3030
Leu Glu Glu Val Pro Gln Leu Val Lys Leu Gly Leu Lys Asn Trp Arg
        905                 910                 915 ctc aca gat aca gag att aga att tta ggt gca ttt ttt gga aag aac     3078
Leu Thr Asp Thr Glu Ile Arg Ile Leu Gly Ala Phe Phe Gly Lys Asn
    920                 925                 930
```

```
cct ctg aaa aac ttc cag cag ttg aat ttg gcg gga aat cgt gtg agc     3126
Pro Leu Lys Asn Phe Gln Gln Leu Asn Leu Ala Gly Asn Arg Val Ser
935                 940                 945                 950 agt gat gga tgg ctt gcc ttc atg ggt gta ttt gag aat ctt aag caa     3174
Ser Asp Gly Trp Leu Ala Phe Met Gly Val Phe Glu Asn Leu Lys Gln
            955                 960                 965 tta gtg ttt ttt gac ttt agt act aaa gaa ttt cta cct gat cca gca     3222
Leu Val Phe Phe Asp Phe Ser Thr Lys Glu Phe Leu Pro Asp Pro Ala
        970                 975                 980 tta gtc aga aaa ctt agc caa gtg tta tcc aag tta act ttt ctg caa     3270
Leu Val Arg Lys Leu Ser Gln Val Leu Ser Lys Leu Thr Phe Leu Gln
    985                 990                 995 gaa gct agg ctt gtt ggg tgg caa ttt gat gat gat gat ctc agt gtt     3318
Glu Ala Arg Leu Val Gly Trp Gln Phe Asp Asp Asp Asp Leu Ser Val
1000                1005                1010 att aca ggt gct ttt aaa cta gta act gct taaataaagt gtactcgaag       3368
Ile Thr Gly Ala Phe Lys Leu Val Thr Ala
1015                1020 ccaaaaaaaa aaaaaaaaaa aaaaaaaa                                       3396

<210> SEQ ID NO 97
<211> LENGTH: 1024
<212> TYPE: PRT
<213> ORGANISM: Homo sapien

<400> SEQUENCE: 97

Met Asn Phe Ile Lys Asp Asn Ser Arg Ala Leu Ile Gln Arg Met Gly
 1               5                  10                  15

Met Thr Val Ile Lys Gln Ile Thr Asp Asp Leu Phe Val Trp Asn Val
             20                  25                  30

Leu Asn Arg Glu Glu Val Asn Ile Cys Cys Glu Lys Val Glu Gln
         35                  40                  45

Asp Ala Ala Arg Gly Ile Ile His Met Ile Leu Lys Lys Gly Ser Glu
     50                  55                  60

Ser Cys Asn Leu Phe Leu Lys Ser Leu Lys Glu Trp Asn Tyr Pro Leu
 65                  70                  75                  80

Phe Gln Asp Leu Asn Gly Gln Ser Leu Phe His Gln Thr Ser Glu Gly
                 85                  90                  95

Asp Leu Asp Asp Leu Ala Gln Asp Leu Lys Asp Leu Tyr His Thr Pro
            100                 105                 110

Ser Phe Leu Asn Phe Tyr Pro Leu Gly Glu Asp Ile Asp Ile Ile Phe
        115                 120                 125

Asn Leu Lys Ser Thr Phe Thr Glu Pro Ile Leu Trp Arg Lys Asp Gln
    130                 135                 140

His His His Arg Val Glu Gln Leu Thr Leu Asn Gly Leu Leu Gln Ala
145                 150                 155                 160

Leu Gln Ser Pro Cys Ile Ile Glu Gly Glu Ser Gly Lys Gly Lys Ser
                165                 170                 175

Thr Leu Leu Gln Arg Ile Ala Met Leu Trp Gly Ser Gly Lys Cys Lys
            180                 185                 190

Ala Leu Thr Lys Phe Lys Phe Val Phe Phe Leu Arg Leu Ser Arg Ala
        195                 200                 205

Gln Gly Gly Leu Phe Glu Thr Leu Cys Asp Gln Leu Leu Asp Ile Pro
    210                 215                 220

Gly Thr Ile Arg Lys Gln Thr Phe Met Ala Met Leu Leu Lys Leu Arg
225                 230                 235                 240
```

```
Gln Arg Val Leu Phe Leu Leu Asp Gly Tyr Asn Glu Phe Lys Pro Gln
                245                 250                 255

Asn Cys Pro Glu Ile Glu Ala Leu Ile Lys Glu Asn His Arg Phe Lys
            260                 265                 270

Asn Met Val Ile Val Thr Thr Thr Glu Cys Leu Arg His Ile Arg
        275                 280                 285

Gln Phe Gly Ala Leu Thr Ala Glu Val Gly Asp Met Thr Glu Asp Ser
    290                 295                 300

Ala Gln Ala Leu Ile Arg Glu Val Leu Ile Lys Glu Leu Ala Glu Gly
305                 310                 315                 320

Leu Leu Leu Gln Ile Gln Lys Ser Arg Cys Leu Arg Asn Leu Met Lys
                325                 330                 335

Thr Pro Leu Phe Val Val Ile Thr Cys Ala Ile Gln Met Gly Glu Ser
            340                 345                 350

Glu Phe His Ser His Thr Gln Thr Thr Leu Phe His Thr Phe Tyr Asp
        355                 360                 365

Leu Leu Ile Gln Lys Asn Lys His Lys His Lys Gly Val Ala Ala Ser
    370                 375                 380

Asp Phe Ile Arg Ser Leu Asp His Arg Gly Asp Leu Ala Leu Glu Gly
385                 390                 395                 400

Val Phe Ser His Lys Phe Asp Phe Glu Leu Gln Asp Val Ser Ser Val
                405                 410                 415

Asn Glu Asp Val Leu Leu Thr Thr Gly Leu Leu Cys Lys Tyr Thr Ala
            420                 425                 430

Gln Arg Phe Lys Pro Lys Tyr Lys Phe Phe His Lys Ser Phe Gln Glu
        435                 440                 445

Tyr Thr Ala Gly Arg Arg Leu Ser Ser Leu Leu Thr Ser His Glu Pro
    450                 455                 460

Glu Glu Val Thr Lys Gly Asn Gly Tyr Leu Gln Lys Met Val Ser Ile
465                 470                 475                 480

Ser Asp Ile Thr Ser Thr Tyr Ser Ser Leu Leu Arg Tyr Thr Cys Gly
                485                 490                 495

Ser Ser Val Glu Ala Thr Arg Ala Val Met Lys His Leu Ala Ala Val
            500                 505                 510

Tyr Gln His Gly Cys Leu Leu Gly Leu Ser Ile Ala Lys Arg Pro Leu
        515                 520                 525

Trp Arg Gln Glu Ser Leu Gln Ser Val Lys Asn Thr Thr Glu Gln Glu
    530                 535                 540

Ile Leu Lys Ala Ile Asn Ile Asn Ser Phe Val Glu Cys Gly Ile His
545                 550                 555                 560

Leu Tyr Gln Glu Ser Thr Ser Lys Ser Ala Leu Ser Gln Glu Phe Glu
                565                 570                 575

Ala Phe Phe Gln Gly Lys Ser Leu Tyr Ile Asn Ser Gly Asn Ile Pro
            580                 585                 590

Asp Tyr Leu Phe Asp Phe Phe Glu His Leu Pro Asn Cys Ala Ser Ala
        595                 600                 605

Leu Asp Phe Ile Lys Leu Asp Phe Tyr Gly Gly Ala Met Ala Ser Trp
    610                 615                 620

Glu Lys Ala Ala Glu Asp Thr Gly Gly Ile His Met Glu Glu Ala Pro
625                 630                 635                 640

Glu Thr Tyr Ile Pro Ser Arg Ala Val Ser Leu Phe Phe Asn Trp Lys
                645                 650                 655
```

Gln Glu Phe Arg Thr Leu Glu Val Thr Leu Arg Asp Phe Ser Lys Leu
                660                 665                 670

Asn Lys Gln Asp Ile Arg Tyr Leu Gly Lys Ile Phe Ser Ser Ala Thr
            675                 680                 685

Ser Leu Arg Leu Gln Ile Lys Arg Cys Ala Gly Val Ala Gly Ser Leu
        690                 695                 700

Ser Leu Val Leu Ser Thr Cys Lys Asn Ile Tyr Ser Leu Met Val Glu
705                 710                 715                 720

Ala Ser Pro Leu Thr Ile Glu Asp Glu Arg His Ile Thr Ser Val Thr
                725                 730                 735

Asn Leu Lys Thr Leu Ser Ile His Asp Leu Gln Asn Gln Arg Leu Pro
            740                 745                 750

Gly Gly Leu Thr Asp Ser Leu Gly Asn Leu Lys Asn Leu Thr Lys Leu
        755                 760                 765

Ile Met Asp Asn Ile Lys Met Asn Glu Glu Asp Ala Ile Lys Leu Ala
770                 775                 780

Glu Gly Leu Lys Asn Leu Lys Lys Met Cys Leu Phe His Leu Thr His
785                 790                 795                 800

Leu Ser Asp Ile Gly Glu Gly Met Asp Tyr Ile Val Lys Ser Leu Ser
                805                 810                 815

Ser Glu Pro Cys Asp Leu Glu Glu Ile Gln Leu Val Ser Cys Cys Leu
            820                 825                 830

Ser Ala Asn Ala Val Lys Ile Leu Ala Gln Asn Leu His Asn Leu Val
        835                 840                 845

Lys Leu Ser Ile Leu Asp Leu Ser Glu Asn Tyr Leu Glu Lys Asp Gly
    850                 855                 860

Asn Glu Ala Leu His Glu Leu Ile Asp Arg Met Asn Val Leu Glu Gln
865                 870                 875                 880

Leu Thr Ala Leu Met Leu Pro Trp Gly Cys Asp Val Gln Gly Ser Leu
                885                 890                 895

Ser Ser Leu Leu Lys His Leu Glu Glu Val Pro Gln Leu Val Lys Leu
            900                 905                 910

Gly Leu Lys Asn Trp Arg Leu Thr Asp Thr Glu Ile Arg Ile Leu Gly
        915                 920                 925

Ala Phe Phe Gly Lys Asn Pro Leu Lys Asn Phe Gln Gln Leu Asn Leu
930                 935                 940

Ala Gly Asn Arg Val Ser Ser Asp Gly Trp Leu Ala Phe Met Gly Val
945                 950                 955                 960

Phe Glu Asn Leu Lys Gln Leu Val Phe Phe Asp Phe Ser Thr Lys Glu
                965                 970                 975

Phe Leu Pro Asp Pro Ala Leu Val Arg Lys Leu Ser Gln Val Leu Ser
            980                 985                 990

Lys Leu Thr Phe Leu Gln Glu Ala Arg Leu Val Gly Trp Gln Phe Asp
        995                 1000                1005

Asp Asp Asp Leu Ser Val Ile Thr Gly Ala Phe Lys Leu Val Thr Ala
    1010                1015                1020

<210> SEQ ID NO 98
<211> LENGTH: 1395
<212> TYPE: DNA
<213> ORGANISM: Homo sapien
<220> FEATURE:
<221> NAME/KEY: CDS
<222> LOCATION: (277)...(1353)

<400> SEQUENCE: 98

```
cgcccgggca ggtgtttata ctccggaggg tgtccccgtg cgtcatcggt ggagtggacc      60
aaaactggtg atctgtttgc cctgtgtgac cttgcccaga accctgctga ctgagagaac     120
acatctgctg gaagtcctct gggattcaag gtacagggaa tgaagagtag ttttacagaa     180
aaaagaggac aatattggga tcacctttga cctttccatt tggaataat attttctatt     240 gtgttataga aggtgggaa gctttcatcc agaaca atg aat ttc ata aag gac        294
                                    Met Asn Phe Ile Lys Asp
                                     1               5
```

| | | |
|---|---|---|
| aat agc cga gcc ctt att caa aga atg gga atg act gtt ata aag caa<br>Asn Ser Arg Ala Leu Ile Gln Arg Met Gly Met Thr Val Ile Lys Gln<br>          10                15                20 | | 342 |

```
atc aca gat gac cta ttt gta tgg aat gtt ctg aat cgc gaa gaa gta     390
Ile Thr Asp Asp Leu Phe Val Trp Asn Val Leu Asn Arg Glu Glu Val
         25                  30                  35 aac atc att tgc tgc gag aag gtg gag cag gat gct gct aga ggg atc     438
Asn Ile Ile Cys Cys Glu Lys Val Glu Gln Asp Ala Ala Arg Gly Ile
 40                  45                  50 att cac atg att ttg aaa aag ggt tca gag tcc tgt aac ctc ttt ctt     486
Ile His Met Ile Leu Lys Lys Gly Ser Glu Ser Cys Asn Leu Phe Leu
 55                  60                  65                  70 aaa tcc ctt aag gag tgg aac tat cct cta ttt cag gac ttg aat gga     534
Lys Ser Leu Lys Glu Trp Asn Tyr Pro Leu Phe Gln Asp Leu Asn Gly
             75                  80                  85 caa agt ggt ctg act gac agc ttg ggt aac ttg aag aac ctt aca aag     582
Gln Ser Gly Leu Thr Asp Ser Leu Gly Asn Leu Lys Asn Leu Thr Lys
         90                  95                 100 ctc ata atg gat aac ata aag atg aat gaa gaa gat gct ata aaa cta     630
Leu Ile Met Asp Asn Ile Lys Met Asn Glu Glu Asp Ala Ile Lys Leu
     105                 110                 115 gct gaa ggc ctg aaa aac ctg aag aag atg tgt tta ttt cat ttg acc     678
Ala Glu Gly Leu Lys Asn Leu Lys Lys Met Cys Leu Phe His Leu Thr
120                 125                 130 cac ttg tct gac att gga gag gga atg gat tac ata gtc aag tct ctg     726
His Leu Ser Asp Ile Gly Glu Gly Met Asp Tyr Ile Val Lys Ser Leu
135                 140                 145                 150 tca agt gaa ccc tgt gac ctt gaa gaa att caa tta gtc tcc tgc tgc     774
Ser Ser Glu Pro Cys Asp Leu Glu Glu Ile Gln Leu Val Ser Cys Cys
             155                 160                 165 ttg tct gca aat gca gtg aaa atc cta gct cag aat ctt cac aat ttg     822
Leu Ser Ala Asn Ala Val Lys Ile Leu Ala Gln Asn Leu His Asn Leu
         170                 175                 180 gtc aaa ctg agc att ctt gat tta tca gaa aat tac ctg gaa aaa gat     870
Val Lys Leu Ser Ile Leu Asp Leu Ser Glu Asn Tyr Leu Glu Lys Asp
     185                 190                 195 gga aat gaa gct ctt cat gaa ctg atc gac agg atg aac gtg cta gaa     918
Gly Asn Glu Ala Leu His Glu Leu Ile Asp Arg Met Asn Val Leu Glu
200                 205                 210 cag ctc acc gca ctg atg ctg ccc tgg ggc tgt gac gtg caa ggc agc     966
Gln Leu Thr Ala Leu Met Leu Pro Trp Gly Cys Asp Val Gln Gly Ser
215                 220                 225                 230 ctg agc agc ctg ttg aaa cat ttg gag gag gtc cca caa ctc gtc aag    1014
Leu Ser Ser Leu Leu Lys His Leu Glu Glu Val Pro Gln Leu Val Lys
             235                 240                 245 ctt ggg ttg aaa aac tgg aga ctc aca gat aca gag att aga att tta    1062
Leu Gly Leu Lys Asn Trp Arg Leu Thr Asp Thr Glu Ile Arg Ile Leu
         250                 255                 260
```

```
ggt gca ttt ttt gga aag aac cct ctg aaa aac ttc cag cag ttg aat    1110
Gly Ala Phe Phe Gly Lys Asn Pro Leu Lys Asn Phe Gln Gln Leu Asn
        265                 270                 275 ttg gcg gga aat cgt gtg agc agt gat gga tgg ctt gcc ttc atg ggt    1158
Leu Ala Gly Asn Arg Val Ser Ser Asp Gly Trp Leu Ala Phe Met Gly
    280                 285                 290 gta ttt gag aat ctt aag caa tta gtg ttt ttt gac ttt agt act aaa    1206
Val Phe Glu Asn Leu Lys Gln Leu Val Phe Phe Asp Phe Ser Thr Lys
295                 300                 305                 310 gaa ttt cta cct gat cca gca tta gtc aga aaa ctt agc caa gtg tta    1254
Glu Phe Leu Pro Asp Pro Ala Leu Val Arg Lys Leu Ser Gln Val Leu
                315                 320                 325 tcc aag tta act ttt ctg caa gaa gct agg ctt gtt ggg tgg caa ttt    1302
Ser Lys Leu Thr Phe Leu Gln Glu Ala Arg Leu Val Gly Trp Gln Phe
            330                 335                 340 gat gat gat gat ctc agt gtt att aca ggt gct ttt aaa cta gta act    1350
Asp Asp Asp Asp Leu Ser Val Ile Thr Gly Ala Phe Lys Leu Val Thr
        345                 350                 355 gct taaataaagt gtactcgaag caaaaaaaaa aaaaaaaaa aa                  1395
Ala
```

<210> SEQ ID NO 99
<211> LENGTH: 359
<212> TYPE: PRT
<213> ORGANISM: Homo sapien

<400> SEQUENCE: 99

```
Met Asn Phe Ile Lys Asp Asn Ser Arg Ala Leu Ile Gln Arg Met Gly
1               5                   10                  15

Met Thr Val Ile Lys Gln Ile Thr Asp Asp Leu Phe Val Trp Asn Val
            20                  25                  30

Leu Asn Arg Glu Glu Val Asn Ile Ile Cys Cys Glu Lys Val Glu Gln
        35                  40                  45

Asp Ala Ala Arg Gly Ile Ile His Met Ile Leu Lys Lys Gly Ser Glu
    50                  55                  60

Ser Cys Asn Leu Phe Leu Lys Ser Leu Lys Glu Trp Asn Tyr Pro Leu
65                  70                  75                  80

Phe Gln Asp Leu Asn Gly Gln Ser Gly Leu Thr Asp Ser Leu Gly Asn
                85                  90                  95

Leu Lys Asn Leu Thr Lys Leu Ile Met Asp Asn Ile Lys Met Asn Glu
            100                 105                 110

Glu Asp Ala Ile Lys Leu Ala Glu Gly Leu Lys Asn Leu Lys Lys Met
        115                 120                 125

Cys Leu Phe His Leu Thr His Leu Ser Asp Ile Gly Glu Gly Met Asp
    130                 135                 140

Tyr Ile Val Lys Ser Leu Ser Ser Glu Pro Cys Asp Leu Glu Glu Ile
145                 150                 155                 160

Gln Leu Val Ser Cys Cys Leu Ser Ala Asn Ala Val Lys Ile Leu Ala
                165                 170                 175

Gln Asn Leu His Asn Leu Val Lys Leu Ser Ile Leu Asp Leu Ser Glu
            180                 185                 190

Asn Tyr Leu Glu Lys Asp Gly Asn Glu Ala Leu His Glu Leu Ile Asp
        195                 200                 205

Arg Met Asn Val Leu Glu Gln Leu Thr Ala Leu Met Leu Pro Trp Gly
    210                 215                 220

Cys Asp Val Gln Gly Ser Leu Ser Leu Leu Lys His Leu Glu Glu
225                 230                 235                 240
```

```
Val Pro Gln Leu Val Lys Leu Gly Leu Lys Asn Trp Arg Leu Thr Asp
                245                 250                 255

Thr Glu Ile Arg Ile Leu Gly Ala Phe Phe Gly Lys Asn Pro Leu Lys
            260                 265                 270

Asn Phe Gln Gln Leu Asn Leu Ala Gly Asn Arg Val Ser Ser Asp Gly
                275                 280                 285

Trp Leu Ala Phe Met Gly Val Phe Glu Asn Leu Lys Gln Leu Val Phe
        290                 295                 300

Phe Asp Phe Ser Thr Lys Glu Phe Leu Pro Asp Pro Ala Leu Val Arg
305                 310                 315                 320

Lys Leu Ser Gln Val Leu Ser Lys Leu Thr Phe Leu Gln Glu Ala Arg
                325                 330                 335

Leu Val Gly Trp Gln Phe Asp Asp Asp Leu Ser Val Ile Thr Gly
            340                 345                 350

Ala Phe Lys Leu Val Thr Ala
        355
```

```
<210> SEQ ID NO 100
<211> LENGTH: 578
<212> TYPE: DNA
<213> ORGANISM: Homo sapien
<220> FEATURE:
<221> NAME/KEY: CDS
<222> LOCATION: (277)...(552)

<400> SEQUENCE: 100
```

| | |
|---|---|
| cgcccgggca ggtgtttata ctccggaggg tgtccccgtg cgtcatcggt ggagtggacc | 60 |
| aaaactggtg atctgtttgc cctgtgtgac cttgcccaga accctgctga ctgagagaac | 120 |
| acatctgctg gaagtcctct gggattcaag gtacagggaa tgaagagtag ttttacagaa | 180 |
| aaaagaggac aatattggga tcacctttga cctttccatt tggaaataat attttctatt | 240 |
| gtgttataga aggtgggaa gctttcatcc agaaca atg aat ttc ata aag gac | 294 |

```
                                     Met Asn Phe Ile Lys Asp
                                       1               5
```

| | |
|---|---|
| aat agc cga gcc ctt att caa aga atg gga atg act gtt ata aag caa | 342 |
| Asn Ser Arg Ala Leu Ile Gln Arg Met Gly Met Thr Val Ile Lys Gln | |
|         10                  15                  20 | |
| atc aca gat gac cta ttt gta tgg aat gtt ctg aat cgc gaa gaa gta | 390 |
| Ile Thr Asp Asp Leu Phe Val Trp Asn Val Leu Asn Arg Glu Glu Val | |
|     25                  30                  35 | |
| aac atc att tgc tgc gag aag gtg gag cag gat gct gct aga ggg atc | 438 |
| Asn Ile Ile Cys Cys Glu Lys Val Glu Gln Asp Ala Ala Arg Gly Ile | |
| 40                  45                  50 | |
| att cac atg att ttg aaa aag ggt tca gag tcc tgt aac ctc ttt ctt | 486 |
| Ile His Met Ile Leu Lys Lys Gly Ser Glu Ser Cys Asn Leu Phe Leu | |
| 55                  60                  65                  70 | |
| aaa tcc ctt aag gag tgg aac tat cct cta ttt cag gac ttg aat gga | 534 |
| Lys Ser Leu Lys Glu Trp Asn Tyr Pro Leu Phe Gln Asp Leu Asn Gly | |
|             75                  80                  85 | |
| caa agt ctt tta aca gct tagaaagtac agtagacata ctgggg | 578 |
| Gln Ser Leu Leu Thr Ala | |
|         90 | |

```
<210> SEQ ID NO 101
<211> LENGTH: 92
<212> TYPE: PRT
<213> ORGANISM: Homo sapien
```

<400> SEQUENCE: 101

Met Asn Phe Ile Lys Asp Asn Ser Arg Ala Leu Ile Gln Arg Met Gly
1               5                   10                  15

Met Thr Val Ile Lys Gln Ile Thr Asp Asp Leu Phe Val Trp Asn Val
            20                  25                  30

Leu Asn Arg Glu Glu Val Asn Ile Ile Cys Cys Glu Lys Val Glu Gln
        35                  40                  45

Asp Ala Ala Arg Gly Ile Ile His Met Ile Leu Lys Lys Gly Ser Glu
    50                  55                  60

Ser Cys Asn Leu Phe Leu Lys Ser Leu Lys Glu Trp Asn Tyr Pro Leu
65              70                  75                  80

Phe Gln Asp Leu Asn Gly Gln Ser Leu Leu Thr Ala
                85                  90

<210> SEQ ID NO 102
<211> LENGTH: 768
<212> TYPE: DNA
<213> ORGANISM: Homo sapien
<220> FEATURE:
<221> NAME/KEY: CDS
<222> LOCATION: (277)...(744)

<400> SEQUENCE: 102
cgcccgggca ggtgtttata ctccggaggg tgtccccgtg cgtcatcggt ggagtggacc      60
aaaactggtg atctgtttgc cctgtgtgac cttgcccaga accctgctga ctgagagaac     120
acatctgctg gaagtcctct gggattcaag gtacaggaa tgaagagtag ttttacagaa      180 aaagaggac aatattggga tcacctttga cctttccatt tggaaataat attttctatt     240
gtgttataga aggtgggaa gctttcatcc agaaca atg aat ttc ata aag gac       294
                                          Met Asn Phe Ile Lys Asp
                                          1               5 aat agc cga gcc ctt att caa aga atg gga atg act gtt ata aag caa     342
Asn Ser Arg Ala Leu Ile Gln Arg Met Gly Met Thr Val Ile Lys Gln
            10                  15                  20 atc aca gat gac cta ttt gta tgg aat gtt ctg aat cgc gaa gaa gta     390
Ile Thr Asp Asp Leu Phe Val Trp Asn Val Leu Asn Arg Glu Glu Val
        25                  30                  35 aac atc att tgc tgc gag aag gtg gag cag gat gct gct aga ggg atc     438
Asn Ile Ile Cys Cys Glu Lys Val Glu Gln Asp Ala Ala Arg Gly Ile
    40                  45                  50 att cac atg att ttg aaa aag ggt tca gag tcc tgt aac ctc ttt ctt     486
Ile His Met Ile Leu Lys Lys Gly Ser Glu Ser Cys Asn Leu Phe Leu
55                  60                  65                  70 aaa tcc ctt aag gag tgg aac tat cct cta ttt cag gac ttg aat gga     534
Lys Ser Leu Lys Glu Trp Asn Tyr Pro Leu Phe Gln Asp Leu Asn Gly
                75                  80                  85 caa agt ctt ttt cat cag aca tca gaa gga gac ttg gac gat ttg gct     582
Gln Ser Leu Phe His Gln Thr Ser Glu Gly Asp Leu Asp Asp Leu Ala
            90                  95                  100 cag gat tta aag gac ttg tac cat acc cca tct ttt ctg aac ttt tat     630
Gln Asp Leu Lys Asp Leu Tyr His Thr Pro Ser Phe Leu Asn Phe Tyr
        105                 110                 115 ccc ctt ggt gaa gat att gac att att ttt aac ttg aaa agc acc ttc     678
Pro Leu Gly Glu Asp Ile Asp Ile Ile Phe Asn Leu Lys Ser Thr Phe
    120                 125                 130 aca gaa cct gtc ctg tgg agg aag gac caa cac cat cac cgc gtg gag     726
Thr Glu Pro Val Leu Trp Arg Lys Asp Gln His His His Arg Val Glu
135                 140                 145                 150

```
cag ctg acc cta gtt tta tagcatcttc tacctgcccg ggcg        768
Gln Leu Thr Leu Val Leu
            155
```

<210> SEQ ID NO 103
<211> LENGTH: 156
<212> TYPE: PRT
<213> ORGANISM: Homo sapien

<400> SEQUENCE: 103

```
Met Asn Phe Ile Lys Asp Asn Ser Arg Ala Leu Ile Gln Arg Met Gly
 1               5                  10                  15

Met Thr Val Ile Lys Gln Ile Thr Asp Asp Leu Phe Val Trp Asn Val
             20                  25                  30

Leu Asn Arg Glu Glu Val Asn Ile Ile Cys Cys Glu Lys Val Glu Gln
         35                  40                  45

Asp Ala Ala Arg Gly Ile Ile His Met Ile Leu Lys Lys Gly Ser Glu
     50                  55                  60

Ser Cys Asn Leu Phe Leu Lys Ser Leu Lys Glu Trp Asn Tyr Pro Leu
 65                  70                  75                  80

Phe Gln Asp Leu Asn Gly Gln Ser Leu Phe His Gln Thr Ser Glu Gly
                 85                  90                  95

Asp Leu Asp Asp Leu Ala Gln Asp Leu Lys Asp Leu Tyr His Thr Pro
            100                 105                 110

Ser Phe Leu Asn Phe Tyr Pro Leu Gly Glu Asp Ile Asp Ile Ile Phe
        115                 120                 125

Asn Leu Lys Ser Thr Phe Thr Glu Pro Val Leu Trp Arg Lys Asp Gln
    130                 135                 140

His His His Arg Val Glu Gln Leu Thr Leu Val Leu
145                 150                 155
```

<210> SEQ ID NO 104
<211> LENGTH: 24
<212> TYPE: DNA
<213> ORGANISM: Artificial Sequence
<220> FEATURE:
<223> OTHER INFORMATION: Primer

<400> SEQUENCE: 104

```
aagaagagac ggctgcttat caat                                24
```

<210> SEQ ID NO 105
<211> LENGTH: 24
<212> TYPE: DNA
<213> ORGANISM: Artificial Sequence
<220> FEATURE:
<223> OTHER INFORMATION: Primer

<400> SEQUENCE: 105

```
ccacagcagg cctcgaagat gatc                                24
```

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106

```
atgatcctcc tgaagaagag                                     20
```

-continued

<210> SEQ ID NO 107
<211> LENGTH: 1009
<212> TYPE: PRT
<213> ORGANISM: Homo sapien

<400> SEQUENCE: 107

Cys Glu Met Cys Ser Gln Glu Ala Phe Gln Ala Gln Arg Ser Gln Leu
1               5                   10                  15

Val Glu Leu Leu Val Ser Gly Ser Leu Glu Gly Phe Glu Ser Val Leu
            20                  25                  30

Asp Trp Leu Leu Ser Trp Glu Val Leu Ser Trp Glu Asp Tyr Glu Gly
        35                  40                  45

Phe His Leu Leu Gly Gln Pro Leu Ser His Leu Ala Arg Arg Leu Leu
    50                  55                  60

Asp Thr Val Trp Asn Lys Gly Thr Trp Ala Cys Gln Lys Leu Ile Ala
65                  70                  75                  80

Ala Ala Gln Glu Ala Gln Ala Asp Ser Gln Ser Pro Lys Leu His Gly
                85                  90                  95

Cys Trp Asp Pro His Ser Leu His Pro Ala Arg Asp Leu Gln Ser His
            100                 105                 110

Arg Pro Ala Ile Val Arg Arg Leu His Ser His Val Glu Asn Met Leu
        115                 120                 125

Asp Leu Ala Trp Glu Arg Gly Phe Val Ser Gln Tyr Glu Cys Asp Glu
    130                 135                 140

Ile Arg Leu Pro Ile Phe Thr Pro Ser Gln Arg Ala Arg Arg Leu Leu
145                 150                 155                 160

Asp Leu Ala Thr Val Lys Ala Asn Gly Leu Ala Ala Phe Leu Leu Gln
                165                 170                 175

His Val Gln Glu Leu Pro Val Pro Leu Ala Leu Pro Leu Glu Ala Ala
            180                 185                 190

Thr Cys Lys Lys Tyr Met Ala Lys Leu Arg Thr Thr Val Ser Ala Gln
        195                 200                 205

Ser Arg Phe Leu Ser Thr Tyr Asp Gly Ala Glu Thr Leu Cys Leu Glu
    210                 215                 220

Asp Ile Tyr Thr Glu Asn Val Leu Glu Val Trp Ala Asp Val Gly Met
225                 230                 235                 240

Ala Gly Pro Pro Gln Lys Ser Pro Ala Thr Leu Gly Leu Glu Glu Leu
                245                 250                 255

Phe Ser Thr Pro Gly His Leu Asn Asp Asp Ala Asp Thr Val Leu Val
            260                 265                 270

Val Gly Glu Ala Gly Ser Gly Lys Ser Thr Leu Leu Gln Arg Leu His
        275                 280                 285

Leu Leu Trp Ala Ala Gly Gln Asp Phe Gln Glu Phe Leu Phe Val Phe
    290                 295                 300

Pro Phe Ser Cys Arg Gln Leu Gln Cys Met Ala Lys Pro Leu Ser Val
305                 310                 315                 320

Arg Thr Leu Leu Phe Glu His Cys Cys Trp Pro Asp Val Gly Gln Glu
                325                 330                 335

Asp Ile Phe Gln Leu Leu Leu Asp His Pro Asp Arg Val Leu Leu Thr
            340                 345                 350

Phe Asp Gly Phe Asp Glu Phe Lys Phe Arg Phe Thr Asp Arg Glu Arg
        355                 360                 365

His Cys Ser Pro Thr Asp Pro Thr Ser Val Gln Thr Leu Leu Phe Asn
    370                 375                 380

```
Leu Leu Gln Gly Asn Leu Leu Lys Asn Ala Arg Lys Val Val Thr Ser
385                 390                 395                 400

Arg Pro Ala Ala Val Ser Ala Phe Leu Arg Lys Tyr Ile Arg Thr Glu
                405                 410                 415

Phe Asn Leu Lys Gly Phe Ser Glu Gln Gly Ile Glu Leu Tyr Leu Arg
            420                 425                 430

Lys Arg His His Glu Pro Gly Val Ala Asp Arg Leu Ile Arg Leu Leu
        435                 440                 445

Gln Glu Thr Ser Ala Leu His Gly Leu Cys His Leu Pro Val Phe Ser
    450                 455                 460

Trp Met Val Ser Lys Cys His Gln Glu Leu Leu Leu Gln Glu Gly Gly
465                 470                 475                 480

Ser Pro Lys Thr Thr Asp Met Tyr Leu Leu Ile Leu Gln His Phe
                485                 490                 495

Leu Leu His Ala Thr Pro Pro Asp Ser Ala Ser Gln Gly Leu Gly Pro
            500                 505                 510

Ser Leu Leu Arg Gly Arg Leu Pro Thr Leu Leu His Leu Gly Arg Leu
        515                 520                 525

Ala Leu Trp Gly Leu Gly Met Cys Cys Tyr Val Phe Ser Ala Gln Gln
    530                 535                 540

Leu Gln Ala Ala Gln Val Ser Pro Asp Asp Ile Ser Leu Gly Phe Leu
545                 550                 555                 560

Val Arg Ala Lys Gly Val Val Pro Gly Ser Thr Ala Pro Leu Glu Phe
                565                 570                 575

Leu His Ile Thr Phe Gln Cys Phe Phe Ala Ala Phe Tyr Leu Ala Leu
            580                 585                 590

Ser Ala Asp Val Pro Pro Ala Leu Leu Arg His Leu Phe Asn Cys Gly
        595                 600                 605

Arg Pro Gly Asn Ser Pro Met Ala Arg Leu Leu Pro Thr Met Cys Ile
    610                 615                 620

Gln Ala Ser Glu Gly Lys Asp Ser Ser Val Ala Ala Leu Leu Gln Lys
625                 630                 635                 640

Ala Glu Pro His Asn Leu Gln Ile Thr Ala Ala Phe Leu Ala Gly Leu
                645                 650                 655

Leu Ser Arg Glu His Trp Gly Leu Leu Ala Glu Cys Gln Thr Ser Glu
            660                 665                 670

Lys Ala Leu Leu Arg Arg Gln Ala Cys Ala Arg Trp Cys Leu Ala Arg
        675                 680                 685

Ser Leu Arg Lys His Phe His Ser Ile Pro Pro Ala Ala Pro Gly Glu
    690                 695                 700

Ala Lys Ser Val His Ala Met Pro Gly Phe Ile Trp Leu Ile Arg Ser
705                 710                 715                 720

Leu Tyr Glu Met Gln Glu Glu Arg Leu Ala Arg Lys Ala Ala Arg Gly
                725                 730                 735

Leu Asn Val Gly His Leu Lys Leu Thr Phe Cys Ser Val Gly Pro Thr
            740                 745                 750

Glu Cys Ala Ala Leu Ala Phe Val Leu Gln His Leu Arg Arg Pro Val
        755                 760                 765

Ala Leu Gln Leu Asp Tyr Asn Ser Val Gly Asp Ile Gly Val Glu Gln
    770                 775                 780

Leu Leu Pro Cys Leu Gly Val Cys Lys Ala Leu Tyr Leu Arg Asp Asn
785                 790                 795                 800
```

```
Asn Ile Ser Asp Arg Gly Ile Cys Lys Leu Ile Glu Cys Ala Leu His
                805                 810                 815

Cys Glu Gln Leu Gln Lys Leu Ala Leu Gly Asn Asn Tyr Ile Thr Ala
            820                 825                 830

Ala Gly Ala Gln Val Leu Ala Glu Gly Leu Arg Gly Asn Thr Ser Leu
        835                 840                 845

Gln Phe Leu Gly Phe Trp Gly Asn Arg Val Gly Asp Glu Gly Ala Gln
    850                 855                 860

Ala Leu Ala Glu Ala Leu Gly Asp His Gln Ser Leu Arg Trp Leu Ser
865                 870                 875                 880

Leu Val Gly Asn Asn Ile Gly Ser Val Gly Ala Gln Ala Leu Ala Leu
                885                 890                 895

Met Leu Ala Lys Asn Val Met Leu Glu Glu Leu Cys Leu Glu Glu Asn
            900                 905                 910

His Leu Gln Asp Glu Gly Val Cys Ser Leu Ala Glu Gly Leu Lys Lys
        915                 920                 925

Asn Ser Ser Leu Lys Ile Leu Asn Ile Lys Ile His Ala Ser Gly Phe
    930                 935                 940

Asn Lys Leu Leu Glu Ser Ile Phe Cys Ile Leu Leu Val Val Glu Ala
945                 950                 955                 960

Phe Phe Leu Gln Lys Val Val Lys Ile Leu Glu Glu Met Val Val Ser
                965                 970                 975

Trp Leu Glu Val Arg Leu Ser Asn Asn Cys Ile Thr Tyr Leu Gly Ala
            980                 985                 990

Glu Ala Leu Leu Gln Ala Leu Glu Arg Asn Asp Thr Ile Leu Glu Val
        995                 1000                1005

Trp

<210> SEQ ID NO 108
<211> LENGTH:
<212> TYPE:
<213> ORGANISM:

<400> SEQUENCE: 108

000

<210> SEQ ID NO 109
<211> LENGTH:
<212> TYPE:
<213> ORGANISM:

<400> SEQUENCE: 109

000

<210> SEQ ID NO 110
<211> LENGTH:
<212> TYPE:
<213> ORGANISM:

<400> SEQUENCE: 110

000

<210> SEQ ID NO 111
<211> LENGTH:
<212> TYPE:
<213> ORGANISM:
```

```
<400> SEQUENCE: 111

000

<210> SEQ ID NO 112
<211> LENGTH:
<212> TYPE:
<213> ORGANISM:
<220> FEATURE:
<221> NAME/KEY: VARIANT
<222> LOCATION: (1)...(87)
<223> OTHER INFORMATION: Xaa = Any Amino Acid

<400> SEQUENCE: 112

000

<210> SEQ ID NO 113
<211> LENGTH:
<212> TYPE:
<213> ORGANISM:

<400> SEQUENCE: 113

000

<210> SEQ ID NO 114
<211> LENGTH:
<212> TYPE:
<213> ORGANISM:

<400> SEQUENCE: 114

000

<210> SEQ ID NO 115
<211> LENGTH:
<212> TYPE:
<213> ORGANISM:

<400> SEQUENCE: 115

000

<210> SEQ ID NO 116
<211> LENGTH:
<212> TYPE:
<213> ORGANISM:

<400> SEQUENCE: 116

000

<210> SEQ ID NO 117
<211> LENGTH:
<212> TYPE:
<213> ORGANISM:

<400> SEQUENCE: 117

000

<210> SEQ ID NO 118
<211> LENGTH:
<212> TYPE:
<213> ORGANISM:

<400> SEQUENCE: 118

000
```

```
<210> SEQ ID NO 119
<211> LENGTH:
<212> TYPE:
<213> ORGANISM:

<400> SEQUENCE: 119

000

<210> SEQ ID NO 120
<211> LENGTH:
<212> TYPE:
<213> ORGANISM:

<400> SEQUENCE: 120

000

<210> SEQ ID NO 121
<211> LENGTH:
<212> TYPE:
<213> ORGANISM:

<400> SEQUENCE: 121

000

<210> SEQ ID NO 122
<211> LENGTH:
<212> TYPE:
<213> ORGANISM:

<400> SEQUENCE: 122

000

<210> SEQ ID NO 123
<211> LENGTH:
<212> TYPE:
<213> ORGANISM:

<400> SEQUENCE: 123

000

<210> SEQ ID NO 124
<211> LENGTH:
<212> TYPE:
<213> ORGANISM:

<400> SEQUENCE: 124

000

<210> SEQ ID NO 125
<211> LENGTH:
<212> TYPE:
<213> ORGANISM:

<400> SEQUENCE: 125

000

<210> SEQ ID NO 126
<211> LENGTH:
<212> TYPE:
<213> ORGANISM:

<400> SEQUENCE: 126

000
```

-continued

<210> SEQ ID NO 127
<211> LENGTH:
<212> TYPE:
<213> ORGANISM:

<400> SEQUENCE: 127

000

<210> SEQ ID NO 128
<211> LENGTH:
<212> TYPE:
<213> ORGANISM:

<400> SEQUENCE: 128

000

<210> SEQ ID NO 129
<211> LENGTH:
<212> TYPE:
<213> ORGANISM:

<400> SEQUENCE: 129

000

<210> SEQ ID NO 130
<211> LENGTH:
<212> TYPE:
<213> ORGANISM:

<400> SEQUENCE: 130

000

<210> SEQ ID NO 131
<211> LENGTH:
<212> TYPE:
<213> ORGANISM:

<400> SEQUENCE: 131

000

<210> SEQ ID NO 132
<211> LENGTH:
<212> TYPE:
<213> ORGANISM:

<400> SEQUENCE: 132

000

<210> SEQ ID NO 133
<211> LENGTH:
<212> TYPE:
<213> ORGANISM:

<400> SEQUENCE: 133

000

<210> SEQ ID NO 134
<211> LENGTH:
<212> TYPE:
<213> ORGANISM:

<400> SEQUENCE: 134

000

-continued

```
<210> SEQ ID NO 135
<211> LENGTH:
<212> TYPE:
<213> ORGANISM:

<400> SEQUENCE: 135

000

<210> SEQ ID NO 136
<211> LENGTH:
<212> TYPE:
<213> ORGANISM:

<400> SEQUENCE: 136

000

<210> SEQ ID NO 137
<211> LENGTH:
<212> TYPE:
<213> ORGANISM:

<400> SEQUENCE: 137

000

<210> SEQ ID NO 138
<211> LENGTH:
<212> TYPE:
<213> ORGANISM:

<400> SEQUENCE: 138

000

<210> SEQ ID NO 139
<211> LENGTH:
<212> TYPE:
<213> ORGANISM:

<400> SEQUENCE: 139

000

<210> SEQ ID NO 140
<211> LENGTH:
<212> TYPE:
<213> ORGANISM:

<400> SEQUENCE: 140

000

<210> SEQ ID NO 141
<211> LENGTH:
<212> TYPE:
<213> ORGANISM:

<400> SEQUENCE: 141

000

<210> SEQ ID NO 142
<211> LENGTH:
<212> TYPE:
<213> ORGANISM:

<400> SEQUENCE: 142

000
```

```
<210> SEQ ID NO 143
<211> LENGTH:
<212> TYPE:
<213> ORGANISM:

<400> SEQUENCE: 143

000

<210> SEQ ID NO 144
<211> LENGTH:
<212> TYPE:
<213> ORGANISM:

<400> SEQUENCE: 144

000

<210> SEQ ID NO 145
<211> LENGTH: 30
<212> TYPE: DNA
<213> ORGANISM: Artificial Sequence
<220> FEATURE:
<223> OTHER INFORMATION: primer

<400> SEQUENCE: 145 cagaattca tggccgacaa ggtcctgaag                                30

<210> SEQ ID NO 146
<211> LENGTH: 30
<212> TYPE: DNA
<213> ORGANISM: Artificial Sequence
<220> FEATURE:
<223> OTHER INFORMATION: primer

<400> SEQUENCE: 146 cactcgagc taatttccag gtatcggacc                                30

<210> SEQ ID NO 147
<211> LENGTH: 20
<212> TYPE: DNA
<213> ORGANISM: Artificial Sequence
<220> FEATURE:
<223> OTHER INFORMATION: primer

<400> SEQUENCE: 147
gaagacagtt acctggcaga                                          20

<210> SEQ ID NO 148
<211> LENGTH: 21
<212> TYPE: DNA
<213> ORGANISM: Artificial Sequence
<220> FEATURE:
<223> OTHER INFORMATION: primer

<400> SEQUENCE: 148
ttgtattctg aacatggcac c                                        21

<210> SEQ ID NO 149
<211> LENGTH: 36
<212> TYPE: DNA
<213> ORGANISM: Artificial Sequence
<220> FEATURE:
<223> OTHER INFORMATION: primer

<400> SEQUENCE: 149
gatcatcatc caggccgccc gtggtgacag ccctgg                        36
```

<210> SEQ ID NO 150
<211> LENGTH: 36
<212> TYPE: DNA
<213> ORGANISM: Artificial Sequence
<220> FEATURE:
<223> OTHER INFORMATION: primer

<400> SEQUENCE: 150
ccagggctgt caccacgggc ggcctggatg atgatc                          36

<210> SEQ ID NO 151
<211> LENGTH: 26
<212> TYPE: DNA
<213> ORGANISM: Artificial Sequence
<220> FEATURE:
<223> OTHER INFORMATION: primer

<400> SEQUENCE: 151
cggaattcat ggccgacaag gtcctg                                     26

<210> SEQ ID NO 152
<211> LENGTH: 38
<212> TYPE: DNA
<213> ORGANISM: Artificial Sequence
<220> FEATURE:
<223> OTHER INFORMATION: primer

<400> SEQUENCE: 152
cgctcgagtt agtcttgcat attaaggtaa tttccaga                        38

<210> SEQ ID NO 153
<211> LENGTH: 23
<212> TYPE: DNA
<213> ORGANISM: Artificial Sequence
<220> FEATURE:
<223> OTHER INFORMATION: primer

<400> SEQUENCE: 153
catgtgaatg atccctctag cag                                        23

<210> SEQ ID NO 154
<211> LENGTH: 21
<212> TYPE: DNA
<213> ORGANISM: Artificial Sequence
<220> FEATURE:
<223> OTHER INFORMATION: primer

<400> SEQUENCE: 154
gggctcggct atcgtgctct a                                          21

<210> SEQ ID NO 155
<211> LENGTH: 21
<212> TYPE: DNA
<213> ORGANISM: Artificial Sequence
<220> FEATURE:
<223> OTHER INFORMATION: primer

<400> SEQUENCE: 155
acgatagccg agcccttatt c                                          21

<210> SEQ ID NO 156
<211> LENGTH: 21
<212> TYPE: DNA
<213> ORGANISM: Artificial Sequence
<220> FEATURE:
<223> OTHER INFORMATION: primer

<400> SEQUENCE: 156
gtatggaatg ttctgaatcg c                                              21

<210> SEQ ID NO 157
<211> LENGTH: 33
<212> TYPE: DNA
<213> ORGANISM: Artificial Sequence
<220> FEATURE:
<223> OTHER INFORMATION: primer

<400> SEQUENCE: 157
cccggatcca tgaatttcat aaaggacaat agc                                 33

<210> SEQ ID NO 158
<211> LENGTH: 30
<212> TYPE: DNA
<213> ORGANISM: Artificial Sequence
<220> FEATURE:
<223> OTHER INFORMATION: primer

<400> SEQUENCE: 158
cccttcgaac aagtcctgaa atagaggata                                     30

<210> SEQ ID NO 159
<211> LENGTH: 24
<212> TYPE: DNA
<213> ORGANISM: Artificial Sequence
<220> FEATURE:
<223> OTHER INFORMATION: primer

<400> SEQUENCE: 159
ggtggagcag gatgctgcta gagg                                           24

<210> SEQ ID NO 160
<211> LENGTH: 29
<212> TYPE: DNA
<213> ORGANISM: Artificial Sequence
<220> FEATURE:
<223> OTHER INFORMATION: primer

<400> SEQUENCE: 160
cacagtggtc caggctccga atgaagtca                                      29

<210> SEQ ID NO 161
<211> LENGTH: 25
<212> TYPE: DNA
<213> ORGANISM: Artificial Sequence
<220> FEATURE:
<223> OTHER INFORMATION: primer

<400> SEQUENCE: 161
catcatttgc tgcgagaagg tggag                                          25

<210> SEQ ID NO 162
<211> LENGTH: 25
<212> TYPE: DNA
<213> ORGANISM: Artificial Sequence
<220> FEATURE:
<223> OTHER INFORMATION: primer

<400> SEQUENCE: 162
ttaacttgga taacacttgg ctaag                                          25

```
<210> SEQ ID NO 163
<211> LENGTH: 23
<212> TYPE: DNA
<213> ORGANISM: Artificial Sequence
<220> FEATURE:
<223> OTHER INFORMATION: primer

<400> SEQUENCE: 163
gtaaacatca tttgctgcga gaa                                           23

<210> SEQ ID NO 164
<211> LENGTH: 23
<212> TYPE: DNA
<213> ORGANISM: Artificial Sequence
<220> FEATURE:
<223> OTHER INFORMATION: primer

<400> SEQUENCE: 164
cccgggcagg tagaagatgc tat                                           23

<210> SEQ ID NO 165
<211> LENGTH: 25
<212> TYPE: DNA
<213> ORGANISM: Artificial Sequence
<220> FEATURE:
<223> OTHER INFORMATION: primer

<400> SEQUENCE: 165
aatttcataa aggacaatag ccgag                                         25

<210> SEQ ID NO 166
<211> LENGTH: 25
<212> TYPE: DNA
<213> ORGANISM: Artificial Sequence
<220> FEATURE:
<223> OTHER INFORMATION: primer

<400> SEQUENCE: 166
tgtctactgt actttctaag ctgtt                                         25

<210> SEQ ID NO 167
<211> LENGTH: 225
<212> TYPE: DNA
<213> ORGANISM: Homo sapiens
<220> FEATURE:
<221> NAME/KEY: CDS
<222> LOCATION: (1)...(225)

<400> SEQUENCE: 167 gag agt act ccc tca gag atc ata gaa aga gaa aga aaa aag ttg ctt    48
Glu Ser Thr Pro Ser Glu Ile Ile Glu Arg Glu Arg Lys Lys Leu Leu
  1               5                  10                  15 gaa atc ctt caa cat gat cct gat tct atc tta gac acg tta act tct    96
Glu Ile Leu Gln His Asp Pro Asp Ser Ile Leu Asp Thr Leu Thr Ser
             20                  25                  30 cgg agg ctg att tct gag gaa gag tat gag act ctg gag aat gtt aca   144
Arg Arg Leu Ile Ser Glu Glu Glu Tyr Glu Thr Leu Glu Asn Val Thr
         35                  40                  45 gat ctc ctg aag aaa agt cgg aag ctg tta att ttg gta cag aaa aag   192
Asp Leu Leu Lys Lys Ser Arg Lys Leu Leu Ile Leu Val Gln Lys Lys
     50                  55                  60 gga gag gcg acc tgt cag cat ttt ctc aag tgt                       225
Gly Glu Ala Thr Cys Gln His Phe Leu Lys Cys
 65                  70                  75
```

<210> SEQ ID NO 168
<211> LENGTH: 75
<212> TYPE: PRT
<213> ORGANISM: Homo sapiens

<400> SEQUENCE: 168

Glu Ser Thr Pro Ser Glu Ile Ile Glu Arg Glu Lys Lys Leu Leu
1               5                   10                  15

Glu Ile Leu Gln His Asp Pro Asp Ser Ile Leu Asp Thr Leu Thr Ser
            20                  25                  30

Arg Arg Leu Ile Ser Glu Glu Tyr Glu Thr Leu Glu Asn Val Thr
        35                  40                  45

Asp Leu Leu Lys Lys Ser Arg Lys Leu Leu Ile Leu Val Gln Lys Lys
    50                  55                  60

Gly Glu Ala Thr Cys Gln His Phe Leu Lys Cys
65                  70                  75

<210> SEQ ID NO 169
<211> LENGTH: 228
<212> TYPE: DNA
<213> ORGANISM: Homo sapiens
<220> FEATURE:
<221> NAME/KEY: CDS
<222> LOCATION: (1)...(228)

<400> SEQUENCE: 169 atg tgc tcg cag gag gct ttt cag gca cag agg agc cag ctg gtc gag        48
Met Cys Ser Gln Glu Ala Phe Gln Ala Gln Arg Ser Gln Leu Val Glu
1               5                   10                  15 ctg ctg gtc tca ggg tcc ctg gaa ggc ttc gag agt gtc ctg gac tgg        96
Leu Leu Val Ser Gly Ser Leu Glu Gly Phe Glu Ser Val Leu Asp Trp
            20                  25                  30 ctg ctg tcc tgg gag gtc ctc tcc tgg gag gac tac gag ggc ttc cac        144
Leu Leu Ser Trp Glu Val Leu Ser Trp Glu Asp Tyr Glu Gly Phe His
        35                  40                  45 ctc ctg ggc cag cct ctc tcc cac ttg gcc agg cgc ctt ctg gac acc        192
Leu Leu Gly Gln Pro Leu Ser His Leu Ala Arg Arg Leu Leu Asp Thr
    50                  55                  60 gtc tgg aat aag ggt act tgg gcc tgt cag aag ctc                        228
Val Trp Asn Lys Gly Thr Trp Ala Cys Gln Lys Leu
65                  70                  75

<210> SEQ ID NO 170
<211> LENGTH: 76
<212> TYPE: PRT
<213> ORGANISM: Homo sapiens

<400> SEQUENCE: 170

Met Cys Ser Gln Glu Ala Phe Gln Ala Gln Arg Ser Gln Leu Val Glu
1               5                   10                  15

Leu Leu Val Ser Gly Ser Leu Glu Gly Phe Glu Ser Val Leu Asp Trp
            20                  25                  30

Leu Leu Ser Trp Glu Val Leu Ser Trp Glu Asp Tyr Glu Gly Phe His
        35                  40                  45

Leu Leu Gly Gln Pro Leu Ser His Leu Ala Arg Arg Leu Leu Asp Thr
    50                  55                  60

Val Trp Asn Lys Gly Thr Trp Ala Cys Gln Lys Leu
65                  70                  75

<210> SEQ ID NO 171
<211> LENGTH: 243
<212> TYPE: DNA
<213> ORGANISM: Homo sapiens
<220> FEATURE:
<221> NAME/KEY: CDS
<222> LOCATION: (1)...(243)

<400> SEQUENCE: 171

```
cca gcc cga gac ctg cag agt cac cgg cca gcc att gtc agg agg ctc      48
Pro Ala Arg Asp Leu Gln Ser His Arg Pro Ala Ile Val Arg Arg Leu
 1               5                  10                  15 cac agc cat gtg gag aac atg ctg gac ctg gca tgg gag cgg ggt ttc      96
His Ser His Val Glu Asn Met Leu Asp Leu Ala Trp Glu Arg Gly Phe
             20                  25                  30 gtc agc cag tat gaa tgt gat gaa atc agg ttg ccg atc ttc aca ccg     144
Val Ser Gln Tyr Glu Cys Asp Glu Ile Arg Leu Pro Ile Phe Thr Pro
         35                  40                  45 tcc cag agg gca aga agg ctg ctt gat ctt gcc acg gtg aaa gcg aat     192
Ser Gln Arg Ala Arg Arg Leu Leu Asp Leu Ala Thr Val Lys Ala Asn
     50                  55                  60 gga ttg gct gcc ttc ctt cta caa cat gtt cag gaa tta cca gtc cca     240
Gly Leu Ala Ala Phe Leu Leu Gln His Val Gln Glu Leu Pro Val Pro
 65                  70                  75                  80 ttg                                                                  243
Leu
```

<210> SEQ ID NO 172
<211> LENGTH: 81
<212> TYPE: PRT
<213> ORGANISM: Homo sapiens

<400> SEQUENCE: 172

```
Pro Ala Arg Asp Leu Gln Ser His Arg Pro Ala Ile Val Arg Arg Leu
 1               5                  10                  15

His Ser His Val Glu Asn Met Leu Asp Leu Ala Trp Glu Arg Gly Phe
             20                  25                  30

Val Ser Gln Tyr Glu Cys Asp Glu Ile Arg Leu Pro Ile Phe Thr Pro
         35                  40                  45

Ser Gln Arg Ala Arg Arg Leu Leu Asp Leu Ala Thr Val Lys Ala Asn
     50                  55                  60

Gly Leu Ala Ala Phe Leu Leu Gln His Val Gln Glu Leu Pro Val Pro
 65                  70                  75                  80

Leu
```

<210> SEQ ID NO 173
<211> LENGTH: 888
<212> TYPE: DNA
<213> ORGANISM: Homo sapiens
<220> FEATURE:
<221> NAME/KEY: CDS
<222> LOCATION: (1)...(888)

<400> SEQUENCE: 173

```
gac gat gcg gac act gtg ctg gtg gtg ggt gag gcg ggc agt ggc aag      48
Asp Asp Ala Asp Thr Val Leu Val Val Gly Glu Ala Gly Ser Gly Lys
 1               5                  10                  15 agc acg ctc ctg cag cgg ctg cac ttg ctg tgg gct gca ggg caa gac      96
Ser Thr Leu Leu Gln Arg Leu His Leu Leu Trp Ala Ala Gly Gln Asp
             20                  25                  30
```

| | | |
|---|---|---|
| ttc cag gaa ttt ctc ttt gtc ttc cca ttc agc tgc cgg cag ctg cag<br>Phe Gln Glu Phe Leu Phe Val Phe Pro Phe Ser Cys Arg Gln Leu Gln<br>35                                 40                         45 | 144 | |
| tgc atg gcc aaa cca ctc tct gtg cgg act cta ctc ttt gag cac tgc<br>Cys Met Ala Lys Pro Leu Ser Val Arg Thr Leu Leu Phe Glu His Cys<br>50                                 55                         60 | 192 | |
| tgt tgg cct gat gtt ggt caa gaa gac atc ttc cag tta ctc ctt gac<br>Cys Trp Pro Asp Val Gly Gln Glu Asp Ile Phe Gln Leu Leu Leu Asp<br>65                                70                         75                       80 | 240 | |
| cac cct gac cgt gtc ctg tta acc ttt gat ggc ttt gac gag ttc aag<br>His Pro Asp Arg Val Leu Leu Thr Phe Asp Gly Phe Asp Glu Phe Lys<br>                        85                         90                       95 | 288 | |
| ttc agg ttc acg gat cgt gaa cgc cac tgc tcc ccg acc gac ccc acc<br>Phe Arg Phe Thr Asp Arg Glu Arg His Cys Ser Pro Thr Asp Pro Thr<br>                      100                      105                      110 | 336 | |
| tct gtc cag acc ctg ctc ttc aac ctt ctg cag ggc aac ctg ctg aag<br>Ser Val Gln Thr Leu Leu Phe Asn Leu Leu Gln Gly Asn Leu Leu Lys<br>                      115                      120 | 384 | |
| aat gcc cgc aag gtg gtg acc agc cgt ccg gcc gct gtg tcg gcg ttc<br>Asn Ala Arg Lys Val Val Thr Ser Arg Pro Ala Ala Val Ser Ala Phe<br>130                                135                         140 | 432 | |
| ctc agg aag tac atc cgc acc gag ttc aac ctc aag ggc ttc tct gaa<br>Leu Arg Lys Tyr Ile Arg Thr Glu Phe Asn Leu Lys Gly Phe Ser Glu<br>145                                150                         155                      160 | 480 | |
| cag ggc atc gag ctg tac ctg agg aag cgc cat cat gag ccc ggg gtg<br>Gln Gly Ile Glu Leu Tyr Leu Arg Lys Arg His His Glu Pro Gly Val<br>                      165                      170                      175 | 528 | |
| gcg gac cgc ctc atc cgc ctg ctc caa gag acc tca gcc ctg cac ggt<br>Ala Asp Arg Leu Ile Arg Leu Leu Gln Glu Thr Ser Ala Leu His Gly<br>                      180                      185                      190 | 576 | |
| ttg tgc cac ctg cct gtc ttc tca tgg atg gtg tcc aaa tgc cac cag<br>Leu Cys His Leu Pro Val Phe Ser Trp Met Val Ser Lys Cys His Gln<br>                        195                      200                      205 | 624 | |
| gaa ctg ttg ctg cag gag ggg ggg tcc cca aag acc act aca gat atg<br>Glu Leu Leu Leu Gln Glu Gly Gly Ser Pro Lys Thr Thr Thr Asp Met<br>210                                215                      220 | 672 | |
| tac ctg ctg att ctg cag cat ttt ctg ctg cat gcc acc ccc cca gac<br>Tyr Leu Leu Ile Leu Gln His Phe Leu Leu His Ala Thr Pro Pro Asp<br>225                                230                      235                      240 | 720 | |
| tca gct tcc caa ggt ctg gga ccc agt ctt ctt cgg ggc cgc ctc ccc<br>Ser Ala Ser Gln Gly Leu Gly Pro Ser Leu Leu Arg Gly Arg Leu Pro<br>                      245                      250                      255 | 768 | |
| acc ctc ctg cac ctg ggc aga ctg gct ctg tgg ggc ctg ggc atg tgc<br>Thr Leu Leu His Leu Gly Arg Leu Ala Leu Trp Gly Leu Gly Met Cys<br>                      260                      265                      270 | 816 | |
| tgc tac gtg ttc tca gcc cag cag ctc cag gca gca cag gtc agc cct<br>Cys Tyr Val Phe Ser Ala Gln Gln Leu Gln Ala Ala Gln Val Ser Pro<br>275                                280                      285 | 864 | |
| gat gac att tct ctt ggc ttc ctg<br>Asp Asp Ile Ser Leu Gly Phe Leu<br>290                                295 | 888 | |

<210> SEQ ID NO 174
<211> LENGTH: 296
<212> TYPE: PRT
<213> ORGANISM: Homo sapiens

<400> SEQUENCE: 174

Asp Asp Ala Asp Thr Val Leu Val Val Gly Glu Ala Gly Ser Gly Lys
1               5                   10                  15

Ser Thr Leu Leu Gln Arg Leu His Leu Leu Trp Ala Ala Gly Gln Asp
            20                  25                  30

Phe Gln Glu Phe Leu Phe Val Phe Pro Phe Ser Cys Arg Gln Leu Gln
        35                  40                  45

Cys Met Ala Lys Pro Leu Ser Val Arg Thr Leu Leu Phe Glu His Cys
    50                  55                  60

Cys Trp Pro Asp Val Gly Gln Glu Asp Ile Phe Gln Leu Leu Leu Asp
65                  70                  75                  80

His Pro Asp Arg Val Leu Leu Thr Phe Asp Gly Phe Asp Glu Phe Lys
                85                  90                  95

Phe Arg Phe Thr Asp Arg Glu Arg His Cys Ser Pro Thr Asp Pro Thr
            100                 105                 110

Ser Val Gln Thr Leu Leu Phe Asn Leu Leu Gln Gly Asn Leu Leu Lys
        115                 120                 125

Asn Ala Arg Lys Val Val Thr Ser Arg Pro Ala Ala Val Ser Ala Phe
130                 135                 140

Leu Arg Lys Tyr Ile Arg Thr Glu Phe Asn Leu Lys Gly Phe Ser Glu
145                 150                 155                 160

Gln Gly Ile Glu Leu Tyr Leu Arg Lys Arg His His Glu Pro Gly Val
                165                 170                 175

Ala Asp Arg Leu Ile Arg Leu Leu Gln Glu Thr Ser Ala Leu His Gly
            180                 185                 190

Leu Cys His Leu Pro Val Phe Ser Trp Met Val Ser Lys Cys His Gln
        195                 200                 205

Glu Leu Leu Leu Gln Glu Gly Gly Ser Pro Lys Thr Thr Thr Asp Met
    210                 215                 220

Tyr Leu Leu Ile Leu Gln His Phe Leu Leu His Ala Thr Pro Pro Asp
225                 230                 235                 240

Ser Ala Ser Gln Gly Leu Gly Pro Ser Leu Leu Arg Gly Arg Leu Pro
                245                 250                 255

Thr Leu Leu His Leu Gly Arg Leu Ala Leu Trp Gly Leu Gly Met Cys
            260                 265                 270

Cys Tyr Val Phe Ser Ala Gln Gln Leu Gln Ala Ala Gln Val Ser Pro
        275                 280                 285

Asp Asp Ile Ser Leu Gly Phe Leu
    290                 295

<210> SEQ ID NO 175
<211> LENGTH: 1209
<212> TYPE: DNA
<213> ORGANISM: Homo sapiens
<220> FEATURE:
<221> NAME/KEY: CDS
<222> LOCATION: (1)...(1209)

<400> SEQUENCE: 175 gag ccc ggg gtg gcg gac cgc ctc atc cgc ctg ctc caa gag acc tca       48
Glu Pro Gly Val Ala Asp Arg Leu Ile Arg Leu Leu Gln Glu Thr Ser
1               5                   10                  15 gcc ctg cac ggt ttg tgc cac ctg cct gtc ttc tca tgg atg gtg tcc       96
Ala Leu His Gly Leu Cys His Leu Pro Val Phe Ser Trp Met Val Ser
            20                  25                  30

```
                                        -continued aaa tgc cac cag gaa ctg ttg ctg cag gag ggg ggg tcc cca aag acc       144
Lys Cys His Gln Glu Leu Leu Leu Gln Glu Gly Gly Ser Pro Lys Thr
         35                  40                  45 act aca gat atg tac ctg ctg att ctg cag cat ttt ctg ctg cat gcc       192
Thr Thr Asp Met Tyr Leu Leu Ile Leu Gln His Phe Leu Leu His Ala
     50                  55                  60 acc ccc cca gac tca gct tcc caa ggt ctg gga ccc agt ctt ctt cgg       240
Thr Pro Pro Asp Ser Ala Ser Gln Gly Leu Gly Pro Ser Leu Leu Arg
 65                  70                  75                  80 ggc cgc ctc ccc acc ctc ctg cac ctg gca aga ctg gct ctg tgg ggc       288
Gly Arg Leu Pro Thr Leu Leu His Leu Gly Arg Leu Ala Leu Trp Gly
                 85                  90                  95 ctg ggc atg tgc tgc tac gtg ttc tca gcc cag cag ctc cag gca gca       336
Leu Gly Met Cys Cys Tyr Val Phe Ser Ala Gln Gln Leu Gln Ala Ala
            100                 105                 110 cag gtc agc cct gat gac att tct ctt ggc ttc ctg gtg cgt gcc aaa       384
Gln Val Ser Pro Asp Asp Ile Ser Leu Gly Phe Leu Val Arg Ala Lys
        115                 120                 125 ggt gtc gtg cca ggg agt acg gcg ccc ctg gaa ttc ttc cac atc act       432
Gly Val Val Pro Gly Ser Thr Ala Pro Leu Glu Phe Leu His Ile Thr
    130                 135                 140 ttc cag tgc ttc ttt gcc gcg ttc tac ctg gca ctc agt gct gat gtg       480
Phe Gln Cys Phe Phe Ala Ala Phe Tyr Leu Ala Leu Ser Ala Asp Val
145                 150                 155                 160 cca cca gct ttg ctc aga cac ctc ttc aat tgt ggc agg cca ggc aac       528
Pro Pro Ala Leu Leu Arg His Leu Phe Asn Cys Gly Arg Pro Gly Asn
                165                 170                 175 tca cca atg gcc agg ctc ctg ccc acg atg tgc atc cag gcc tcg gag       576
Ser Pro Met Ala Arg Leu Leu Pro Thr Met Cys Ile Gln Ala Ser Glu
            180                 185                 190 gga aag gac agc agc gtg gca gct ttg ctg cag aag gcc gag ccg cac       624
Gly Lys Asp Ser Ser Val Ala Ala Leu Leu Gln Lys Ala Glu Pro His
        195                 200                 205 aac ctt cag atc aca gca gcc ttc ctg gca ggg ctg ttg tcc cgg gag       672
Asn Leu Gln Ile Thr Ala Ala Phe Leu Ala Gly Leu Leu Ser Arg Glu
    210                 215                 220 cac tgg ggc ctg ctg gct gag tgc cag aca tct gag aag gcc ctg ctc       720
His Trp Gly Leu Leu Ala Glu Cys Gln Thr Ser Glu Lys Ala Leu Leu
225                 230                 235                 240 cgg cgc cag gcc tgt gcc cgc tgg tgt ctg gcc cgc agc ctc cgc aag       768
Arg Arg Gln Ala Cys Ala Arg Trp Cys Leu Ala Arg Ser Leu Arg Lys
                245                 250                 255 cac ttc cac tcc atc ccg cca gct gca ccg ggt gag gcc aag agc gtg       816
His Phe His Ser Ile Pro Pro Ala Ala Pro Gly Glu Ala Lys Ser Val
            260                 265                 270 cat gcc atg ccc ggg ttc atc tgg ctc atc cgg agc ctg tac gag atg       864
His Ala Met Pro Gly Phe Ile Trp Leu Ile Arg Ser Leu Tyr Glu Met
        275                 280                 285 cag gag gag cgg ctg gct cgg aag gct gca cgt ggc ctg aat gtt ggg       912
Gln Glu Glu Arg Leu Ala Arg Lys Ala Ala Arg Gly Leu Asn Val Gly
    290                 295                 300 cac ctc aag ttg aca ttt tgc agt gtg ggc ccc act gag tgt gct gcc       960
His Leu Lys Leu Thr Phe Cys Ser Val Gly Pro Thr Glu Cys Ala Ala
305                 310                 315                 320 ctg gcc ttt gtg ctg cag cac ctc cgg cgg ccc gtg gcc ctg cag ctg      1008
Leu Ala Phe Val Leu Gln His Leu Arg Arg Pro Val Ala Leu Gln Leu
                325                 330                 335 gac tac aac tct gtg ggt gac att ggc gtg gag cag ctg ctg cct tgc      1056
Asp Tyr Asn Ser Val Gly Asp Ile Gly Val Glu Gln Leu Leu Pro Cys
            340                 345                 350
```

-continued

| | | | | | | | | | | | | | | | | |
|---|---|---|---|---|---|---|---|---|---|---|---|---|---|---|---|---|
| ctt | ggt | gtc | tgc | aag | gct | ctg | tat | ttg | cgc | gat | aac | aat | atc | tca | gac | 1104 |
| Leu | Gly | Val | Cys | Lys | Ala | Leu | Tyr | Leu | Arg | Asp | Asn | Asn | Ile | Ser | Asp | |
| | | 355 | | | | 360 | | | | 365 | | | | | | |
| cga | ggc | atc | tgc | aag | ctc | att | gaa | tgt | gct | ctt | cac | tgc | gag | caa | ttg | 1152 |
| Arg | Gly | Ile | Cys | Lys | Leu | Ile | Glu | Cys | Ala | Leu | His | Cys | Glu | Gln | Leu | |
| 370 | | | | | 375 | | | | | 380 | | | | | | |
| cag | aag | tta | gcg | ctg | ggg | aat | aac | tac | atc | act | gcc | gcg | gga | gcc | caa | 1200 |
| Gln | Lys | Leu | Ala | Leu | Gly | Asn | Asn | Tyr | Ile | Thr | Ala | Ala | Gly | Ala | Gln | |
| 385 | | | | | 390 | | | | | 395 | | | | | 400 | |
| gtg | ctg | gcc | | | | | | | | | | | | | | 1209 |
| Val | Leu | Ala | | | | | | | | | | | | | | |

<210> SEQ ID NO 176
<211> LENGTH: 403
<212> TYPE: PRT
<213> ORGANISM: Homo sapiens

<400> SEQUENCE: 176

Glu Pro Gly Val Ala Asp Arg Leu Ile Arg Leu Leu Gln Glu Thr Ser
1               5                   10                  15

Ala Leu His Gly Leu Cys His Leu Pro Val Phe Ser Trp Met Val Ser
            20                  25                  30

Lys Cys His Gln Glu Leu Leu Leu Gln Glu Gly Gly Ser Pro Lys Thr
        35                  40                  45

Thr Thr Asp Met Tyr Leu Leu Ile Leu Gln His Phe Leu Leu His Ala
    50                  55                  60

Thr Pro Pro Asp Ser Ala Ser Gln Gly Leu Gly Pro Ser Leu Leu Arg
65                  70                  75                  80

Gly Arg Leu Pro Thr Leu Leu His Leu Gly Arg Leu Ala Leu Trp Gly
                85                  90                  95

Leu Gly Met Cys Cys Tyr Val Phe Ser Ala Gln Gln Leu Gln Ala Ala
            100                 105                 110

Gln Val Ser Pro Asp Asp Ile Ser Leu Gly Phe Leu Val Arg Ala Lys
        115                 120                 125

Gly Val Val Pro Gly Ser Thr Ala Pro Leu Glu Phe Leu His Ile Thr
    130                 135                 140

Phe Gln Cys Phe Phe Ala Ala Phe Tyr Leu Ala Leu Ser Ala Asp Val
145                 150                 155                 160

Pro Pro Ala Leu Leu Arg His Leu Phe Asn Cys Gly Arg Pro Gly Asn
                165                 170                 175

Ser Pro Met Ala Arg Leu Leu Pro Thr Met Cys Ile Gln Ala Ser Glu
            180                 185                 190

Gly Lys Asp Ser Ser Val Ala Ala Leu Leu Gln Lys Ala Glu Pro His
        195                 200                 205

Asn Leu Gln Ile Thr Ala Ala Phe Leu Ala Gly Leu Leu Ser Arg Glu
    210                 215                 220

His Trp Gly Leu Leu Ala Glu Cys Gln Thr Ser Glu Lys Ala Leu Leu
225                 230                 235                 240

Arg Arg Gln Ala Cys Ala Arg Trp Cys Leu Ala Arg Ser Leu Arg Lys
                245                 250                 255

His Phe His Ser Ile Pro Pro Ala Ala Pro Gly Glu Ala Lys Ser Val
            260                 265                 270

His Ala Met Pro Gly Phe Ile Trp Leu Ile Arg Ser Leu Tyr Glu Met
        275                 280                 285

Gln Glu Glu Arg Leu Ala Arg Lys Ala Ala Arg Gly Leu Asn Val Gly
    290                 295                 300

```
His Leu Lys Leu Thr Phe Cys Ser Val Gly Pro Thr Glu Cys Ala Ala
305                 310                 315                 320

Leu Ala Phe Val Leu Gln His Leu Arg Arg Pro Val Ala Leu Gln Leu
            325                 330                 335

Asp Tyr Asn Ser Val Gly Asp Ile Gly Val Glu Gln Leu Leu Pro Cys
        340                 345                 350

Leu Gly Val Cys Lys Ala Leu Tyr Leu Arg Asp Asn Ile Ser Asp
                355                 360                 365

Arg Gly Ile Cys Lys Leu Ile Glu Cys Ala Leu His Cys Glu Gln Leu
        370                 375                 380

Gln Lys Leu Ala Leu Gly Asn Asn Tyr Ile Thr Ala Ala Gly Ala Gln
385                 390                 395                 400

Val Leu Ala

<210> SEQ ID NO 177
<211> LENGTH: 261
<212> TYPE: DNA
<213> ORGANISM: Homo sapiens
<220> FEATURE:
<221> NAME/KEY: CDS
<222> LOCATION: (1)...(261)

<400> SEQUENCE: 177 atg aat ttc ata aag gac aat agc cga gcc ctt att caa aga atg gga      48
Met Asn Phe Ile Lys Asp Asn Ser Arg Ala Leu Ile Gln Arg Met Gly
1               5                   10                  15 atg act gtt ata aag caa atc aca gat gac cta ttt gta tgg aat gtt      96
Met Thr Val Ile Lys Gln Ile Thr Asp Asp Leu Phe Val Trp Asn Val
            20                  25                  30 ctg aat cgc gaa gaa gta aac atc att tgc tgc gag aag gtg gag cag     144
Leu Asn Arg Glu Glu Val Asn Ile Ile Cys Cys Glu Lys Val Glu Gln
        35                  40                  45 gat gct gct aga ggg atc att cac atg att ttg aaa aag ggt tca gag     192
Asp Ala Ala Arg Gly Ile Ile His Met Ile Leu Lys Lys Gly Ser Glu
    50                  55                  60 tcc tgt aac ctc ttt ctt aaa tcc ctt aag gag tgg aac tat cct cta     240
Ser Cys Asn Leu Phe Leu Lys Ser Leu Lys Glu Trp Asn Tyr Pro Leu
65                  70                  75                  80 ttt cag gac ttg aat gga caa                                          261
Phe Gln Asp Leu Asn Gly Gln
                85

<210> SEQ ID NO 178
<211> LENGTH: 87
<212> TYPE: PRT
<213> ORGANISM: Homo sapiens

<400> SEQUENCE: 178

Met Asn Phe Ile Lys Asp Asn Ser Arg Ala Leu Ile Gln Arg Met Gly
1               5                   10                  15

Met Thr Val Ile Lys Gln Ile Thr Asp Asp Leu Phe Val Trp Asn Val
            20                  25                  30

Leu Asn Arg Glu Glu Val Asn Ile Ile Cys Cys Glu Lys Val Glu Gln
        35                  40                  45

Asp Ala Ala Arg Gly Ile Ile His Met Ile Leu Lys Lys Gly Ser Glu
    50                  55                  60
```

```
Ser Cys Asn Leu Phe Leu Lys Ser Leu Lys Glu Trp Asn Tyr Pro Leu
 65                  70                  75                  80

Phe Gln Asp Leu Asn Gly Gln
                85
```

<210> SEQ ID NO 179
<211> LENGTH: 891
<212> TYPE: DNA
<213> ORGANISM: Homo sapiens
<220> FEATURE:
<221> NAME/KEY: CDS
<222> LOCATION: (1)...(891)

<400> SEQUENCE: 179

```
ctt cag agc ccc tgc atc att gaa ggg gaa tct ggc aaa ggc aag tcc      48
Leu Gln Ser Pro Cys Ile Ile Glu Gly Glu Ser Gly Lys Gly Lys Ser
 1               5                  10                  15 act ctg ctg cag cgc att gcc atg ctc tgg ggc tcc gga aag tgc aag      96
Thr Leu Leu Gln Arg Ile Ala Met Leu Trp Gly Ser Gly Lys Cys Lys
             20                  25                  30 gct ctg acc aag ttc aaa ttc gtc ttc ttc ctc cgt ctc agc agg gcc     144
Ala Leu Thr Lys Phe Lys Phe Val Phe Phe Leu Arg Leu Ser Arg Ala
         35                  40                  45 cag ggt gga ctt ttt gaa acc ctc tgt gat caa ctc ctg gat ata cct     192
Gln Gly Gly Leu Phe Glu Thr Leu Cys Asp Gln Leu Leu Asp Ile Pro
     50                  55                  60 ggc aca atc agg aag cag aca ttc atg gcc atg ctg ctg aag ctg cgg     240
Gly Thr Ile Arg Lys Gln Thr Phe Met Ala Met Leu Leu Lys Leu Arg
 65                  70                  75                  80 cag agg gtt ctt ttc ctt ctt gat ggc tac aat gaa ttc aag ccc cag     288
Gln Arg Val Leu Phe Leu Leu Asp Gly Tyr Asn Glu Phe Lys Pro Gln
                 85                  90                  95 aac tgc cca gaa atc gaa gcc ctg ata aag gaa aac cac cgc ttc aag     336
Asn Cys Pro Glu Ile Glu Ala Leu Ile Lys Glu Asn His Arg Phe Lys
            100                 105                 110 aac atg gtc atc gtc acc act acc act gag tgc ctg agg cac ata cgg     384
Asn Met Val Ile Val Thr Thr Thr Thr Glu Cys Leu Arg His Ile Arg
        115                 120                 125 cag ttt ggt gcc ctg act gct gag gtg ggg gat atg aca gaa gac agc     432
Gln Phe Gly Ala Leu Thr Ala Glu Val Gly Asp Met Thr Glu Asp Ser
    130                 135                 140 gcc cag gct ctc atc cga gaa gtg ctg atc aag gag ctt gct gaa ggc     480
Ala Gln Ala Leu Ile Arg Glu Val Leu Ile Lys Glu Leu Ala Glu Gly
145                 150                 155                 160 ttg ttg ctc caa att cag aaa tcc agg tgc ttg agg aat ctc atg aag     528
Leu Leu Leu Gln Ile Gln Lys Ser Arg Cys Leu Arg Asn Leu Met Lys
                165                 170                 175 acc cct ctc ttt gtg gtc atc act tgt gca atc cag atg ggt gaa agt     576
Thr Pro Leu Phe Val Val Ile Thr Cys Ala Ile Gln Met Gly Glu Ser
            180                 185                 190 gag ttc cac tct cac aca caa aca acg ctg ttc cat acc ttc tat gat     624
Glu Phe His Ser His Thr Gln Thr Thr Leu Phe His Thr Phe Tyr Asp
        195                 200                 205 ctg ttg ata cag aaa aac aaa cac aaa cat aaa ggt gtg gct gca agt     672
Leu Leu Ile Gln Lys Asn Lys His Lys His Lys Gly Val Ala Ala Ser
    210                 215                 220 gac ttc att cgg agc ctg gac cac cgt gga gac cta gct ctg gag ggt     720
Asp Phe Ile Arg Ser Leu Asp His Arg Gly Asp Leu Ala Leu Glu Gly
225                 230                 235                 240
```

```
gtg ttc tcc cac aag ttt gat ttc gaa ctg cag gat gtg tcc agc gtg      768
Val Phe Ser His Lys Phe Asp Phe Glu Leu Gln Asp Val Ser Ser Val
            245                 250                 255 aat gag gat gtc ctg ctg aca act ggg ctc ctc tgt aaa tat aca gct      816
Asn Glu Asp Val Leu Leu Thr Thr Gly Leu Leu Cys Lys Tyr Thr Ala
        260                 265                 270 caa agg ttc aag cca aag tat aaa ttc ttt cac aag tca ttc cag gag      864
Gln Arg Phe Lys Pro Lys Tyr Lys Phe Phe His Lys Ser Phe Gln Glu
    275                 280                 285 tac aca gca gga cga aga ctc agc agt                                  891
Tyr Thr Ala Gly Arg Arg Leu Ser Ser
290                 295
```

<210> SEQ ID NO 180
<211> LENGTH: 297
<212> TYPE: PRT
<213> ORGANISM: Homo sapiens

<400> SEQUENCE: 180

```
Leu Gln Ser Pro Cys Ile Ile Glu Gly Glu Ser Gly Lys Gly Lys Ser
  1               5                  10                  15

Thr Leu Leu Gln Arg Ile Ala Met Leu Trp Gly Ser Gly Lys Cys Lys
             20                  25                  30

Ala Leu Thr Lys Phe Lys Phe Val Phe Phe Leu Arg Leu Ser Arg Ala
         35                  40                  45

Gln Gly Gly Leu Phe Glu Thr Leu Cys Asp Gln Leu Leu Asp Ile Pro
     50                  55                  60

Gly Thr Ile Arg Lys Gln Thr Phe Met Ala Met Leu Leu Lys Leu Arg
 65                  70                  75                  80

Gln Arg Val Leu Phe Leu Leu Asp Gly Tyr Asn Glu Phe Lys Pro Gln
                 85                  90                  95

Asn Cys Pro Glu Ile Glu Ala Leu Ile Lys Glu Asn His Arg Phe Lys
            100                 105                 110

Asn Met Val Ile Val Thr Thr Thr Thr Glu Cys Leu Arg His Ile Arg
        115                 120                 125

Gln Phe Gly Ala Leu Thr Ala Glu Val Gly Asp Met Thr Glu Asp Ser
    130                 135                 140

Ala Gln Ala Leu Ile Arg Glu Val Leu Ile Lys Glu Leu Ala Glu Gly
145                 150                 155                 160

Leu Leu Leu Gln Ile Gln Lys Ser Arg Cys Leu Arg Asn Leu Met Lys
                165                 170                 175

Thr Pro Leu Phe Val Val Ile Thr Cys Ala Ile Gln Met Gly Glu Ser
            180                 185                 190

Glu Phe His Ser His Thr Gln Thr Thr Leu Phe His Thr Phe Tyr Asp
        195                 200                 205

Leu Leu Ile Gln Lys Asn Lys His Lys His Lys Gly Val Ala Ala Ser
    210                 215                 220

Asp Phe Ile Arg Ser Leu Asp His Arg Gly Asp Leu Ala Leu Glu Gly
225                 230                 235                 240

Val Phe Ser His Lys Phe Asp Phe Glu Leu Gln Asp Val Ser Ser Val
                245                 250                 255

Asn Glu Asp Val Leu Leu Thr Thr Gly Leu Leu Cys Lys Tyr Thr Ala
            260                 265                 270
```

```
      Gln Arg Phe Lys Pro Lys Tyr Lys Phe Phe His Lys Ser Phe Gln Glu
              275                 280                 285

Tyr Thr Ala Gly Arg Arg Leu Ser Ser
              290                 295

<210> SEQ ID NO 181
<211> LENGTH: 618
<212> TYPE: DNA
<213> ORGANISM: Homo sapiens
<220> FEATURE:
<221> NAME/KEY: CDS
<222> LOCATION: (1)...(618)

<400> SEQUENCE: 181 ggt aac ttg aag aac ctt aca aag ctc ata atg gat aac ata aag atg          48
Gly Asn Leu Lys Asn Leu Thr Lys Leu Ile Met Asp Asn Ile Lys Met
 1               5                  10                  15 aat gaa gaa gat gct ata aaa cta gct gaa ggc ctg aaa aac ctg aag          96
Asn Glu Glu Asp Ala Ile Lys Leu Ala Glu Gly Leu Lys Asn Leu Lys
             20                  25                  30 aag atg tgt tta ttt cat ttg acc cac ttg tct gac att gga gag gga         144
Lys Met Cys Leu Phe His Leu Thr His Leu Ser Asp Ile Gly Glu Gly
         35                  40                  45 atg gat tac ata gtc aag tct ctg tca agt gaa ccc tgt gac ctt gaa         192
Met Asp Tyr Ile Val Lys Ser Leu Ser Ser Glu Pro Cys Asp Leu Glu
     50                  55                  60 gaa att caa tta gtc tcc tgc tgc ttg tct gca aat gca gtg aaa atc         240
Glu Ile Gln Leu Val Ser Cys Cys Leu Ser Ala Asn Ala Val Lys Ile
 65                  70                  75                  80 cta gct cag aat ctt cac aat ttg gtc aaa ctg agc att ctt gat tta         288
Leu Ala Gln Asn Leu His Asn Leu Val Lys Leu Ser Ile Leu Asp Leu
                 85                  90                  95 tca gaa aat tac ctg gaa aaa gat gga aat gaa gct ctt cat gaa ctg         336
Ser Glu Asn Tyr Leu Glu Lys Asp Gly Asn Glu Ala Leu His Glu Leu
            100                 105                 110 atc gac agg atg aac gtg cta gaa cag ctc acc gca ctg atg ctg ccc         384
Ile Asp Arg Met Asn Val Leu Glu Gln Leu Thr Ala Leu Met Leu Pro
        115                 120                 125 tgg ggc tgt gac gtg caa ggc agc ctg agc agc ctg ttg aaa cat ttg         432
Trp Gly Cys Asp Val Gln Gly Ser Leu Ser Ser Leu Leu Lys His Leu
    130                 135                 140 gag gag gtc cca caa ctc gtc aag ctt ggg ttg aaa aac tgg aga ctc         480
Glu Glu Val Pro Gln Leu Val Lys Leu Gly Leu Lys Asn Trp Arg Leu
145                 150                 155                 160 aca gat aca gag att aga att tta ggt gca ttt ttt gga aag aac cct         528
Thr Asp Thr Glu Ile Arg Ile Leu Gly Ala Phe Phe Gly Lys Asn Pro
                165                 170                 175 ctg aaa aac ttc cag cag ttg aat ttg gcg gga aat cgt gtg agc agt         576
Leu Lys Asn Phe Gln Gln Leu Asn Leu Ala Gly Asn Arg Val Ser Ser
            180                 185                 190 gat gga tgg ctt gcc ttc atg ggt gta ttt gag aat ctt aag                 618
Asp Gly Trp Leu Ala Phe Met Gly Val Phe Glu Asn Leu Lys
        195                 200                 205

<210> SEQ ID NO 182
<211> LENGTH: 206
<212> TYPE: PRT
<213> ORGANISM: Homo sapiens
```

<400> SEQUENCE: 182

Gly Asn Leu Lys Asn Leu Thr Lys Leu Ile Met Asp Asn Ile Lys Met
1               5                   10                  15

Asn Glu Glu Asp Ala Ile Lys Leu Ala Glu Gly Leu Lys Asn Leu Lys
            20                  25                  30

Lys Met Cys Leu Phe His Leu Thr His Leu Ser Asp Ile Gly Glu Gly
        35                  40                  45

Met Asp Tyr Ile Val Lys Ser Leu Ser Ser Glu Pro Cys Asp Leu Glu
    50                  55                  60

Glu Ile Gln Leu Val Ser Cys Cys Leu Ser Ala Asn Ala Val Lys Ile
65                  70                  75                  80

Leu Ala Gln Asn Leu His Asn Leu Val Lys Leu Ser Ile Leu Asp Leu
                85                  90                  95

Ser Glu Asn Tyr Leu Glu Lys Asp Gly Asn Glu Ala Leu His Glu Leu
            100                 105                 110

Ile Asp Arg Met Asn Val Leu Glu Gln Leu Thr Ala Leu Met Leu Pro
        115                 120                 125

Trp Gly Cys Asp Val Gln Gly Ser Leu Ser Ser Leu Leu Lys His Leu
    130                 135                 140

Glu Glu Val Pro Gln Leu Val Lys Leu Gly Leu Lys Asn Trp Arg Leu
145                 150                 155                 160

Thr Asp Thr Glu Ile Arg Ile Leu Gly Ala Phe Phe Gly Lys Asn Pro
                165                 170                 175

Leu Lys Asn Phe Gln Gln Leu Asn Leu Ala Gly Asn Arg Val Ser Ser
            180                 185                 190

Asp Gly Trp Leu Ala Phe Met Gly Val Phe Glu Asn Leu Lys
        195                 200                 205

<210> SEQ ID NO 183
<211> LENGTH: 165
<212> TYPE: DNA
<213> ORGANISM: Homo sapiens
<220> FEATURE:
<221> NAME/KEY: CDS
<222> LOCATION: (1)...(165)

<400> SEQUENCE: 183 acc tac att ccc agc agg gct gta tct ttg ttc ttc aac tgg aag cag        48
Thr Tyr Ile Pro Ser Arg Ala Val Ser Leu Phe Phe Asn Trp Lys Gln
1               5                   10                  15 gaa ttc agg act ctg gag gtc aca ctc cgg gat ttc agc aag ttg aat        96
Glu Phe Arg Thr Leu Glu Val Thr Leu Arg Asp Phe Ser Lys Leu Asn
            20                  25                  30 aag caa gat atc aga tat ctg ggg aaa ata ttc agc tct gcc aca agc       144
Lys Gln Asp Ile Arg Tyr Leu Gly Lys Ile Phe Ser Ser Ala Thr Ser
        35                  40                  45 ctc agg ctg caa ata aag aga                                           165
Leu Arg Leu Gln Ile Lys Arg
    50                  55

<210> SEQ ID NO 184
<211> LENGTH: 55
<212> TYPE: PRT
<213> ORGANISM: Homo sapiens -continued

<400> SEQUENCE: 184

Thr Tyr Ile Pro Ser Arg Ala Val Ser Leu Phe Phe Asn Trp Lys Gln
1               5                   10                  15

Glu Phe Arg Thr Leu Glu Val Thr Leu Arg Asp Phe Ser Lys Leu Asn
                20                  25                  30

Lys Gln Asp Ile Arg Tyr Leu Gly Lys Ile Phe Ser Ser Ala Thr Ser
            35                  40                  45

Leu Arg Leu Gln Ile Lys Arg
    50              55

<210> SEQ ID NO 185
<211> LENGTH: 19
<212> TYPE: DNA
<213> ORGANISM: Artificial Sequence
<220> FEATURE:
<223> OTHER INFORMATION: primer

<400> SEQUENCE: 185
gaaatgtgct cgcaggagg                                                19

<210> SEQ ID NO 186
<211> LENGTH: 20
<212> TYPE: DNA
<213> ORGANISM: Artificial Sequence
<220> FEATURE:
<223> OTHER INFORMATION: primer

<400> SEQUENCE: 186
gatgagcttc tgacaggccc                                               20

<210> SEQ ID NO 187
<211> LENGTH: 3063
<212> TYPE: DNA
<213> ORGANISM: Homo sapiens
<220> FEATURE:
<221> NAME/KEY: CDS
<222> LOCATION: (1)...(2385)
<220> FEATURE:
<221> NAME/KEY: CDS
<222> LOCATION: (2389)...(2928)

<400> SEQUENCE: 187 tgt gaa atg tgc tcg cag gag gct ttt cag gca cag agg agc cag ctg    48
Cys Glu Met Cys Ser Gln Glu Ala Phe Gln Ala Gln Arg Ser Gln Leu
1               5                   10                  15 gtc gag ctg ctg gtc tca ggg tcc ctg gaa ggc ttc gag agt gtc ctg    96
Val Glu Leu Leu Val Ser Gly Ser Leu Glu Gly Phe Glu Ser Val Leu
                20                  25                  30 gac tgg ctg ctg tcc tgg gag gtc ctc tcc tgg gag gac tac gag ggc   144
Asp Trp Leu Leu Ser Trp Glu Val Leu Ser Trp Glu Asp Tyr Glu Gly
            35                  40                  45 ttc cac ctc ctg ggc cag cct ctc tcc cac ttg gcc agg cgc ctt ctg   192
Phe His Leu Leu Gly Gln Pro Leu Ser His Leu Ala Arg Arg Leu Leu
        50                  55                  60 gac acc gtc tgg aat aag ggt act tgg gcc tgt cag aag ctc atc gcg   240
Asp Thr Val Trp Asn Lys Gly Thr Trp Ala Cys Gln Lys Leu Ile Ala
65                  70                  75                  80 gct gcc caa gaa gcc cag gcc gac agc cag tcc ccc aag ctg cat ggc   288
Ala Ala Gln Glu Ala Gln Ala Asp Ser Gln Ser Pro Lys Leu His Gly
                85                  90                  95 tgc tgg gac ccc cac tcg ctc cac cca gcc cga gac ctg cag agt cac   336
Cys Trp Asp Pro His Ser Leu His Pro Ala Arg Asp Leu Gln Ser His
                100                 105                 110

-continued

| | | |
|---|---|---|
| cgg cca gcc att gtc agg agg ctc cac agc cat gtg gag aac atg ctg<br>Arg Pro Ala Ile Val Arg Arg Leu His Ser His Val Glu Asn Met Leu<br>              115                        120                        125 | | 384 |
| gac ctg gca tgg gag cgg ggt ttc gtc agc cag tat gaa tgt gat gaa<br>Asp Leu Ala Trp Glu Arg Gly Phe Val Ser Gln Tyr Glu Cys Asp Glu<br>130                        135                        140 | | 432 |
| atc agg ttg ccg atc ttc aca ccg tcc cag agg gca aga agg ctg ctt<br>Ile Arg Leu Pro Ile Phe Thr Pro Ser Gln Arg Ala Arg Arg Leu Leu<br>145                        150                        155                        160 | | 480 |
| gat ctt gcc acg gtg aaa gcg aat gga ttg gct gcc ttc ctt cta caa<br>Asp Leu Ala Thr Val Lys Ala Asn Gly Leu Ala Ala Phe Leu Leu Gln<br>              165                        170                        175 | | 528 |
| cat gtt cag gaa tta cca gtc cca ttg gcc ctg cct ttg gaa gct gcc<br>His Val Gln Glu Leu Pro Val Pro Leu Ala Leu Pro Leu Glu Ala Ala<br>                  180                        185                        190 | | 576 |
| aca tgc aag aag tat atg gcc aag ctg agg acc acg gtg tct gct cag<br>Thr Cys Lys Lys Tyr Met Ala Lys Leu Arg Thr Thr Val Ser Ala Gln<br>                  195                        200                        205 | | 624 |
| tct cgc ttc ctc agt acc tat gat gga gca gag acg ctc tgc ctg gag<br>Ser Arg Phe Leu Ser Thr Tyr Asp Gly Ala Glu Thr Leu Cys Leu Glu<br>              210                        215                        220 | | 672 |
| gac ata tac aca gag aat gtc ctg gag gtc tgg gca gat gtg ggc atg<br>Asp Ile Tyr Thr Glu Asn Val Leu Glu Val Trp Ala Asp Val Gly Met<br>225                        230                        235                        240 | | 720 |
| gct gga ccc ccg cag aag agc cca gcc acc ctg ggc ctg gag gag ctc<br>Ala Gly Pro Pro Gln Lys Ser Pro Ala Thr Leu Gly Leu Glu Glu Leu<br>                            245                        250                        255 | | 768 |
| ttc agc acc cct ggc cac ctc aat gac gat gcg gac act gtg ctg gtg<br>Phe Ser Thr Pro Gly His Leu Asn Asp Asp Ala Asp Thr Val Leu Val<br>                     260                        265                        270 | | 816 |
| gtg ggt gag gcg ggc agt ggc aag agc acg ctc ctg cag cgg ctg cac<br>Val Gly Glu Ala Gly Ser Gly Lys Ser Thr Leu Leu Gln Arg Leu His<br>                    275                        280                        285 | | 864 |
| ttg ctg tgg gct gca ggg caa gac ttc cag gaa ttt ctc ttt gtc ttc<br>Leu Leu Trp Ala Ala Gly Gln Asp Phe Gln Glu Phe Leu Phe Val Phe<br>              290                        295                        300 | | 912 |
| cca ttc agc tgc cgg cag ctg cag tgc atg gcc aaa cca ctc tct gtg<br>Pro Phe Ser Cys Arg Gln Leu Gln Cys Met Ala Lys Pro Leu Ser Val<br>305                        310                        315                        320 | | 960 |
| cgg act cta ctc ttt gag cac tgc tgt tgg cct gat gtt ggt caa gaa<br>Arg Thr Leu Leu Phe Glu His Cys Cys Trp Pro Asp Val Gly Gln Glu<br>                        325                        330                        335 | | 1008 |
| gac atc ttc cag tta ctc ctt gac cac cct gac cgt gtc ctg tta acc<br>Asp Ile Phe Gln Leu Leu Leu Asp His Pro Asp Arg Val Leu Leu Thr<br>                    340                        345                        350 | | 1056 |
| ttt gat ggc ttt gac gag ttc aag ttc agg ttc acg gat cgt gaa cgc<br>Phe Asp Gly Phe Asp Glu Phe Lys Phe Arg Phe Thr Asp Arg Glu Arg<br>              355                        360                        365 | | 1104 |
| cac tgc tcc ccg acc gac ccc acc tct gtc cag acc ctg ctc ttc aac<br>His Cys Ser Pro Thr Asp Pro Thr Ser Val Gln Thr Leu Leu Phe Asn<br>                  370                        375                        380 | | 1152 |
| ctt ctg cag ggc aac ctg ctg aag aat gcc cgc aag gtg gtg acc agc<br>Leu Leu Gln Gly Asn Leu Leu Lys Asn Ala Arg Lys Val Val Thr Ser<br>385                        390                        395                        400 | | 1200 |
| cgt ccg gcc gct gtg tcg gcg ttc ctc agg aag tac atc cgc acc gag<br>Arg Pro Ala Ala Val Ser Ala Phe Leu Arg Lys Tyr Ile Arg Thr Glu<br>                        405                        410                        415 | | 1248 |
| ttc aac ctc aag ggc ttc tct gaa cag ggc atc gag ctg tac ctg agg<br>Phe Asn Leu Lys Gly Phe Ser Glu Gln Gly Ile Glu Leu Tyr Leu Arg<br>                  420                        425                        430 | | 1296 |

-continued

```
aag cgc cat cat gag ccc ggg gtg gcg gac cgc ctc atc cgc ctg ctc    1344
Lys Arg His His Glu Pro Gly Val Ala Asp Arg Leu Ile Arg Leu Leu
        435                 440                 445 caa gag acc tca gcc ctg cac ggt ttg tgc cac ctg cct gtc ttc tca    1392
Gln Glu Thr Ser Ala Leu His Gly Leu Cys His Leu Pro Val Phe Ser
450                 455                 460 tgg atg gtg tcc aaa tgc cac cag gaa ctg ttg ctg cag gag ggg ggg    1440
Trp Met Val Ser Lys Cys His Gln Glu Leu Leu Leu Gln Glu Gly Gly
465                 470                 475                 480 tcc cca aag acc act aca gat atg tac ctg ctg att ctg cag cat ttt    1488
Ser Pro Lys Thr Thr Thr Asp Met Tyr Leu Leu Ile Leu Gln His Phe
                485                 490                 495 ctg ctg cat gcc acc ccc cca gac tca gct tcc caa ggt ctg gga ccc    1536
Leu Leu His Ala Thr Pro Pro Asp Ser Ala Ser Gln Gly Leu Gly Pro
            500                 505                 510 agt ctt ctt cgg ggc cgc ctc ccc acc ctc ctg cac ctg ggc aga ctg    1584
Ser Leu Leu Arg Gly Arg Leu Pro Thr Leu Leu His Leu Gly Arg Leu
        515                 520                 525 gct ctg tgg ggc ctg ggc atg tgc tgc tac gtg ttc tca gcc cag cag    1632
Ala Leu Trp Gly Leu Gly Met Cys Cys Tyr Val Phe Ser Ala Gln Gln
530                 535                 540 ctc cag gca gca cag gtc agc cct gat gac att tct ctt ggc ttc ctg    1680
Leu Gln Ala Ala Gln Val Ser Pro Asp Asp Ile Ser Leu Gly Phe Leu
545                 550                 555                 560 gtg cgt gcc aaa ggt gtc gtg cca ggg agt acg gcg ccc ctg gaa ttc    1728
Val Arg Ala Lys Gly Val Val Pro Gly Ser Thr Ala Pro Leu Glu Phe
                565                 570                 575 ctt cac atc act ttc cag tgc ttc ttt gcc gcg ttc tac ctg gca ctc    1776
Leu His Ile Thr Phe Gln Cys Phe Phe Ala Ala Phe Tyr Leu Ala Leu
            580                 585                 590 agt gct gat gtg cca cca gct ttg ctc aga cac ctc ttc aat tgt ggc    1824
Ser Ala Asp Val Pro Pro Ala Leu Leu Arg His Leu Phe Asn Cys Gly
        595                 600                 605 agg cca ggc aac tca cca atg gcc agg ctc ctg ccc acg atg tgc atc    1872
Arg Pro Gly Asn Ser Pro Met Ala Arg Leu Leu Pro Thr Met Cys Ile
610                 615                 620 cag gcc tcg gag gga aag gac agc agc gtg gca gct ttg ctg cag aag    1920
Gln Ala Ser Glu Gly Lys Asp Ser Ser Val Ala Ala Leu Leu Gln Lys
625                 630                 635                 640 gcc gag ccg cac aac ctt cag atc aca gca gcc ttc ctg gca ggg ctg    1968
Ala Glu Pro His Asn Leu Gln Ile Thr Ala Ala Phe Leu Ala Gly Leu
                645                 650                 655 ttg tcc cgg gag cac tgg ggc ctg ctg gct gag tgc cag aca tct gag    2016
Leu Ser Arg Glu His Trp Gly Leu Leu Ala Glu Cys Gln Thr Ser Glu
            660                 665                 670 aag gcc ctg ctc cgg cgc cag gcc tgt gcc cgc tgg tgt ctg gcc cgc    2064
Lys Ala Leu Leu Arg Arg Gln Ala Cys Ala Arg Trp Cys Leu Ala Arg
        675                 680                 685 agc ctc cgc aag cac ttc cac tcc atc ccg cca gct gca ccg gtg gag    2112
Ser Leu Arg Lys His Phe His Ser Ile Pro Pro Ala Ala Pro Val Glu
690                 695                 700 gcc aag agc gtg cat gcc atg ccc ggg ttc atc tgg ctc atc cgg agc    2160
Ala Lys Ser Val His Ala Met Pro Gly Phe Ile Trp Leu Ile Arg Ser
705                 710                 715                 720 ctg tac gag atg cag gag gag cgg ctg gct cgg aag gct gca cgt ggc    2208
Leu Tyr Glu Met Gln Glu Glu Arg Leu Ala Arg Lys Ala Ala Arg Gly
                725                 730                 735 ctg aat gtt ggg cac ctc aag ttg aca ttt tgc agt gtg ggc ccc act    2256
Leu Asn Val Gly His Leu Lys Leu Thr Phe Cys Ser Val Gly Pro Thr
            740                 745                 750
```

-continued

| | | |
|---|---|---|
| gag tgt gct gcc ctg gcc ttt gtg ctg cag cac ctc cgg cgg ccc gtg<br>Glu Cys Ala Ala Leu Ala Phe Val Leu Gln His Leu Arg Arg Pro Val<br>755                      760                  765 | | 2304 |
| gcc ctg cag ctg gac tac aac tct gtg ggt gac att ggc gtg gag cag<br>Ala Leu Gln Leu Asp Tyr Asn Ser Val Gly Asp Ile Gly Val Glu Gln<br>770                      775                  780 | | 2352 |
| ctg ctg cct tgc ctt ggt gtc tgc aag gct ctg taa ttc tgg ggc aac<br>Leu Leu Pro Cys Leu Gly Val Cys Lys Ala Leu     Phe Trp Gly Asn<br>785                      790                  795 | | 2400 |
| aga gtg ggt gac gag ggg gcc cag gcc ctg gct gaa gcc ttg ggt gat<br>Arg Val Gly Asp Glu Gly Ala Gln Ala Leu Ala Glu Ala Leu Gly Asp<br>800                      805                  810                  815 | | 2448 |
| cac cag agc ttg agg tgg ctc agc ctg gtg ggg aac aac att ggc agt<br>His Gln Ser Leu Arg Trp Leu Ser Leu Val Gly Asn Asn Ile Gly Ser<br>                    820                  825                  830 | | 2496 |
| gtg ggt gcc caa gcc ttg gca ctg atg ctg gca aag aac gtc atg cta<br>Val Gly Ala Gln Ala Leu Ala Leu Met Leu Ala Lys Asn Val Met Leu<br>835                      840                  845 | | 2544 |
| gaa gaa ctc tgc ctg gag gag aac cat ctc cag gat gaa ggt gta tgt<br>Glu Glu Leu Cys Leu Glu Glu Asn His Leu Gln Asp Glu Gly Val Cys<br>850                      855                  860 | | 2592 |
| tct ctc gca gaa gga ctg aag aaa aat tca agt ttg aaa atc ctg aac<br>Ser Leu Ala Glu Gly Leu Lys Lys Asn Ser Ser Leu Lys Ile Leu Asn<br>865                      870                  875 | | 2640 |
| ata aaa att cat gct tcg gga ttc aac aaa ctc ttg gaa agc att ttc<br>Ile Lys Ile His Ala Ser Gly Phe Asn Lys Leu Leu Glu Ser Ile Phe<br>880                      885                  890                  895 | | 2688 |
| tgc atc ctc ctg gtt gtg gaa gca ttt ttc ctg cag aaa gtt gtc aag<br>Cys Ile Leu Leu Val Val Glu Ala Phe Phe Leu Gln Lys Val Val Lys<br>                    900                  905                  910 | | 2736 |
| att ctt gaa gaa atg gta gtc agt tgg cta gag gtc agg ttg tcc aat<br>Ile Leu Glu Glu Met Val Val Ser Trp Leu Glu Val Arg Leu Ser Asn<br>915                      920                  925 | | 2784 |
| aac tgc atc acc tac cta ggg gca gaa gcc ctc ctg cag gcc ctt gaa<br>Asn Cys Ile Thr Tyr Leu Gly Ala Glu Ala Leu Leu Gln Ala Leu Glu<br>                    930                  935                  940 | | 2832 |
| agg aat gac acc atc ctg gaa gtc tgg ctc cga ggg aac act ttc tct<br>Arg Asn Asp Thr Ile Leu Glu Val Trp Leu Arg Gly Asn Thr Phe Ser<br>945                      950                  955 | | 2880 |
| cta gag gag gtt gac aag ctc ggc tgc agg gac acc aga ctc ttg ctt<br>Leu Glu Glu Val Asp Lys Leu Gly Cys Arg Asp Thr Arg Leu Leu Leu<br>960                      965                  970                  975 | | 2928 |
| tgaagtctcc gggaggatgt tcgtctcagt ttgtttgtga gcaggctgtg agtttgggcc | | 2988 |
| ccagaggctg ggtgacatgt gttggcagcc tcttcaaaat gagccctgtc ctgcctaagg | | 3048 |
| ctgaacttgt tttct | | 3063 |

<210> SEQ ID NO 188
<211> LENGTH: 795
<212> TYPE: PRT
<213> ORGANISM: Homo sapiens

<400> SEQUENCE: 188

Cys Glu Met Cys Ser Gln Glu Ala Phe Gln Ala Gln Arg Ser Gln Leu
1               5                    10                   15

Val Glu Leu Leu Val Ser Gly Ser Leu Glu Gly Phe Glu Ser Val Leu
                  20                   25                 30

Asp Trp Leu Leu Ser Trp Glu Val Leu Ser Trp Glu Asp Tyr Glu Gly
        35                  40                   45

-continued

```
Phe His Leu Leu Gly Gln Pro Leu Ser His Leu Ala Arg Arg Leu Leu
 50                  55                  60

Asp Thr Val Trp Asn Lys Gly Thr Trp Ala Cys Gln Lys Leu Ile Ala
 65                  70                  75                  80

Ala Ala Gln Glu Ala Gln Ala Asp Ser Gln Ser Pro Lys Leu His Gly
                 85                  90                  95

Cys Trp Asp Pro His Ser Leu His Pro Ala Arg Asp Leu Gln Ser His
            100                 105                 110

Arg Pro Ala Ile Val Arg Arg Leu His Ser His Val Glu Asn Met Leu
        115                 120                 125

Asp Leu Ala Trp Glu Arg Gly Phe Val Ser Gln Tyr Glu Cys Asp Glu
    130                 135                 140

Ile Arg Leu Pro Ile Phe Thr Pro Ser Gln Arg Ala Arg Arg Leu Leu
145                 150                 155                 160

Asp Leu Ala Thr Val Lys Ala Asn Gly Leu Ala Ala Phe Leu Leu Gln
                165                 170                 175

His Val Gln Glu Leu Pro Val Pro Leu Ala Leu Pro Leu Glu Ala Ala
            180                 185                 190

Thr Cys Lys Lys Tyr Met Ala Lys Leu Arg Thr Thr Val Ser Ala Gln
        195                 200                 205

Ser Arg Phe Leu Ser Thr Tyr Asp Gly Ala Glu Thr Leu Cys Leu Glu
    210                 215                 220

Asp Ile Tyr Thr Glu Asn Val Leu Glu Val Trp Ala Asp Val Gly Met
225                 230                 235                 240

Ala Gly Pro Pro Gln Lys Ser Pro Ala Thr Leu Gly Leu Glu Glu Leu
                245                 250                 255

Phe Ser Thr Pro Gly His Leu Asn Asp Asp Ala Asp Thr Val Leu Val
            260                 265                 270

Val Gly Glu Ala Gly Ser Gly Lys Ser Thr Leu Leu Gln Arg Leu His
        275                 280                 285

Leu Leu Trp Ala Ala Gly Gln Asp Phe Gln Glu Phe Leu Phe Val Phe
    290                 295                 300

Pro Phe Ser Cys Arg Gln Leu Gln Cys Met Ala Lys Pro Leu Ser Val
305                 310                 315                 320

Arg Thr Leu Leu Phe Glu His Cys Cys Trp Pro Asp Val Gly Gln Glu
                325                 330                 335

Asp Ile Phe Gln Leu Leu Leu Asp His Pro Asp Arg Val Leu Leu Thr
            340                 345                 350

Phe Asp Gly Phe Asp Glu Phe Lys Phe Arg Phe Thr Asp Arg Glu Arg
        355                 360                 365

His Cys Ser Pro Thr Asp Pro Thr Ser Val Gln Thr Leu Leu Phe Asn
    370                 375                 380

Leu Leu Gln Gly Asn Leu Leu Lys Asn Ala Arg Lys Val Val Thr Ser
385                 390                 395                 400

Arg Pro Ala Ala Val Ser Ala Phe Leu Arg Lys Tyr Ile Arg Thr Glu
                405                 410                 415

Phe Asn Leu Lys Gly Phe Ser Glu Gln Gly Ile Glu Leu Tyr Leu Arg
            420                 425                 430

Lys Arg His His Glu Pro Gly Val Ala Asp Arg Leu Ile Arg Leu Leu
        435                 440                 445

Gln Glu Thr Ser Ala Leu His Gly Leu Cys His Leu Pro Val Phe Ser
    450                 455                 460
```

```
Trp Met Val Ser Lys Cys His Gln Glu Leu Leu Leu Gln Glu Gly Gly
465                 470                 475                 480

Ser Pro Lys Thr Thr Thr Asp Met Tyr Leu Leu Ile Leu Gln His Phe
                485                 490                 495

Leu Leu His Ala Thr Pro Pro Asp Ser Ala Ser Gln Gly Leu Gly Pro
            500                 505                 510

Ser Leu Leu Arg Gly Arg Leu Pro Thr Leu Leu His Leu Gly Arg Leu
        515                 520                 525

Ala Leu Trp Gly Leu Gly Met Cys Cys Tyr Val Phe Ser Ala Gln Gln
    530                 535                 540

Leu Gln Ala Ala Gln Val Ser Pro Asp Asp Ile Ser Leu Gly Phe Leu
545                 550                 555                 560

Val Arg Ala Lys Gly Val Val Pro Gly Ser Thr Ala Pro Leu Glu Phe
                565                 570                 575

Leu His Ile Thr Phe Gln Cys Phe Phe Ala Ala Phe Tyr Leu Ala Leu
            580                 585                 590

Ser Ala Asp Val Pro Pro Ala Leu Leu Arg His Leu Phe Asn Cys Gly
        595                 600                 605

Arg Pro Gly Asn Ser Pro Met Ala Arg Leu Leu Pro Thr Met Cys Ile
    610                 615                 620

Gln Ala Ser Glu Gly Lys Asp Ser Ser Val Ala Ala Leu Leu Gln Lys
625                 630                 635                 640

Ala Glu Pro His Asn Leu Gln Ile Thr Ala Ala Phe Leu Ala Gly Leu
                645                 650                 655

Leu Ser Arg Glu His Trp Gly Leu Leu Ala Glu Cys Gln Thr Ser Glu
            660                 665                 670

Lys Ala Leu Leu Arg Arg Gln Ala Cys Ala Arg Trp Cys Leu Ala Arg
        675                 680                 685

Ser Leu Arg Lys His Phe His Ser Ile Pro Pro Ala Ala Pro Gly Glu
    690                 695                 700

Ala Lys Ser Val His Ala Met Pro Gly Phe Ile Trp Leu Ile Arg Ser
705                 710                 715                 720

Leu Tyr Glu Met Gln Glu Glu Arg Leu Ala Arg Lys Ala Ala Arg Gly
                725                 730                 735

Leu Asn Val Gly His Leu Lys Leu Thr Phe Cys Ser Val Gly Pro Thr
            740                 745                 750

Glu Cys Ala Ala Leu Ala Phe Val Leu Gln His Leu Arg Arg Pro Val
        755                 760                 765

Ala Leu Gln Leu Asp Tyr Asn Ser Val Gly Asp Ile Gly Val Glu Gln
    770                 775                 780

Leu Leu Pro Cys Leu Gly Val Cys Lys Ala Leu
785                 790                 795

<210> SEQ ID NO 189
<211> LENGTH: 180
<212> TYPE: PRT
<213> ORGANISM: Homo sapiens

<400> SEQUENCE: 189

Phe Trp Gly Asn Arg Val Gly Asp Glu Gly Ala Gln Ala Leu Ala Glu
1               5                   10                  15

Ala Leu Gly Asp His Gln Ser Leu Arg Trp Leu Ser Leu Val Gly Asn
            20                  25                  30

Asn Ile Gly Ser Val Gly Ala Gln Ala Leu Ala Leu Met Leu Ala Lys
        35                  40                  45
```

```
Asn Val Met Leu Glu Glu Leu Cys Leu Glu Glu Asn His Leu Gln Asp
 50                  55                  60

Glu Gly Val Cys Ser Leu Ala Glu Gly Leu Lys Lys Asn Ser Ser Leu
 65                  70                  75                  80

Lys Ile Leu Asn Ile Lys Ile His Ala Ser Gly Phe Asn Lys Leu Leu
                 85                  90                  95

Glu Ser Ile Phe Cys Ile Leu Leu Val Val Glu Ala Phe Phe Leu Gln
            100                 105                 110

Lys Val Val Lys Ile Leu Glu Glu Met Val Val Ser Trp Leu Glu Val
        115                 120                 125

Arg Leu Ser Asn Asn Cys Ile Thr Tyr Leu Gly Ala Glu Ala Leu Leu
130                 135                 140

Gln Ala Leu Glu Arg Asn Asp Thr Ile Leu Glu Val Trp Leu Arg Gly
145                 150                 155                 160

Asn Thr Phe Ser Leu Glu Glu Val Asp Lys Leu Gly Cys Arg Asp Thr
                165                 170                 175

Arg Leu Leu Leu
            180

<210> SEQ ID NO 190
<211> LENGTH: 721
<212> TYPE: DNA
<213> ORGANISM: Mus musculus
<220> FEATURE:
<221> NAME/KEY: CDS
<222> LOCATION: (193)...(612)

<400> SEQUENCE: 190
cctggggttc ctgcacatta ccttccgtgc tttttgccg ctttctactt ggctgtcagt      60
gctgacacat cggtggcctc tctcaagcac cttttcagct gtggccggct gggcagctca     120
ctgctgggaa ggctgctgcc caacctgtgt atccagggct ccagagtcaa gaagggcagc     180
gaagcagccc tg ctg cag aag gct gag cca cac aac ctg caa atc aca gca    231
              Leu Gln Lys Ala Glu Pro His Asn Leu Gln Ile Thr Ala
                1               5                  10 gcc ttc cta gca ggt ctg ttg tcc cag cag cat cgg gac ctg ttg gct      279
Ala Phe Leu Ala Gly Leu Leu Ser Gln Gln His Arg Asp Leu Leu Ala
 15                  20                  25 gca tgc cag gtc tcc gag agg gta ctg ctc cag cgt cag gca cgt gcc      327
Ala Cys Gln Val Ser Glu Arg Val Leu Leu Gln Arg Gln Ala Arg Ala
 30                  35                  40                  45 cgc tcg tgt ctg gcc cac agc ctc cgc gag cac ttc cat tcc atc ccg      375
Arg Ser Cys Leu Ala His Ser Leu Arg Glu His Phe His Ser Ile Pro
                 50                  55                  60 cct gcc gtg ccc ggt gag acc aag agc atg cat gct atg ccg ggc ttc      423
Pro Ala Val Pro Gly Glu Thr Lys Ser Met His Ala Met Pro Gly Phe
             65                  70                  75 att tgg ctc atc cgt agc ctg tac gag atg cag gag gag cag ttg gcc      471
Ile Trp Leu Ile Arg Ser Leu Tyr Glu Met Gln Glu Glu Gln Leu Ala
         80                  85                  90 cag gag gct gtc cgt cgc ttg gac atc ggg cac ctg aag ttg aca ttt      519
Gln Glu Ala Val Arg Arg Leu Asp Ile Gly His Leu Lys Leu Thr Phe
     95                 100                 105 tgc aga gtg ggc cct gca gag tgt gct gca ctg gcc ttt gta ctg caa      567
Cys Arg Val Gly Pro Ala Glu Cys Ala Ala Leu Ala Phe Val Leu Gln
110                 115                 120                 125 cat ctc cag cgg cct gtg gcc cta cag ctg gat tac aac tct gtg          612
His Leu Gln Arg Pro Val Ala Leu Gln Leu Asp Tyr Asn Ser Val
                130                 135                 140
```

```
ggagatgttg ggagtggaac agctgcgacc gtgcctttgg ggtctgcaca gctctgtagt      672
gagtgtgaca aggtcttgcc gattgggcct gtggcaaatg ctactgtca                 721

<210> SEQ ID NO 191
<211> LENGTH: 140
<212> TYPE: PRT
<213> ORGANISM: Mus musculus

<400> SEQUENCE: 191

Leu Gln Lys Ala Glu Pro His Asn Leu Gln Ile Thr Ala Ala Phe Leu
 1               5                  10                  15

Ala Gly Leu Leu Ser Gln Gln His Arg Asp Leu Leu Ala Ala Cys Gln
             20                  25                  30

Val Ser Glu Arg Val Leu Leu Gln Arg Gln Ala Arg Ala Arg Ser Cys
         35                  40                  45

Leu Ala His Ser Leu Arg Glu His Phe His Ser Ile Pro Pro Ala Val
     50                  55                  60

Pro Gly Glu Thr Lys Ser Met His Ala Met Pro Gly Phe Ile Trp Leu
 65                  70                  75                  80

Ile Arg Ser Leu Tyr Glu Met Gln Glu Glu Gln Leu Ala Gln Glu Ala
                 85                  90                  95

Val Arg Arg Leu Asp Ile Gly His Leu Lys Leu Thr Phe Cys Arg Val
            100                 105                 110

Gly Pro Ala Glu Cys Ala Ala Leu Ala Phe Val Leu Gln His Leu Gln
        115                 120                 125

Arg Pro Val Ala Leu Gln Leu Asp Tyr Asn Ser Val
    130                 135                 140

<210> SEQ ID NO 192
<211> LENGTH: 419
<212> TYPE: DNA
<213> ORGANISM: Mus musculus
<220> FEATURE:
<221> NAME/KEY: CDS
<222> LOCATION: (1)...(417)

<400> SEQUENCE: 192 ctg cag aag gct gag cca cac aac ctg cag atc aca gca gcc ttc cta       48
Leu Gln Lys Ala Glu Pro His Asn Leu Gln Ile Thr Ala Ala Phe Leu
 1               5                  10                  15 gca ggt ctg ttg tcc cag cag cat cgg gac ctg ttg gct gca tgc cag       96
Ala Gly Leu Leu Ser Gln Gln His Arg Asp Leu Leu Ala Ala Cys Gln
             20                  25                  30 atc tcc gag agg gtg ctc ctc cag cgt cag gca cgt gcc cgc tcg tgt      144
Ile Ser Glu Arg Val Leu Leu Gln Arg Gln Ala Arg Ala Arg Ser Cys
         35                  40                  45 ctg gcc cac agc ctc cgc gag cac ttc cat tcc atc ccg cct gcc gtg      192
Leu Ala His Ser Leu Arg Glu His Phe His Ser Ile Pro Pro Ala Val
     50                  55                  60 ccc ggt gag acc aag agc atg cat gct atg ccg ggc ttt att tgg ctc      240
Pro Gly Glu Thr Lys Ser Met His Ala Met Pro Gly Phe Ile Trp Leu
 65                  70                  75                  80 atc cgg agc ctg tac gag atg cag gag gag cag ttg gcc cag gag gct      288
Ile Arg Ser Leu Tyr Glu Met Gln Glu Glu Gln Leu Ala Gln Glu Ala
                 85                  90                  95 gtc cgt cgc ttg gac atc ggg cac ctg aag ttg aca ttt tgc aga gtg      336
Val Arg Arg Leu Asp Ile Gly His Leu Lys Leu Thr Phe Cys Arg Val
            100                 105                 110
```

```
ggc cct gca gag tgt gct gcg ctg gcc ttt gta ctg caa cat ctc cag    384
Gly Pro Ala Glu Cys Ala Ala Leu Ala Phe Val Leu Gln His Leu Gln
        115                 120                 125 cgg cct gtg gcc cta cag ctg gat tac aac tct gt                      419
Arg Pro Val Ala Leu Gln Leu Asp Tyr Asn Ser
        130                 135

<210> SEQ ID NO 193
<211> LENGTH: 139
<212> TYPE: PRT
<213> ORGANISM: Mus musculus

<400> SEQUENCE: 193

Leu Gln Lys Ala Glu Pro His Asn Leu Gln Ile Thr Ala Ala Phe Leu
 1               5                  10                  15

Ala Gly Leu Leu Ser Gln Gln His Arg Asp Leu Leu Ala Ala Cys Gln
            20                  25                  30

Ile Ser Glu Arg Val Leu Leu Gln Arg Gln Ala Arg Ala Arg Ser Cys
        35                  40                  45

Leu Ala His Ser Leu Arg Glu His Phe His Ser Ile Pro Pro Ala Val
    50                  55                  60

Pro Gly Glu Thr Lys Ser Met His Ala Met Pro Gly Phe Ile Trp Leu
65                  70                  75                  80

Ile Arg Ser Leu Tyr Glu Met Gln Glu Glu Gln Leu Ala Gln Glu Ala
                85                  90                  95

Val Arg Arg Leu Asp Ile Gly His Leu Lys Leu Thr Phe Cys Arg Val
            100                 105                 110

Gly Pro Ala Glu Cys Ala Ala Leu Ala Phe Val Leu Gln His Leu Gln
        115                 120                 125

Arg Pro Val Ala Leu Gln Leu Asp Tyr Asn Ser
        130                 135

<210> SEQ ID NO 194
<211> LENGTH: 26
<212> TYPE: DNA
<213> ORGANISM: Artificial Sequence
<220> FEATURE:
<223> OTHER INFORMATION: primer

<400> SEQUENCE: 194
ctgcagaagg ctgagccaca caacct                                        26

<210> SEQ ID NO 195
<211> LENGTH: 30
<212> TYPE: DNA
<213> ORGANISM: Artificial Sequence
<220> FEATURE:
<223> OTHER INFORMATION: primer

<400> SEQUENCE: 195
acagagttgt aatccagctg tagggccaca                                    30
```

CARD DOMAIN CONTAINING POLYPEPTIDES, ENCODING NUCLEIC ACIDS, AND METHODS OF USE

This application is a continuation of application Ser. No. 09/864,921, filed May 23, 2001, now U.S. Pat. No. 7,196,182, which claims the benefit of three U.S. Provisional Applications: Application Ser. No. 60/325,756 filed May 24, 2000, which was converted from U.S. Ser. No. 09/579,240; and Application No. 60/367,337, filed Oct. 10, 2000, which was converted from U.S. Ser. No. 09/686,347; and Application No. 60/275,980, filed Mar. 14, 2001, each of which is incorporated herein by reference in its entirety.

This invention was made in part with U.S. Government support under NIH Grant No. GM61694 awarded by the National Institutes of Health. The U.S. Government has certain rights in this invention.

BACKGROUND OF THE INVENTION

1. Field of the Invention

This invention relates generally to the fields of molecular biology and molecular medicine and more specifically to the identification of proteins involved in programmed cell death, cytokine processing and receptor signal transduction, and associations of these proteins.

2. Background Information

Programmed cell death is a physiologic process that ensures homeostasis is maintained between cell production and cell turnover in essentially all self-renewing tissues. In many cases, characteristic morphological changes, termed "apoptosis," occur in a dying cell. Since similar changes occur in different types of dying cells, cell death appears to proceed through a common pathway in different cell types.

In addition to maintaining tissue homeostasis, apoptosis also occurs in response to a variety of external stimuli, including growth factor deprivation, alterations in calcium levels, free-radicals, cytotoxic lymphokines, infection by some viruses, radiation and most chemotherapeutic agents. Thus, apoptosis is an inducible event that likely is subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely. In viral infections, induction of apoptosis can figure prominently in the pathophysiology of the disease process, because immune-based for eradication of viral infections depend on elimination of virus-producing host cells by immune cell attack resulting in apoptosis.

Some of the proteins involved in programmed cell death have been identified and associations among some of these proteins have been described. However, additional apoptosis regulating proteins remain to be found and the mechanisms by which these proteins mediate their activity remains to be elucidated. The identification of the proteins involved in cell death and an understanding of the associations between these proteins can provide a means for manipulating the process of apoptosis in a cell and, therefore, selectively regulating the relative lifespan of a cell or its relative resistance to cell death stimuli.

The principal effectors of apoptosis are a family of intracellular proteases known as Caspases, representing an abbreviation for Cysteine Aspartyl Proteases. Caspases are found as inactive zymogens in essentially all animal cells. During apoptosis, the caspases are activated by proteolytic processing at specific aspartic acid residues, resulting in the production of subunits that assemble into an active protease typically consisting of a heterotetramer containing two large and two small subunits. The phenomenon of apoptosis is produced directly or indirectly by the activation of caspases in cells, resulting in the proteolytic cleavage of specific substrate proteins. Moreover, in many cases, caspases can cleave and activate themselves and each other, creating cascades of protease activation and mechanisms for "auto"-activation. Thus, knowledge about the proteins that interact with and regulate caspases is important for devising strategies for manipulating cell life and death in therapeutically useful ways. In addition, because caspases can also participate in cytokine activation and other processes, knowledge about the proteins that interact with caspases can be important for manipulating immune responses and other biochemical processes in useful ways.

One of the mechanisms for regulating caspase activation involves protein-protein interactions mediated by a family of protein domains known as caspase recruitment domains (CARDs). The identification of proteins that contain CARD domains and the elucidation of the proteins with which they interact, therefore, can form the basis for strategies designed to alter apoptosis, cytokine production, cytokine receptor signaling, and other cellular processes. Thus, a need exists to identify proteins that contain CARD domains. The present invention satisfies this need and provides additional advantages as well.

SUMMARY OF THE INVENTION

The invention provides caspase recruitment domain (CARD)-containing polypeptides, and CARD, NB-ARC, ANGIO-R, LRR and SAM domains therefrom. Also provided are chimeric polypeptides containing a CARD, NB-ARC, ANGIO-R, LRR or SAM domain of a CARD-containing polypeptide. Methods of producing CARD-containing polypeptides, and compositions containing CARD-containing polypeptides and a pharmaceutically acceptable carrier, are also provided.

The invention further provides nucleic acid molecules encoding CARD-containing polypeptides and CARD, NB-ARC, ANGIO-R, LRR and SAM domains therefrom. Also provided are antibodies directed against such polypeptides.

The invention also provides methods for identifying a nucleic acid molecule encoding a CARD-containing polypeptide, and methods for detecting the presence of a CARD-containing polypeptide in a sample.

Further provided are methods of identifying a CARD-associated polypeptide (CAP), and methods of identifying an effective agent that alters the association of a CARD-containing polypeptide with a CAP. The invention also provides methods of identifying an effective agent that modulates an activity of a NB-ARC domain of a CARD-containing polypeptide.

The invention also provides methods of altering the level of a biochemical process modulated by a CARD-containing polypeptide.

The invention further provides methods of treating a pathology characterized by abnormal cell proliferation, abnormal cell death, or inflammation.

Also provided are methods of diagnosing or predicting clinical prognosis of a pathology characterized by an increased or decreased level of a CARD-containing polypeptide in a subject.

BRIEF DESCRIPTION OF THE FIGURES

FIG. 2 shows an alignment of the protein sequence of the isoforms of CLAN (designated CLAN A, B, C and D; SEQ ID NOS: 97, 99, 103 and 101, respectively). Dark boxes indicate identical amino acids, and white boxes indicate conserved amino acids.

FIG. 3 shows the amino acid sequences of the CARD-A, CARD-B and NB-ARC domains of CARD3X (SEQ ID NOS: 170, 172 and 174, respectively).

FIG. 4 shows an alignment of COP-1 (SEQ ID NO:86) and caspase-1 (SEQ ID NO:87). The amino acids shaded in black are identical.

FIG. 5 shows an alignment of COP-2 (SEQ ID NO:90) and caspase-1 (SEQ ID NO:87), with the consensus sequence (SEQ ID NO:91) shown above the aligned sequences. The amino acids shaded in black are identical.

DETAILED DESCRIPTION OF THE INVENTION

Figure 1A:
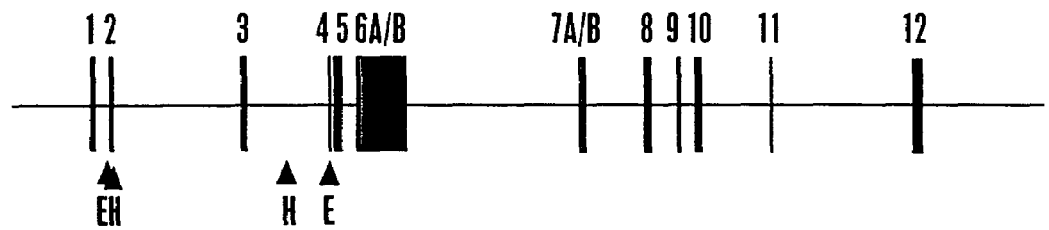
FIG. 1A shows the genomic organization of the CLAN (CARD 4/5X) gene on chromosome 2 deduced from the BAC 164M19 sequence from the SPG4 candidate region at 2p21-2p22 (Accession No. AL121653) and *Homo sapiens* chromosome 2 working draft sequence (Accession No. NT_005194.1).

The present invention provides novel polypeptides involved in programmed cell death, or apoptosis. The principal effectors of apoptosis are a family of intracellular cysteine aspartyl proteases, known as caspases. Caspase activity in the cell is regulated by protein-protein interactions. Similarly, protein-protein interactions influence the activity of other proteins involved in apoptosis. Several protein interaction domains have been implicated in interactions among some apoptosis-regulating proteins. Among these is the caspase recruitment domain, or CARD-containing polypeptide which are so named for the ability of the CARD-containing polypeptides to bind caspases. In addition to their ability to bind caspases, numerous CARD-containing polypeptides bind other proteins, particularly, other CARD-containing polypeptides. Further, CARD-containing polypeptides influence a variety of cellular and biochemical processes beyond apoptosis, including cell adhesion, inflammation and cytokine receptor signaling.

In accordance with the present invention, there are provided isolated CARD-containing polypeptides or functional fragments thereof, comprising substantially the same amino acid sequence as set forth in any of SEQ ID NOS: 12, 168, 188, 170, 172, 174, 176, 97, 99, 101, 103, 178, 180, 182, 184, 86 and 90.

The sequence identifiers set forth above correspond to the molecules described herein as set forth in Table 1.

TABLE 1

| Designation | Nucleotide SEQ ID NO: | Polypeptide SEQ ID NO: |
|---|---|---|
| CARD2X | 11 | 12 |
| CARD2X CARD Domain | 167 | 168 |
| CARD3X | 187 | 188 and 189 |
| CARD3X CARDA Domain | 169 | 170 |
| CARD3X CARDB Domain | 171 | 172 |
| CARD3X NB-ARC Domain | 173 | 174 |
| CARD3X ANGIO-R Domain | 175 | 176 |
| CLAN A | 96 | 97 |

TABLE 1-continued

| Designation | Nucleotide SEQ ID NO: | Polypeptide SEQ ID NO: |
|---|---|---|
| CLAN B | 98 | 99 |
| CLAN C | 100 | 101 |
| CLAN D | 102 | 103 |
| CLAN CARD | 177 | 178 |
| CLAN NACHT | 179 | 180 |
| CLAN LRR | 181 | 182 |
| CLAN SAM | 183 | 184 |
| COP1 | 85 | 86 |
| COP2 | 89 | 90 |

The terms "CARD-containing protein" or "CARD-containing polypeptide" as used herein refer to a protein or polypeptide containing a CARD domain. As used herein, the term "CARD domain" refers to a Caspase Recruitment Domain. A CARD domain is a well known protein domain of approximately 80 amino acids with characteristic sequence conservation as described, for example, in Hofmann et al., *Trends Biochem. Sci.* 22:155-156 (1997). CARD domains have been found in some members of the Caspase family of cell death proteases. Caspases-1, 2, 4, 5, 9, and 11 contain CARD domains near their NH2-termini. These CARD domains-mediate interactions of the zymogen inactive forms of caspases with other proteins which can either activate or inhibit the activation of these enzymes.

For example, the CARD domain of pro-caspase-9 binds to the CARD domain of a caspase-activating protein called Apaf-1 (Apoptosis Protease Activating Factor-1). Similarly, the CARD domain of pro-caspase-1 permits interactions with another CARD protein known as Cardiac (also referred to as RIP2 and RICK), which results in activation of the caspase-1 protease (Thome et al., *Curr. Biol.* 16:885-888 (1998)). Additionally, pro-caspase-2 binds to the CARD protein Raidd (also know as Cradd), which permits recruitment of pro-caspase-2 to Tumor Necrosis Factor (TNF) Receptor complexes and which results in activation of the caspase-2 protease (Ahmad et al., *Cancer Res.* 57:615-619 (1997)). CARD domains can also participate in homotypic interactions with themselves, resulting in self-association of polypeptides that contain these protein-interaction domains and producing dimeric or possibly even oligomeric complexes.

CARD domains can be found in association with other types of functional domains within a single polypeptide, thus providing a mechanism for bringing a functional domain into close proximity or contact with a target protein via CARD:CARD associations involving two CARD-containing polypeptides. For example, the *Caenorhabiditis elegans* cell death gene ced-4 encodes a protein that contains a CARD domain and a ATP-binding oligomerization domain called an NB-ARC domain (van der Biezen and Jones, *Curr. Biol.* 8:R226-R227). The CARD domain of the CED-4 protein interacts with the CARD domain of a pro-caspase called CED-3. The NB-ARC domain allows CED-4 to self associate, thereby forming an oligomeric complex which brings associated pro-CED-3 molecules into close proximity to each other. Because most pro-caspases possess at least a small amount of protease activity even in their unprocessed form, the assembly of a complex that brings the proforms of caspase into juxtaposition can result in trans-processing of zymogens, producing the proteolytically processed and active caspase. Thus, CED-4 employs a CARD domain for binding a pro-caspase and an NB-ARC domain for self-oligomerization, resulting in caspase clustering, proteolytic processing and activation.

In addition to their role in caspase activation, CARD domains have been implicated in other cellular processes. Some CARD-containing polypeptides, for example, induce activation of the transcription factor NF-kB. NF-kB activation is induced by many cytokines and plays an important role in cytokine receptor signal transduction mechanisms (DiDonato et al., *Nature* 388:548-554 (1997)). Moreover, CARD domains are found in some proteins that inhibit rather than activate caspases, such as the IAP (Inhibitor of Apoptosis Protein) family members, cIAP1 and cIAP2 (Rothe et al., *Cell* 83:1243-1252 (1995)) and oncogenic mutants of the Bcl-10 protein (Willis et al., *Cell* 96:35-45 (1999)). Also, though caspase activation resulting from CARD domain interactions is often involved in inducing apoptosis, other caspases are primarily involved in proteolytic processing and activation of inflammatory cytokines (such as pro-IL-1b and pro-IL-18). Thus, CARD-containing polypeptides can also be involved in cytokine receptor signaling and cytokine production, and, therefore, can be involved in regulation of immune and inflammatory responses.

In view of the function of the CARD domain within the invention CARD-containing polypeptides or functional fragments thereof, polypeptides of the invention are contemplated herein for use in methods to alter biochemical processes such as apoptosis, NF-kB induction, cytokine processing, cytokine receptor signaling, caspase-mediated proteolysis, thus having modulating effects on cell life and death (i.e., apoptosis), inflammation, cell adhesion, and other cellular and biochemical processes.

Invention CARD-containing polypeptides or functional fragments thereof (including CARD domains) are also contemplated in methods to identify CARD-binding agents and CARD-associated polypeptides (CAPs) that alter apoptosis, NF-kB induction, cytokine processing, cytokine receptor signaling, caspase-mediated proteolysis, thus having modulating effects on cell life and death (i.e., apoptosis), inflammation, cell adhesion, and other cellular and biochemical processes.

It is also contemplated herein that invention CARD-containing polypeptides can associate with other CARD-containing polypeptides to form invention hetero-oligomers or homo-oligomers, such as heterodimers or homodimers. In particular, the association of the CARD domain of invention polypeptides with other CARD-containing polypeptides, such as Apaf-1, CED-4, caspases-1, 2, 9, 11, cIAPs-1 and 2, CARDIAK, Raidd, Dark, CLAN, other invention CARD-containing polypeptides, and the like, including homo-oligomerization, is sufficiently specific such that the bound complex can form in vivo in a cell or in vitro under suitable conditions. Similarly therefore, an invention CARD-containing polypeptide can associate with another CARD-containing polypeptide by CARD:CARD form invention hetero-oligomers or homo-oligomers, such as heterodimers or homodimers.

In accordance with the present invention, sequences for novel CARD-containing polypeptides have been determined. Thus, the present invention provides novel CARD-containing polypeptides, including the newly identified CARD-containing polypeptides designated CARD2X, CARD3X, CLAN A, CLAN B, CLAN C, CLAN D, COP-1 and COP-2 (set forth in SEQ ID NOS: 12, 188, 97, 99, 101, 103, 86 and 90).

In addition to CARD domains, invention polypeptides can contain one or more additional domains. The locations within the reference sequence of the domains described herein are set forth in Table 2.

TABLE 2

| Domain | Corresponding amino acids | SEQ ID NO: |
|---|---|---|
| CARD2X | 4-78 of SEQ ID NO: 12 | 167 (nt) |
| CARD Domain | | 168 (aa) |
| CARD3X | 2-78 of SEQ ID NO: 107 | 169 (nt) |
| CARDA Domain | | 170 (aa) |
| CARD3X | 105-185 of SEQ ID NO: 107 | 171 (nt) |
| CARDB Domain | | 172 (aa) |
| CARD3X | 265-560 of SEQ ID NO: 107 | 173 (nt) |
| NB-ARC Domain | | 174 (aa) |
| CARD3X | 437-839 of SEQ ID NO: 107 | 175 (nt) |
| ANGIO-R Domain | | 176 (aa) |
| CLAN | 1-87 of SEQ ID NO: 97 | 177 (nt) |
| CARD Domain | | 178 (aa) |
| CLAN | 161-457 of SEQ ID NO: 97 | 179 (nt) |
| NACHT Domain | | 180 (aa) |
| CLAN | 760-965 of SEQ ID NO: 97 | 181 (nt) |
| LRR Domain | | 182 (aa) |
| CLAN | 642-696 of SEQ ID NO: 97 | 183 (nt) |
| SAM Domain | | 184 (aa) |

CARD3X (SEQ ID NO:88) contains at least four distinct domains: two CARD domains, designated CARD-A and CARD-B, an NB-ARC domain and an angio-R domain. A second in-frame, open reading frame that begins after a stop codon encodes a domain with several leucine rich repeats (LRR) (SEQ ID NO:189) (see Example). An invention CARD3X polypeptide can thus contain the amino acid sequence designated SEQ ID NO:188 and the amino acid sequence designated SEQ ID NO:189; contain SEQ ID NO:188 but not SEQ ID NO:189; or contain SEQ ID NO:189 but not SEQ ID NO:188. A murine CARD3X polypeptide can contain the amino acid sequence designated SEQ ID NO:193, which is homologous to a portion of the human CARD3X ANGIO-R domain, with or without one or more additional CARD3X domains.

CLAN exists in four isoforms (see Example), each of which contains a CARD domain. The longest isoform, CLAN-A, also contains an NB-ARC (NACHT) domain, a LRR domain and a SAM domain. CLAN represents a new member of the CED-4 related protein family. Numerous CED-4-related proteins have recently been identified. These proteins belong to the CED-4 family of proteins, and include CED-4 (Yuan and Horvitz, *Development* 116:309-320 (1992)), Apaf-1, (Zou et al., *Cell* 90:405-413 (1997)), Dark (Rodriguez et al., *Nature Cell Biol.* 1:272-279 (1999)), and CARD4/Nod1 (Bertin et al., *J. Biol. Chem.* 274:12955-12958 (1999) and Inohara et al., *J. Biol. Chem.* 274:14560-14567 (1999)). As used herein, a "CED-4 family" member or "CED-4 protein family" member, also referred to herein as a "NAC" polypeptide, is a polypeptide that comprises a NB-ARC domain and a CARD domain.

The CED-4 homolog in humans and rodents, referred to as Apaf-1, contains a (i) CARD domain, (ii) NB-ARC domain, and (iii) multiple copies of a WD-repeat domain. In contrast to CED-4 which can spontaneously oligomerize, the mammalian Apaf-1 protein is an inactive monomer until induced to oligomerize by binding of a co-factor protein, cytochrome c (Li et al., *Cell* 91:479-489 (1997)). In Apaf-1, the WD repeat domains prevent oligomerization of the Apaf-1 protein, until coming into contact with cytochrome c. Thus, the WD-repeats function as a negative-regulatory domain that maintains Apaf-1 in a latent state until cytochrome c release from damaged mitochondria triggers the assembly of an oligomeric Apaf-1 complex (Saleh, *J. Biol. Chem.* 274:17941-17945 (1999)). By binding pro-caspase-9 through its CARD domain, Apaf-1 oligomeric complexes are thought to bring the zymogen forms of caspase-9 into close proximity, permitting them to cleave each other and produce the proteolytic processed and active caspase-9 protease (Zou et al., *J. Biol. Chem.* 274:11549-11556 (1999)).

Another characteristic of the invention CARD-containing polypeptides is that they can associate with pro-caspases, caspases or with caspase-associated proteins, thereby altering caspase proteolytic activity. Caspase proteolytic activity is associated with apoptosis of cells, and additionally with cytokine production. Therefore, an invention CARD-containing polypeptide can alter apoptosis or cytokine production by altering caspase proteolytic activity. As used herein a "caspase" is any member of the cysteine aspartyl proteases. Typically, as caspase can associate with a CARD-containing polypeptide of the invention such as a NAC polypeptide. Similarly, a "pro-caspase" is an inactive or less-active precursor form of a caspase, which is typically converted to the more active caspase form by a proteolytic event, and often a proteolytic event preceded by a protein:protein interaction such as a CARD:CARD interaction, and the like.

As described in the Example, COP-1 interacts with the prodomain of pro-caspase-1 and also with RIP2, a protein previously demonstrated to bind the prodomain of pro-caspase-1. COP-1 competes with RIP2 for binding to pro-caspase-1, thereby inhibiting RIP2-mediated caspase-1 oligomerization. Consequently, COP-1 interferes with the ability of RIP2 to enhance caspase-1-induced secretion of mature IL-1β. Therefore, COP-1 is likely to play a role in controlling IL-1β generation and thereby opposing IL-1β-induced inflammation. IL-1β plays a critical role in septic shock, which currently represents the most common cause of lethality in patients treated in the intensive care setting. Accordingly, COP-1 likely plays a role in IL-1β homeostasis to prevent systemic inflammatory reactions when challenged with gram-negative bacteria or other inflammatory insults.

As also described in the Example, because of their interactions with diverse other CARD proteins, the isoforms of CLAN (A, B, C and D) likely influence apoptosis, cytokine processing, or NF-kB activity. Interactions of CLAN with pro-caspase-1 likely indicates a role for CLAN as a IL-1β regulator. In this regard, different isoforms of CLAN likely have opposing effects on pro-caspase-1 activation. The longest isoform, CLAN-A, for example, can trigger pro-caspase-1 activation by the "induced proximity" mechanism as a result of oligomerization mediated by its NB-ARC (NACHT) domain. In contrast, the shorter isoforms of CLAN lacking this self-oligomerization can operate as competitive antagonists of pro-caspase-1 activation, analogous to ICEBERG, a CARD-containing protein that competes with CARDIAK (RIP2/RICK) for binding to pro-caspase-1. Interactions of CLAN with NAC also suggest this protein can have an influence on apoptosis mediated by Apaf-1, in as much as NAC binds Apaf-1 and enhances its ability to activate caspase-9 in response to cytochrome c. Finally, CLAN associations with NF-kB regulators such as Bcl-10 and Nod2 strongly suggest that at least some of the CLAN isoforms can influence the activity of this transcription factor.

In addition to the ability to bind caspases, invention CARD-containing polypeptides can contain a protease domain, such as a protease domain found in caspase, and the like. A caspase protease domain hydrolyzes amide bonds, particularly the amide bond of a peptide or polypeptide backbone. Typically, a caspase protease domain contains a P20/P10 domain in the active site region of the caspase protease domain. Thus, a caspase protease domain has proteolytic activity.

CARD-containing polypeptides are also known to induce activation of the transcription factor NF-kB. Thus, an invention CARD-containing polypeptide can also alter transcription by, for example, modulation of NF-kB activity, and the like.

The NB-ARC (NACHT) domain of invention NAC polypeptides such as CLAN and CARD3X (see Example) associates with other polypeptides, particularly with polypeptides comprising NB-ARC domains. Thus, a functional NB-ARC domain associates with NB-ARC domain-containing polypeptides by way of NB-ARC:NB-ARC association. As used herein, the term "associate" or "association" means that CARD-containing polypeptide such as a NAC polypeptide can bind to a polypeptide relatively specifically and, therefore, can form a bound complex. For example, the association of a CARD domain of an invention CARD-containing polypeptide with another CARD-containing polypeptide or the association of a NB-ARC domain of NAC with another NB-ARC domain-containing polypeptides is sufficiently specific such that the bound complex can form in vivo in a cell or in vitro under suitable conditions.

Further, a NB-ARC domain demonstrates both nucleotide-binding (e.g., ATP-binding) and hydrolysis activities, which is typically required for its ability to associate with NB-ARC domain-containing polypeptides. Thus, an NB-ARC domain of the invention NAC comprises one or more nucleotide binding sites. As used herein, a nucleotide binding site is a portion of a polypeptide that specifically binds a nucleotide such as, e.g., ADP, ATP, and the like. Typically, the nucleotide binding site of NB-ARC will comprise a P-loop, a kinase 2 motif, or a kinase 3a motif of the invention NAC (these motifs are defined, for example, in van der Biezen and Jones, supra). Preferably, the nucleotide binding site of NB-ARC comprises a P-loop of the invention NAC. The NB-ARC domain of the an invention CARD-containing polypeptide, therefore, is capable of associating with other NB-ARC domains in homo- or hetero-oligomerization. Additionally, the NB-ARC domain is characterized by nucleotide hydrolysis activity, which can influence the ability of an NB-ARC domain to associate with another NB-ARC domain.

An invention NAC, therefore, is capable of CARD:CARD association and/or NB-ARC:NB-ARC association, resulting in a multifunctional polypeptide capable of one or more specific associations with other polypeptides. An invention NAC can alter cell processes such as apoptosis, cytokine production, and the like. For example, it is contemplated herein that an invention NAC polypeptide can increase the level of apoptosis in a cell. It is also contemplated herein that an invention NAC can decrease the level of apoptosis in a cell. For example, a NAC which does not induce apoptosis may form hetero-oligomers with a NAC which is apoptotic, thus interfering with the apoptosis-inducing activity of NAC.

In another embodiment of the invention, a CARD-containing polypeptide of the invention, such as CLAN (SEQ ID NOS:96, 98, 100 and 102) and an isoform of CARD3X (containing SEQ ID NO:189) also contains Leucine-Rich Repeats (LRR) domain. LRR domains are well known in the art and, in one embodiment, the LRR domain of an invention CARD-containing polypeptide has substantially the same sequence as a LRR described in another CARD-containing polypeptide known as Nod1 (Inohara et al., *J. Biol. Chem.* 274:14560-14567 (1999)). The function of the LRR domain is to mediate specific interactions with other polypeptides.

In another embodiment of the invention, there are provided CARD-containing polypeptides that contain an NB-ARC domain and a CARD domain. NAC polypeptide sequences disclosed herein, for example, CARD4/5X (CLAN), modulate a variety of biochemical processes such as apoptosis. NAC polypeptides can also have other domains that modulate biochemical processes such as an LRR domain or a WD domain.

Those of skill in the art will recognize that numerous residues of the above-described sequences can be substituted with other, chemically, sterically and/or electronically similar residues without substantially altering the biological activity of the resulting CARD-containing polypeptide species. In addition, larger polypeptide sequences comprising substantially the same sequence as amino acids set forth in SEQ ID NOS:12, 168, 188, 170, 172, 174, 176, 97, 99, 101, 103, 178, 180, 182, 184, 8.6 and 90, therein are contemplated within the scope of the invention.

As employed herein, the term "substantially the same amino acid sequence" refers to amino acid sequences having at least about 70% or 75% identity with respect to the reference amino acid sequence, and retaining comparable functional and biological activity characteristic of the polypeptide defined by the reference amino acid sequence. Preferably, polypeptides having "substantially the same amino acid sequence" will have at least about 80%, 82%, 84%, 86% or 88%, more preferably 90%, 91%, 92%, 93% or 94% amino acid identity with respect to the reference amino acid sequence; with greater than about 95%, 96%, 97%, 98% or 99% amino acid sequence identity being especially preferred. It is recognized, however, that polypeptides or nucleic acids containing less than the described levels of sequence identity arising as splice variants or that are modified by conservative amino acid substitutions, or by substitution of degenerate codons are also encompassed within the scope of the present invention.

In accordance with the invention, specifically included within the definition of substantially the same amino acid sequence is the predominant amino acid sequence of a particular invention CARD-containing polypeptide or domain disclosed herein. The predominant amino acid sequence refers to the most commonly expressed naturally occurring amino acid sequence in a species population. A predominant polypeptide with multiple isoforms will have the most commonly expressed amino acid sequence for each isoform. A predominant CARD-containing polypeptide of the invention refers to an amino acid sequence having sequence identity to an amino acid sequence disclosed herein that is greater than that of any other naturally occurring protein of a particular species (e.g., human).

Given the teachings herein of the location and nucleic acid or amino acid sequences corresponding to the invention CARD-containing polypeptides, one of skill in the art can readily confirm and, if necessary, revise the nucleic acid or amino acid sequences associated with the CARD-containing polypeptides of the invention. For example, the sequences can be confirmed by probing a cDNA library with a nucleic acid probe corresponding to a nucleic acid of the invention using PCR or other known methods. Further, an appropriate bacterial artificial chromosome containing the region of the genome encoding an invention CARD-containing polypeptide can be commercially obtained and probed using PCR, restriction mapping, sequencing, and other known methods.

The term "biologically active" or "functional", when used herein as a modifier of invention CARD-containing polypeptides, or polypeptide fragments thereof, refers to a polypeptide that exhibits functional characteristics similar to a CARD-containing polypeptide of the invention. Biological activities of a CARD-containing polypeptide include, for example, the ability to bind, preferably in vivo, to a nucleotide, to a CARD-associated polypeptide, to a NB-ARC-containing polypeptide, or to homo-oligomerize, or to alter protease activation, particularly caspase activation, or to catalyze reactions such as proteolysis or nucleotide hydrolysis, or to alter NF-kB activity, or to alter apoptosis, cytokine processing, cytokine receptor signaling, inflammation, immune response, and other biological activities described herein.

The ability of a CARD-containing polypeptide to bind another polypeptide such as a CARD-associated polypeptide can be assayed, for example, using the methods well known in the art such as yeast two-hybrid assays, co-immunoprecipitation, GST fusion co-purification, and other methods provided in standard technique manuals such as Sambrook, supra, and Ausubel et al., supra. Another biological activity of a CARD-containing polypeptide is the ability to act as an immunogen for the production of polyclonal and monoclonal antibodies that bind specifically to an invention CARD-containing polypeptide. Thus, an invention nucleic acid encoding a CARD-containing polypeptide can encode a polypeptide specifically recognized by an antibody that also specifically recognizes a CARD-containing polypeptide (preferably human) including the amino acid set forth in SEQ ID NOS: 12, 168, 188, 170, 172, 174, 176, 97, 99, 101, 103, 178, 180, 182, 184, 86 and 90. Such immunologic activity may be assayed by any method known to those of skill in the art. For example, a test-polypeptide can be used to produce antibodies, which are then assayed for their ability to bind to an invention polypeptide. If the antibody binds to the test-polypeptide and to the reference polypeptide with substantially the same affinity, then the polypeptide possesses the requisite immunologic biological activity.

As used herein, the term "substantially purified" means a polypeptide that is in a form that is relatively free from contaminating lipids, polypeptides, nucleic acids or other cellular material normally associated with a polypeptide in a cell. A substantially purified CARD-containing polypeptide can be obtained by a variety of methods well-known in the art, e.g., recombinant expression systems described herein, chemical synthesis or purification from native sources. Purification methods can include, for: example, precipitation, gel filtration, ion-exchange, reverse-phase and affinity chromatography, and the like. Other well-known methods are described in Deutscher et al., "Guide to Protein Purification" *Methods in Enzymology* Vol. 182, (Academic Press, (1990)). Alternatively, the isolated polypeptides of the present invention can be obtained using well-known recombinant methods as described, for example, in Sambrook et al., supra, (1989) and Ausubel et al., supra (2000). The methods and conditions for biochemical purification of a polypeptide of the invention can be chosen by those skilled in the art, and purification monitored, for example, by an immunological assay, binding assay, or a functional assay.

In addition to the ability of invention CARD-containing polypeptides, or functional fragments thereof, to interact with other, heterologous proteins (e.g., CARD-containing polypeptides), invention CARD-containing polypeptides have the ability to self-associate to form invention homo-oligomers such as homodimers. This self-association is possible through interactions between CARD domains, and also through interactions between NB-ARC domains. Further, self-association can take place as a result of interactions between LRR domains.

In accordance with the invention, there are also provided mutations and fragments of CARD-containing polypeptides which have activity different than a predominant naturally occurring CARD-containing polypeptide activity. As used herein, a "mutation" can be any deletion, insertion, or change of one or more amino acids in the predominant naturally occurring protein sequence (e.g., wild-type), and a "fragment" is any truncated form, either carboxy-terminal, amino-terminal, or both, of the predominant naturally occurring protein. Preferably, the different activity of the mutation or fragment is a result of the mutant polypeptide or fragment maintaining some but not all of the activities of the respective predominant naturally occurring CARD-containing polypeptide.

For example, a functional fragment of an invention polypeptide can contain or consist of one or more of the following: a CARD domain, a NB-ARC domain, a LRR domain, a SAM domain, or an angio-R domain. In a specific example, a fragment of a CARD-containing polypeptide such as CLAN can contain a CARD domain and LRR domain, but lack a functional NB-ARC domain. Such a fragment will maintain a portion of the predominant naturally occurring CLAN activity (e.g., CARD domain functionality), but not all such activities (e.g., lacking an active NB-ARC domain). The resultant fragment will therefore have an activity different than the predominant naturally occurring CLAN activity. In another example, the CLAN polypeptide might have only the NB-ARC domain, allowing it to interact with other NB-ARC domain proteins in forming homo-oligomers or hetero-oligomers. In one embodiment, the activity of the fragment will be "dominant-negative." A dominant-negative activity will allow the fragment to reduce or inactivate the activity of one or more isoforms of a predominant naturally occurring CARD-containing polypeptide. Another functional fragment can include an angio-R domain (see Example), or any of the domains disclosed herein (see, for example, Table 2).

Isoforms of the CARD-containing polypeptides are also provided which arise from alternative mRNA splicing and may alter or modify the interactions of the CARD-containing polypeptide with other polypeptides. For example, four isoforms of CLAN and three isoforms of CARD3X are disclosed herein. Additional isoforms of the CARD-containing polypeptides designated SEQ ID NOS: 12, 188, 97, 99, 101, 103, 86 and 90, are contemplated herein and therefore, are encompassed within the scope of the invention CARD-containing polypeptides.

Methods to identify polypeptides containing a functional fragment of a CARD-containing polypeptide of the invention are well known in the art and are disclosed herein. For example, genomic or cDNA libraries, including universal cDNA libraries can be probed according to methods disclosed herein or other methods known in the art. Full-length polypeptide encoding nucleic acids such as full-length cDNAs can be obtained by a variety of methods well-known in the art. For example, 5' and 31 RACE, methodology is well known in the art and described in Ausubel et al., supra, and the like.

In another embodiment of the invention, chimeric polypeptides are provided comprising a CARD-containing polypeptide, or a functional fragment thereof, fused with another protein or functional fragment thereof. Functional fragments of a CARD-containing polypeptide include, for example, NB-ARC (NACHT), CARD, LRR, and ANGIO-R domains or other fragments that retain a biological activity of an invention CARD-containing polypeptide. Polypeptides with which the CARD-containing polypeptide or functional fragment thereof are fused will include, for example, glutathione-5-transferase, an antibody, or other proteins or functional fragments thereof which facilitate recovery of the chimera. Further, polypeptides with which a CARD-containing polypeptide or functional fragment thereof are fused will include, for example, luciferase, green fluorescent protein, an antibody, or other proteins or functional fragments thereof which facilitate identification of the chimera. Still further polypeptides with which a CARD-containing polypeptide or functional fragment thereof are fused will include, for example, the LexA DNA binding domain, ricin, a-sarcin, an antibody or fragment thereof, or other polypeptides which have therapeutic properties or other biological activity.

Further invention chimeric polypeptides contemplated herein are chimeric polypeptides wherein a functional fragment of a CARD-containing polypeptide is fused with a catalytic domain or a protein interaction domain from a heterologous polypeptide. For example, the NB-ARC domain of CLAN, as disclosed herein, can be replaced by the NB-ARC domain of other CARD polypeptides, such as CARD3X, and the like. Another example of such a chimera is a polypeptide wherein the CARD domain of CLAN is replaced by the CARD domain from CARD2X or CARD3X, and the like. In a further example, an NB-ARC domain can be fused with a caspase catalytic P20 domain to form a novel chimera with caspase activity. One of skill in the art will appreciate that a large number of chimeric polypeptides are readily available by combining domains of two or more CARD-containing polypeptides of the invention. Further, chimeric polypeptides can contain a functional fragment of a CARD-containing polypeptide of the invention fused with a domain of a protein known in the art, such as CED-4, Apaf-1, caspase-1, and the like.

In another embodiment of the invention, polypeptides are provided comprising 10 or more contiguous amino acids selected from the group consisting of SEQ ID NOS:12, 188, 97, 99, 101, 103, 86 and 90.

As used herein, the term "polypeptide" when used in reference to a CARD-containing polypeptide or fragment is intended to refer to a peptide or polypeptide of two or more amino acids. The term "polypeptide analog" includes any polypeptide having an amino acid residue sequence substantially the same as a sequence specifically described herein in which one or more residues have been conservatively substituted with a functionally similar residue and which displays the ability to functionally mimic a CARD-containing polypeptide as described herein. A "modification" of an invention polypeptide also encompasses conservative substitutions of an invention polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other groupings of amino acids can be found, for example in Taylor, *J. Theor. Biol.* 119:205-218 (1986), which is incorporated herein by reference. Other minor modifications are included within invention polypeptides so long as the polypeptide retains some or all of its function as described herein.

The amino acid length of functional fragments or polypeptide analogs of the present invention can range from about 5 amino acids up to the full-length protein sequence of an invention CARD-containing polypeptide. In certain embodiments, the amino acid lengths include, for example, at least about 10 amino acids, at least about 15, at least about 20, at least about 25, at least about 0, at least about 35, at least about 40, at least about 5, at least about 50, at least about 55, at least about 60, at least about 65, at least about 70, at least about 75, at least about 80, at least about 85, at least about 90, at least about 95, at least about 100, at least about 125, at least about 150, at least about 175, at least about 200, at least about 250 or more amino acids in length up to the full-length CARD-containing polypeptide sequence. The functional fragments can be contiguous amino acid sequences of an invention polypeptide, including contiguous amino acid sequences of SEQ ID NOS: 12, 188, 97, 99, 101, 103, 86 and 90. A peptide of at least about 10 amino acids can be used, for example, as an immunogen to raise antibodies specific for an invention CARD-containing polypeptide.

A modification of a polypeptide can also include derivatives, analogues and functional mimetics thereof, provided that such polypeptide displays a CARD-containing polypeptide biological activity. For example, derivatives can include chemical modifications of the polypeptide such as alkylation, acylation, carbamoylation, iodination, or any modification that derivatives the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptide having one or more additions and/or deletions of residues, relative to the sequence of a polypeptide whose sequence is shown herein, so long as CARD-containing polypeptide activity is maintained.

A modification of an invention polypeptide includes functional mimetics thereof. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide a function of a CARD-containing polypeptide, are included within the meaning of a CARD-containing polypeptide derivative. All of these modifications are included within the term "polypeptide" so long as the invention polypeptide or functional fragment retains its function. Exemplary mimetics are peptidomimetics, peptoids, or other peptide-like polymers such as poly(b-amino acids), and also non-polymeric compounds upon which functional groups that mimic a peptide are positioned.

Another embodiment of the invention provides a CARD-containing polypeptide, or a functional fragment thereof, fused with a moiety to form a conjugate. As used herein, a "moiety" can be a physical, chemical or biological entity which contributes functionality to a CARD-containing polypeptide or a functional fragment thereof. Functionalities contributed by a moiety include therapeutic or other biological activity, or the ability to facilitate identification or recovery of a CARD-containing polypeptide. Therefore, a moiety will include molecules known in the art to be useful for detection of the conjugate by, for example, by fluorescence, magnetic imaging, detection of radioactive emission. A moiety may also be useful for recovery of the conjugate, for example a His tag or other known tags used for protein isolation and/or purification, or a physical substance such as a bead. A moiety can be a therapeutic compound, for example, a cytotoxic drug which can be useful to effect a biological change in cells to which the conjugate localizes.

An example of the means for preparing the invention polypeptide(s) is to express nucleic acids encoding a CARD-containing polypeptide in a suitable host cell, such as a bacterial cell, a yeast cell, an amphibian cell such as an oocyte, or a mammalian cell, using methods well known in the art, and recovering the expressed polypeptide, again using well-known purification methods. Invention polypeptides can be isolated directly from cells that have been transformed with expression vectors as known in the art. Recombinantly expressed polypeptides of the invention can also be expressed as fusion proteins with appropriate affinity tags, such as glutathione S transferase (GST) or poly His, and affinity purified. The invention polypeptide, biologically functional fragments, and functional equivalents thereof can also be produced by in vitro transcription/translation methods known in the art, such as using reticulocyte lysates, as used for example, in the TNT system (Promega). The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

In accordance with another embodiment of the invention, there are provided isolated nucleic acids encoding a CARD-containing polypeptide or functional fragment thereof. The isolated nucleic acids can be selected from:

(a) DNA encoding a polypeptide containing the amino acid sequence set forth in SEQ ID NOs: 12, 168, 188, 170, 172, 174, 176, 97, 99, 101, 103, 178, 180, 182, 184, 86 and 90, or (b) DNA that hybridizes to the DNA of (a) under moderately stringent conditions, where the DNA encodes biologically active CARD-containing polypeptide, or (c) DNA degenerate with respect to (b), where the DNA encodes biologically active CARD-containing polypeptide.

The nucleic acid molecules described herein are useful for producing invention polypeptides, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention CARD-encoding gene or mRNA transcript in a given sample. The nucleic acid molecules described herein, and fragments thereof, are also useful as primers and/or templates in a PCR reaction for amplifying genes encoding invention polypeptides described herein.

The term "nucleic acid" (also referred to as polynucleotides) encompasses ribonucleic acid (RNA) or deoxyribonucleic acid (DNA), probes, oligonucleotides, and primers and can be single stranded or double stranded. DNA can be either complementary DNA (cDNA) or genomic DNA, e.g. a CARD-encoding gene, and can represent the sense strand, the anti-sense strand, or both. Examples of nucleic acids are RNA, cDNA, or isolated genomic DNA encoding a CARD-containing polypeptide. One means of isolating a CARD-encoding nucleic acid is to probe a mammalian genomic or cDNA library with a natural or artificially designed DNA probe using methods well known in the art. DNA probes derived from the CARD-encoding gene are particularly useful for this purpose. DNA and cDNA molecules that encode CARD-containing polypeptides can be used to obtain complementary genomic DNA, cDNA or RNA from mammalian (e.g., human, mouse, rat, rabbit, pig, and the like), or other animal sources, or to isolate related cDNA or genomic clones by screening cDNA or genomic libraries, using methods described in more detail below. Such nucleic acids include, but are not limited to, nucleic acids comprising substantially the same nucleotide sequence as set forth in SEQ ID NOS: 11, 167, 187, 169, 171, 173, 175, 96, 98, 100, 102, 177, 179, 181, 183, 85 and 89. In general, a genomic sequence of the invention includes regulatory regions such as promoters, enhancers, and introns that are outside of the exons encoding a CARD-containing polypeptide but does not include proximal genes that do not encode a CARD-containing polypeptide.

Thus a CARD-encoding nucleic acid as used herein refers to a nucleic acid encoding a CARD-containing polypeptide of the invention, or a functional fragment thereof.

Use of the terms "isolated" and/or "purified" and/or "substantially purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

Invention nucleic acids encoding CARD-containing polypeptides and invention CARD-containing polypeptides can be obtained from any species of organism, such as prokaryotes, eukaryotes, plants, fungi, vertebrates, invertebrates, and the like. A particular species can be mammalian, As used herein, "mammalian" refers to a subset of species from which an invention CARD-encoding nucleic acid is derived, e.g., human, rat, mouse, rabbit, monkey, baboon, bovine, porcine, ovine, canine, feline, and the like. A preferred CARD-encoding nucleic acid herein, is human CARD-encoding nucleic acid.

In one embodiment of the present invention, cDNAs encoding the invention CARD-containing polypeptides disclosed herein comprise substantially the same nucleotide sequence as the coding region set forth in any of SEQ ID NOS: 11, 167, 187, 169, 171, 173, 175, 96, 98, 100, 102, 177, 179, 181, 183, 85 and 89.

As employed herein, the term "substantially the same nucleotide sequence" refers to a nucleic acid molecule (DNA or RNA) having sufficient identity to the reference polynucleotide, such that it will hybridize to the reference nucleotide under moderately or highly stringent hybridization conditions. In one embodiment, a nucleic acid molecule having substantially the same nucleotide sequence as the reference nucleotide sequence encodes substantially the same amino acid sequence as that set forth in any of SEQ ID NOS: 12, 168, 188, 170, 172, 174, 176, 97, 99, 101, 103, 178, 180, 182, 184, 86 and 90. In another embodiment, a nucleic acid molecule having "substantially the same nucleotide sequence" as the reference nucleotide sequence has at least 60%, or at least 65% identity with respect to the reference nucleotide sequence, such as at least 70%, 72%, 74%, 76%, 78%, 80%, 82%, 84%, 86%, 88%, 90%, 91%, 92%, 93%, 94%, 95%, 96%, 97%, 98% or 99% identity to the reference nucleotide sequence.

In accordance with the invention, specifically included within the definition of substantially the same nucleotide sequence is the predominant nucleotide sequence of a particular invention CARD-containing polypeptide described herein. The predominant nucleotide sequence refers to the most commonly present naturally occurring nucleotide sequence in a species population. A predominant CARD-encoding nucleic acid of the invention refers to a nucleotide sequence having sequence identity to a nucleotide sequence disclosed herein that is greater than that of any other naturally occurring nucleotide sequence of a particular species (e.g., human).

In one embodiment, a nucleic acid molecule that has substantially the same nucleotide sequence as a reference sequence is a modification of the reference sequence. As used herein, a "modification" of a nucleic acid can include one or several nucleotide additions, deletions, or substitutions with respect to a reference sequence. A modification of a nucleic acid can include substitutions that do not change the encoded amino acid sequence due to the degeneracy of the genetic code. Such modifications can correspond to variations that are made deliberately, or which occur as mutations during nucleic acid replication.

Exemplary modifications of the recited nucleotide sequences include sequences that correspond to homologs of other species, including mammalian species such as mouse, primates, including monkey and baboon, rat, rabbit, bovine, porcine, ovine, canine, feline, or other animal species. The corresponding nucleotide sequences of non-human species can be determined by methods known in the art, such as by PCR or by screening genomic, cDNA or expression libraries.

Another exemplary modification of the invention CARD-encoding nucleic acid or CARD-containing polypeptide can correspond to splice variant forms of the CARD-encoding nucleotide sequence. Additionally, a modification of a nucleotide sequence can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a modification of a nucleotide sequence can include, for example, a detectable moiety, such as a radiolabel, a fluorochrome, a ferromagnetic substance, a luminescent tag or a detectable binding agent such as biotin. Such modifications can be advantageous in applications where detection of a CARD-encoding nucleic acid molecule is desired.

In another embodiment, a nucleic acid molecule that has substantially the same nucleotide sequence as a reference sequence is a functionally equivalent nucleic acid, which indicates that it is phenotypically similar to the reference nucleic acid. As used herein, the phrase "functionally equivalent nucleic acids" encompasses nucleic acids characterized by slight and non-consequential sequence variations that will function in substantially the same manner to produce the same polypeptide product(s) as the nucleic acids disclosed herein. In particular, functionally equivalent nucleic acids encode polypeptides that are the same as those encoded by the nucleic acids disclosed herein or that have conservative amino acid variations, as described above. These variations include those recognized by skilled artisans as those that do not substantially alter the tertiary structure of the protein.

Further provided are nucleic acids encoding CARD-containing polypeptides that, by virtue of the degeneracy of the genetic code, do not necessarily hybridize to the invention nucleic acids under specified hybridization conditions. Preferred nucleic acids encoding the invention CARD-containing polypeptides are comprised of nucleotides that encode substantially the same amino acid sequence as set forth in SEQ ID NOS:12, 168, 188, 170, 172, 174, 176, 97, 99, 101, 103, 178, 180, 182, 184, 86 and 90.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature (™) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-nucleic acid to bind a complementary nucleic acid. The hybridized nucleic acids will generally have at least about 60% identity, at least about 75% identity, such as at least about 85% identity; or at least about 90% identity. Moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C.

The phrase "high stringency hybridization" refers to conditions that permit hybridization of only those nucleic acid sequences that form stable hybrids in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., supra (1989); and Ausubel et al., supra, 2000). Nucleic acids encoding polypeptides hybridize under moderately stringent or high stringency conditions to substantially the entire sequence, or substantial portions, for example, typically at least 15-30 nucleotides of the nucleic acid sequence set forth in SEQ ID NOS:11, 167, 187, 169, 171, 173, 175, 96, 98, 100, 102, 177, 179, 181, 183, 85 and 89.

As used herein, the term "degenerate" refers to codons that differ in at least one nucleotide from a reference nucleic acid, e.g., SEQ ID NOS:11, 167, 187, 169, 171, 173, 175, 96, 98, 100, 102, 177, 179, 181, 183, 85 and 89, but encode the same amino acids as the reference nucleic acid. For example, codons specified by the triplets "UCU", "UCC", "UCA", and "UCG", are degenerate with respect to each other since all four of these codons encode the amino acid serine.

The invention also provides a modification of a nucleotide sequence that hybridizes to a CARD-encoding nucleic acid molecule, for example, a nucleic acid molecule referenced to any of SEQ ID NOS:11, 167, 187, 169, 171, 173, 175, 96, 98, 100, 102, 177, 179, 181, 183, 85 and 89 under moderately stringent conditions. Modifications of nucleotide sequences, where the modification has at least 60% identity to a CARD-encoding nucleotide-sequence, are also provided. The invention also provides modification of a CARD-encoding nucleotide sequence having at least 65% identity, at least 70% identity, at least 72% identity, at least 74% identity, at least 76% identity, at least 78% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity or at least 99% identity.

Identity of any two nucleic acid or amino acid sequences can be determined by those skilled in the art based, for example, on a BLAST 2.0 computer alignment, using default parameters. BLAST 2.0 searching is known in the art and is publicly available, for example, at http://www.ncbi.nlm.nih.gov/BLAST/, as described by Tatiana et al., *FEMS Microbiol Lett.* 174:247-250 (1999); Altschul et al., *Nucleic Acids Res.*, 25:3389-3402 (1997).

One means of isolating a nucleic acid encoding a CARD-containing polypeptide is to probe a cDNA library or genomic library with a natural or artificially designed nucleic acid probe using methods well known in the art. Nucleic acid probes derived from a CARD-encoding gene are particularly useful for this purpose. DNA and cDNA molecules that encode CARD-containing polypeptides can be used to obtain complementary genomic DNA, cDNA or RNA from mammals, for example, human, mouse, rat, rabbit, pig, and the like, or other animal sources, or to isolate related cDNA or genomic clones by the screening of cDNA or genomic libraries, by methods well known in the art (see, for example, the Examples set forth hereinafter; and Sambrook et al., supra, 1989; Ausubel et al., supra, 2000).

Another useful method for producing a CARD-encoding nucleic acid molecule of the invention involves amplification of the nucleic acid molecule using PCR and invention oligonucleotides and, optionally, purification of the resulting product by gel electrophoresis. Either PCR or RT-PCR can be used to produce a CARD-encoding nucleic acid molecule having any desired nucleotide boundaries as described in the Examples. Desired modifications to the nucleic acid sequence can also be introduced by choosing an appropriate oligonucleotide primer with one or more additions, deletions or substitutions. Such nucleic acid molecules can be amplified exponentially starting from as little as a single gene or mRNA copy, from any cell, tissue or species of interest.

The invention additionally provides a nucleic acid that hybridizes under high stringency conditions to the CARD coding portion of any of SEQ ID NOS:11, 187, 96, 98, 100, 102, 85 and 89, such as to any of SEQ ID NOS: 168, 170, 172 and 178. The invention also provides a nucleic acid having a nucleotide sequence substantially the same as set that forth in any of SEQ ID 11, 167, 187, 169, 171, 173, 175, 96, 98, 100, 102, 177, 179, 181, 183, 85 and 89.

The invention also provides a method for identifying nucleic acids encoding a mammalian CARD-containing polypeptide by contacting a sample containing nucleic acids with one or more invention nucleic acid molecules or oligonucleotides, wherein the contacting is effected under high stringency hybridization conditions, and identifying a nucleic acid that hybridizes to the oligonucleotide. The invention additionally provides a method of detecting a CARD-encoding nucleic acid molecule in a sample by contacting the sample with two or more invention oligonucleotides, amplifying a nucleic acid molecule, and detecting the amplification. The amplification can be performed, for example, using PCR. The invention further provides oligonucleotides that function as single stranded nucleic acid primers for amplification of a CARD-encoding nucleic acid, wherein the primers comprise a nucleic acid sequence derived from the nucleic acid sequences set forth as SEQ ID NOS:11, 187, 96, 98, 100, 102, 85 and 89.

In accordance with a further embodiment of the present invention, optionally labeled CARD-encoding cDNAs, or fragments thereof, can be employed to probe library(ies) such as cDNA, genomic, BAC, and the like for predominant nucleic acid sequences or additional nucleic acid sequences encoding novel CARD-containing polypeptides. Construction and screening of suitable mammalian cDNA libraries, including human cDNA libraries, is well-known in the art, as demonstrated, for example, in Ausubel et al., supra. Screening of such a cDNA library is initially carried out under low-stringency conditions, which comprise a temperature of less than about 42° C., a formamide concentration of less than about 50%, and a moderate to low salt concentration.

Probe-based screening conditions can comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Hybridization conditions are selected which allow the identification of sequences having at least 70% homology with the probe, while discriminating against sequences which have a lower degree of homology with the probe. As a result, nucleic acids having substantially the same nucleotide sequence as any of SEQ ID NOS:11, 167, 187, 169, 171, 173, 175, 96, 98, 100, 102, 177, 179, 181, 183, 85 and 89 are obtained.

As used herein, a nucleic acid "probe" is single-stranded nucleic acid, or analog thereof, that has a sequence of nucleotides that includes at least 15, at least 20, at least 50, at least 100, at least 200, at least 300, at least 400, or at least 500 contiguous bases that are substantially the same as, or the complement of, any contiguous bases set forth in any of SEQ ID NOS:11, 187, 96, 98, 100, 102, 85 and 89. In addition, the entire cDNA encoding region of an invention CARD-containing polypeptide, or an entire sequence substantially the same as SEQ ID NOS:11, 187, 96, 98, 100, 102, 85 and 89 can be used as a probe. Probes can be labeled by methods well-known in the art, as described hereinafter, and used in various diagnostic kits.

The invention additionally provides an oligonucleotide comprising between 15 and 300 contiguous nucleotides of any of SEQ ID NOS:11, 187, 96, 98, 100, 102, 85 and 89 or the anti-sense strand thereof. As used herein, the term "oligonucleotide" refers to a nucleic acid molecule that includes at least 15 contiguous nucleotides from a reference nucleotide sequence, can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, up to 350 contiguous nucleotides from the reference nucleotide sequence. The reference nucleotide sequence can be the sense strand or the anti-sense strand.

The oligonucleotides of the invention that contain at least 15 contiguous nucleotides of a reference CARD-encoding nucleotide sequence are able to hybridize to CARD-encoding nucleotide sequences under moderately stringent hybridization conditions and thus can be advantageously used, for example, as probes to detect CARD-encoding DNA or RNA in a sample, and to detect splice variants thereof; as sequencing or PCR primers; as antisense reagents to block transcription of CARD-encoding RNA in cells; or in other applications known to those skilled in the art in which hybridization to a CARD-encoding nucleic acid molecule is desirable.

In accordance with another embodiment of the invention, a method is provided for identifying nucleic acids encoding a CARD-containing polypeptide. The method comprises contacting a sample containing nucleic acids with an invention probe or an invention oligonucleotide, wherein said contacting is effected under high stringency hybridization conditions, and identifying nucleic acids which hybridize thereto. Methods for identification of nucleic acids encoding a CARD-containing polypeptide are disclosed herein and exemplified in the Examples.

Also provided in accordance with present invention is a method for identifying a CARD-encoding nucleotide sequence comprising the steps of using a CARD-encoding nucleotide sequence selected from SEQ ID NOS:11, 167, 187, 169, 171, 173, 175, 96, 98, 100, 102, 177, 179, 181, 183, 85 and 89 to identify a candidate CARD-encoding nucleotide sequence and verifying the candidate CARD-encoding nucleotide sequence by aligning the candidate sequence with known CARD-encoding nucleotide sequences, where a conserved CARD domain sequence or a predicted three dimensional polypeptide structure similar to a known CARD domain three dimensional structure confirms the candidate sequence as a CARD-encoding sequence. Methods for identifying CARD-encoding sequences are provided herein (See Examples).

It is understood that a CARD-encoding nucleic acid molecule of the invention, as used herein, specifically excludes previously known nucleic acid molecules consisting of nucleotide sequences having identity with the CARD-encoding nucleotide sequence (SEQ ID NOS:11, 167, 187, 169, 171, 173, 175, 96, 98, 100, 102, 177, 179, 181, 183, 85 and 89), such as Expressed Sequence Tags (ESTs), Sequence Tagged Sites (STSs) and genomic fragments, deposited in public databases such as the nr, dbest, dbsts, gss and htgs databases, which are available for searching at http://www.ncbi.nlm.nih.gov/blast/.

In particular, an invention CARD-encoding nucleic acid molecule excludes the exact, specific and complete nucleic acid molecule sequence corresponding to any of the nucleotide sequences having the Genbank (gb), EMBL (emb) or DDBJ (dbj) accession numbers described below. Accession numbers specifically excluded include GI:6165147 (Phase-1), AC007728 (Phase-1), NT-002476 (Phase-1), AC010968 (Phase-1), AP001153, AC022468 (Phase-1), GI:6253000 (Phase-1), AC0097959 (Phase-1), GI:6497652 (Phase-1) (contig:23086:40635), GI:6497652 (Phase-1) (contig:41136: 57024), AC023068 (Phase-1), W58453, AA257158, AA046000, AW085161, AI189838, AA418021, AA046105, W58488, AA418193, AA257066, AI217611, AW295205, AI023795, AL389934, AA070591, AA070591, AC027011, AP002787, AQ889169, AV719179, AI263294, AV656315, AW337918, BF207840, AW418826, BK903662, AI023795, H25984, AL121653 and NT_005194.1. The human contig referenced as GenBank accession No. AC007608 is also specifically excluded from a CARD encoding nucleic acid molecule. The genomic contigs referenced as GenBank accession numbers GI 5001450, GI 8575872 and GI 9795562 are also specifically excluded from invention nucleic acid molecules. Since one of skill in the art will realize that the above-recited excluded sequences may be revised at a later date, the skilled artisan will recognize that the above-recited sequences are excluded as they stand on the priority date of this application.

The isolated nucleic acid molecules of the invention can be used in a variety of diagnostic and therapeutic applications.

For example, the isolated nucleic acid molecules of the invention can be used as probes, as described above; as templates for the recombinant expression of CARD-containing polypeptides; or in screening assays such as two-hybrid assays to identify cellular molecules that bind CARD-containing polypeptides.

The invention thus provides methods for detecting a CARD-encoding nucleic acid in a sample. The methods of detecting a CARD-encoding nucleic acid in a sample can be either qualitative or quantitative, as desired. For example, the presence, abundance, integrity or structure of a CARD-encoding nucleic acid can be determined, as desired, depending on the assay format and the probe used for hybridization or primer pair chosen for application.

Useful assays for detecting a CARD-containing nucleic acid based on specific hybridization with an isolated invention oligonucleotide are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

Useful assays for detecting a CARD-encoding nucleic acid in a sample based on amplifying a CARD-encoding nucleic acid with two or more invention oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified CARD-encoding nucleic acid can be sequenced to detect mutations and mutational hot-spots, and specific assays for large-scale screening of samples to identify such mutations can be developed.

Also provided are antisense-nucleic acids having a sequence capable of binding specifically with full-length or any portion of an mRNA that encodes CARD-containing polypeptides so as to prevent translation of the mRNA. The antisense-nucleic acid can have a sequence capable of binding specifically with any portion of the sequence of the cDNA encoding CARD-containing polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

The present invention provides means to alter levels of expression of CARD-containing polypeptides by recombinantly expressing CARD-containing anti-sense nucleic acids or employing synthetic anti-sense nucleic acid compositions (hereinafter SANC) that inhibit translation of mRNA encoding these polypeptides. Synthetic oligonucleotides, or other antisense-nucleic acid chemical structures designed to recognize and selectively bind to mRNA are constructed to be complementary to full-length or portions of a CARD-encoding strand, including nucleotide sequences substantially the same as SEQ ID NOS:11, 187, 96, 98, 100, 102, 85 and 89.

The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC, which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed above. The SANC is also designed to recognize and selectively bind to target mRNA sequence, which can correspond to a sequence contained within the sequences shown in SEQ ID NOS:11, 187, 96, 98, 100, 102, 85 and 89. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp. 40).

The invention further provides a method of altering the level of a biochemical process modulated by a CARD-containing polypeptide by introducing an antisense nucleotide sequence into the cell, wherein the antisense nucleotide sequence specifically hybridizes to a CARD-encoding nucleic acid molecule, wherein the hybridization reduces or inhibits the expression of the CARD-containing polypeptide in the cell. The use of anti-sense nucleic acids, including recombinant anti-sense nucleic acids or SANCs, can be advantageously used to inhibit cell death.

Compositions comprising an amount of the antisense-nucleic acid of the invention, effective to reduce expression of CARD-containing polypeptides by entering a cell and binding specifically to CARD-encoding mRNA so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. For example, the structure can be part of a protein known to bind to a cell-type specific receptor such as a tumor.

Antisense-nucleic acid compositions are useful to inhibit translation of mRNA encoding invention polypeptides. Synthetic oligonucleotides, or other antisense chemical structures are designed to bind to CARD-encoding mRNA and inhibit translation of mRNA and are useful as compositions to inhibit expression of CARD-encoding genes or CARD-associated polypeptide genes in a tissue sample or in a subject.

The invention also provides vectors containing the CARD-encoding nucleic acids of the invention. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra, 2000). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a CARD-encoding nucleic acid molecule and for recombinantly expressing a CARD-containing polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing CARD-encoding nucleic acids of the invention. The recombinant cells are generated by introducing into a host cell a vector containing a CARD-encoding nucleic acid molecule. The recombinant cells are transducted, transfected or otherwise genetically modified. Exemplary host cells that can be used to express recombinant CARD molecules include mammalian primary cells; established mammalian cell lines, such as COS, CHO, HeLa, NIH3T3, HEK 293 and PC12 cells; amphibian cells, such as Xenopus embryos and oocytes and other vertebrate cells. Exemplary host cells also include insect cells such as Drosophila, yeast cells such as Saccharomyces cerevisiae, Saccharomyces pombe, or Pichia pastoris, and prokaryotic cells such as Escherichia coli. Additional host cells can be obtained, for example, from TCC (Manassas, Va.).

In one embodiment, CARD-encoding nucleic acids can be delivered into mammalian cells, either in vivo or in vitro using suitable vectors well-known in the art. Suitable vectors for delivering a CARD-containing polypeptide, or a functional fragment thereof to a mammalian cell, include viral vectors such as retroviral vectors, adenovirus, adeno-associated virus, lentivirus, herpesvirus, as well as non-viral vectors such as plasmid vectors. Such vectors are useful for providing therapeutic amounts of a CARD-containing polypeptide (see, for example, U.S. Pat. No. 5,399,346, issued Mar. 21, 1995). Delivery of CARD polypeptides or nucleic acids therapeutically can be particularly useful when targeted to a tumor cell, thereby inducing apoptosis in tumor cells. In addition, where it is desirable to limit or reduce the in vivo expression of a CARD-containing polypeptide, the introduction of the antisense strand of the invention nucleic acid is contemplated.

Viral based systems provide the advantage of being able to introduce relatively high levels of the heterologous nucleic acid into a variety of cells. Suitable viral vectors for introducing an invention CARD-encoding nucleic acid into mammalian cells are well known in the art. These viral vectors include, for example, Herpes simplex virus vectors (Geller et al., *Science,* 241:1667-1669 (1988)); vaccinia virus vectors (Piccini et al., *Meth. Enzymology,* 153:545-563 (1987)); cytomegalovirus vectors (Mocarski et al., in *Viral Vectors,* Y. Gluzman and S. H. Hughes, Eds., Cold Spring Harbor Laboratory, Cold Spring Harbor, N.Y., 1988, pp. 78-84)); Moloney murine leukemia virus vectors (Danos et al., *Proc. Natl. Acad. Sci. USA,* 85:6460-6464 (1988); Blaese et al., *Science,* 270: 475-479 (1995); Onodera et al., *J. Virol.,* 72:1769-1774 (1998)); adenovirus vectors (Berkner, *Biotechnicrues,* 6:616-626 (1988); Cotten et al., *Proc. Natl. Acad. Sci. USA,* 89:6094-6098 (1992); Graham et al., *Meth. Mol. Biol.,* 7:109-127 (1991); Li et al., *Human Gene Therapy,* 4:403-409 (1993); Zabner et al., *Nature Genetics,* 6:75-83 (1994)); adeno-associated virus vectors (Goldman et al., *Human Gene Therapy,* 10:2261-2268 (1997); Greelish et al., *Nature Med.,* 5:439-443 (1999); Wang et al., *Proc. Natl. Acad. Sci. USA,* 96:3906-3910 (1999); Snyder et al., *Nature Med.,* 5:64-70 (1999); Herzog et al., *Nature Med.,* 5:56-63 (1999)); retrovirus vectors (Donahue et al., *Nature Med.,* 4:181-186 (1998); Shackleford et al., *Proc. Natl. Acad. Sci. USA,* 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., *Nature Genetics,* 17:314-317 (1997)).

For example, in one embodiment of the present invention, adenovirus-transferrin/polylysine-DNA (TfAdp1-DNA) vector complexes (Wagner et al., *Proc. Natl. Acad. Sci. USA,* 89:6099-6103 (1992); Curiel et al., *Hum. Gene Ther.,* 3:147-154 (1992); Gao et al., *Hum. Gene Ther.,* 4:14-24 (1993)) are employed to transduce mammalian cells with heterologous CARD-encoding nucleic acid. Any of the plasmid expression vectors described herein may be employed in a TfAdp1-DNA complex.

Vectors useful for therapeutic administration of a CARD-encoding nucleic acid can contain a regulatory element that provides tissue specific or inducible expression of an operatively linked nucleic acid. One skilled in the art can readily determine an appropriate tissue-specific promoter or enhancer that allows expression of a CARD polypeptide or nucleic acid in a desired tissue. Any of a variety of inducible promoters or enhancers can also be included in the vector for regulatable expression of a CARD polypeptide or nucleic acid. Such inducible systems, include, for example, tetracycline inducible system (Gossen & Bizard, Proc. *Natl. Acad. Sci. USA,* 89:5547-5551 (1992); Gossen et al., *Science,* 268: 1766-1769 (1995); Clontech, Palo Alto, Calif.); metalothionein promoter induced by heavy metals; insect steroid hormone responsive to ecdysone or related steroids such as muristerone (No et al., *Proc. Natl. Acad. Sci. USA,* 93:3346-3351 (1996); Yao et al., *Nature,* 366:476-479 (1993); Invitrogen, Carlsbad, Calif.); mouse mammory tumor virus (MMTV) induced by steroids such as glucocortocoid and estrogen (Lee et al., *Nature,* 294:228-232 (1981); and heat shock promoters inducible by temperature changes.

An inducible system particularly useful for therapeutic administration utilizes an inducible promoter that can be regulated to deliver a level of therapeutic product in response to a given level of drug administered to an individual and to have little or no expression of the therapeutic product in the absence of the drug. One such system utilizes a Gal4 fusion that is inducible by an antiprogestin such as mifepristone in a modified adenovirus vector (Burien et al., *Proc. Natl. Acad. Sci. USA,* 96:355-360 (1999). Another such inducible system utilizes the drug rapamycin to induce reconstitution of a transcriptional activator containing rapamycin binding domains of % FKBP12 and FRAP in an adeno-associated virus vector (Ye et al., *Science,* 283:88-91 (1999)). It is understood that any combination of an inducible system can be combined in any suitable vector, including those disclosed herein. Such a regulatable inducible system is advantageous because the level of expression of the therapeutic product can be controlled by the amount of drug administered to the individual or, if desired, expression of the therapeutic product can be terminated by stopping administration of the drug.

The invention also provides a method for expression of a CARD-containing polypeptide by culturing cells containing a CARD-encoding nucleic acid under conditions suitable for expression of a CARD-containing polypeptide. Thus, there is provided a method for the recombinant production of a CARD-containing polypeptide of the invention by expressing the CARD-encoding nucleic acid sequences in suitable host cells. Recombinant DNA expression systems that are suitable to produce a CARD-containing polypeptide described herein are well-known in the art (see, for example, Ausubel et al., supra, 2000). For example, the above-described nucleotide sequences can be incorporated into vectors for further manipulation. As used herein, vector refers to a recombinant DNA or RNA plasmid or virus containing discrete elements that are used to introduce heterologous DNA into cells for either expression or replication thereof.

The invention additionally provides an isolated anti-CARD antibody having specific reactivity with a invention CARD-containing polypeptide. The anti-CARD antibody can be a monoclonal antibody or a polyclonal antibody. The invention further provides cell lines producing monoclonal antibodies having specific reactivity with an invention CARD-containing protein.

The invention thus provides antibodies that specifically bind a CARD-containing polypeptide. As used herein, the term "antibody" is used in its broadest sense to include polyclonal and monoclonal antibodies, as well as antigen binding fragments of such antibodies. With regard to an anti-CARD antibody of the invention, the term "antigen" means a native or synthesized CARD-containing polypeptide or fragment thereof. An anti-CARD antibody, or antigen binding fragment of such an antibody, is characterized by having specific binding activity for a CARD polypeptide or a peptide portion thereof of at least about $1 \times 10^5$ M$^{-1}$. Thus, Fab, F(ab')$_2$, Fd and Fv fragments of an anti-CARD antibody, which retain specific binding activity for a CARD-containing polypeptide, are included within the definition of an antibody. Specific binding activity of a CARD-containing polypeptide can be readily determined by one skilled in the art, for example, by comparing the binding activity of an anti-CARD antibody to a CARD-containing polypeptide versus a reference polypeptide that is not a CARD-containing polypeptide. Methods of preparing polyclonal or monoclonal antibodies are well known to those skilled in the art (see, for example, Harlow and Lane, *Antibodies: A Laboratory Manual,* Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Engineering: A practical approach* (IRL Press 1992); Borrabeck, *Antibody Engineering,* 2d ed. (Oxford University Press 1995)).

Anti-CARD antibodies can be raised using a CARD immunogen such as an isolated CARD-containing polypeptide having substantially the same amino acid sequence as SEQ ID NOS:12, 188, 97, 99, 101, 103, 86 and 90, or a fragment thereof, which can be prepared from natural sources or produced recombinantly, or a peptide portion of the CARD-containing polypeptide. Such peptide portions of a CARD-containing polypeptide are functional antigenic fragments if the antigenic peptides can be used to generate a CARD-specific antibody. A non-immunogenic or weakly immunogenic CARD-containing polypeptide or portion thereof can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art (see, for example, Harlow and Lane, supra, 1988). An immunogenic CARD-containing polypeptide fragment can also be generated by expressing the peptide as a fusion protein, for example, to glutathione S transferase (GST), polyHis or the like. Methods for expressing peptide fusions are well known to those skilled in the art (Ausubel et al., supra, (2000)).

The invention further provides a method for detecting the presence of a human CARD-containing polypeptide in a sample by contacting a sample with a CARD-specific antibody, and detecting the presence of specific binding of the antibody to the sample, thereby detecting the presence of a human CARD-containing polypeptide in the sample. CARD-specific antibodies can be used in diagnostic methods and systems to detect the level of CARD-containing polypeptide present in a sample. As used herein, the term "sample" is intended to mean any biological fluid, cell, tissue, organ or portion thereof, that includes or potentially includes CARD nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or polypeptide preparation.

CARD-specific antibodies can also be used for the immunoaffinity or affinity chromatography purification of an invention CARD-containing polypeptide. In addition, methods are contemplated herein for detecting the presence of an invention CARD-containing polypeptide in a cell, comprising contacting the cell with an antibody that specifically binds to CARD-containing polypeptides under conditions permitting binding of the antibody to the CARD-containing polypeptides, detecting the presence of the antibody bound to the CARD-containing polypeptide, and thereby detecting the presence of invention polypeptides in a cell. With respect to the detection of such polypeptides, the antibodies can be used for in vitro diagnostic or in vivo imaging methods.

Immunological procedures useful for in vitro detection of target CARD-containing polypeptides in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra, 1988; Harlow and Lane, *Using Antibodies: A Laboratory Manual*, Cold Spring Harbor Press (1999)).

An antibody can be made detectable by various means well known in the art. For example, a detectable marker can be directly attached to the antibody or indirectly attached using, for example, a secondary agent that recognizes the CARD specific antibody. Useful markers include, for example, radionucleotides, enzymes, binding proteins such as biotin, fluorogens, chromogens and chemiluminescent labels.

An antibody can also be detectable by, for example, a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189-231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3-46 (1981). Conventional means of protein conjugation or coupling by activated functional groups are particularly applicable. See, for example, Aurameas et al., *Scand. J. Immunol.*, Vol. 8, Suppl. 7:7-23 (1978), Rodwell et al., *Biotech.*, 3:889-894 (1984), and U.S. Pat. No. 4,493,795.

In addition to detecting the presence of a CARD-containing polypeptide, invention anti-CARD antibodies are contemplated for use herein to alter the activity of the CARD-containing polypeptide in living animals, in humans, or in biological tissues or fluids isolated therefrom. The term "alter" refers to the ability of a compound such as a CARD-containing polypeptide, a CARD-encoding nucleic acid, an agent or other compound to increase or decrease biological activity which is modulated by the compound, by functioning as an agonist or antagonist of the compound. Accordingly, compositions comprising a carrier and an amount of an antibody having specificity for CARD-containing polypeptides effective to block naturally occurring ligands or other CARD-associated polypeptides from binding to invention CARD-containing polypeptides are contemplated herein. For example, a monoclonal antibody directed to an epitope of an invention CARD-containing polypeptide, including an amino acid sequence substantially the same as SEQ ID 12, 188, 97, 99, 101, 103, 86 and 90, can be useful for this purpose.

The present invention further provides transgenic non-human mammals that are capable of expressing exogenous nucleic acids encoding CARD-containing polypeptides. As employed herein, the phrase "exogenous nucleic acid" refers to nucleic acid sequence which is not native to the host, or which is present in the host in other than its native environment, for example, as part of a genetically engineered DNA construct. In addition to naturally occurring CARD-containing polypeptide levels, a CARD-containing polypeptide of the invention can either be overexpressed or underexpressed in transgenic mammals, for example, underexpressed in a knock-out animal.

Also provided are transgenic non-human mammals capable of expressing CARD-encoding nucleic acids so mutated as to be incapable of normal activity. Therefore, the transgenic non-human mammals do not express native CARD-containing polypeptide or have reduced expression of native CARD-containing polypeptide. The present invention also provides transgenic non-human mammals having a genome comprising antisense nucleic acids complementary to CARD-encoding nucleic acids, placed so as to be transcribed into antisense mRNA complementary to CARD-encoding mRNA, which hybridizes to the mRNA and, thereby, reduces the translation thereof. The nucleic acid can additionally comprise an inducible promoter and/or tissue specific regulatory elements, so that expression can be induced, or restricted to specific cell types.

Animal model systems useful for elucidating the physiological and behavioral roles of CARD-containing polypeptides are also provided, and are produced by creating transgenic animals in which the expression of the CARD-containing polypeptide is altered using a variety of techniques. Examples of such techniques include the insertion of normal or mutant versions of nucleic acids encoding a CARD-containing polypeptide by microinjection, retroviral infection or other means well known to those skilled in the art, into appropriate fertilized embryos to produce a transgenic animal, see, for example, Hogan et al., *Manipulating the Mouse Embryo: A Laboratory Manual* (Cold Spring Harbor Laboratory, (1986)). Transgenic animal model systems are useful for in vivo screening of compounds for identification of specific ligands, such as agonists or antagonists, which activate or inhibit a biological activity.

Also contemplated herein, is the use of homologous recombination of mutant or normal versions of CARD-encoding genes with the native gene locus in transgenic animals, to alter the regulation of expression or the structure of CARD-containing polypeptides by replacing the endogeneous gene with a recombinant or mutated CARD-encoding gene. Methods for producing a transgenic non-human mammal including a gene knock-out non-human mammal, are well known to those skilled in the art (see, Capecchi et al., *Science* 244:1288 (1989); Zimmer et al., *Nature* 338:150 (1989); Shastry, *Experentia*, 51:1028-1039 (1995); Shastry, *Mol. Cell. Biochem.*, 181:163-179 (1998); and U.S. Pat. No. 5,616,491, issued Apr. 1, 1997, No. 5,750,826, issued May 12, 1998, and No. 5,981,830, issued Nov. 9, 1999).

In addition to homologous recombination, additional methods such as microinjection can be used which add genes to the host genome without removing host genes. Microinjection can produce a transgenic animal that is capable of expressing both endogenous and exogenous CARD-containing polypeptides. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit CARD-containing polypeptide responses.

In accordance with another embodiment of the invention, a method is provided for identifying a CARD-associated polypeptide (CAP). The method is carried out by contacting an invention CARD-containing polypeptide with a candidate CAP and detecting association of the CARD-containing polypeptide with the CAP.

As used herein, the term "CARD-associated polypeptide" or "CAP" means a polypeptide that can specifically bind to the CARD-containing polypeptides of the invention, or to any functional fragment of a CARD-containing polypeptide of the invention. Because CARD-containing polypeptides of the invention contain domains which can self-associate, CARD-containing polypeptides are encompassed by the term CAP. An exemplary CAP is a protein or a polypeptide portion of a protein that can bind an NB-ARC (NACHT), CARD, LRR or ANGIO-R domain of an invention CARD-containing polypeptide. A CAP can be identified, for example, using in vitro protein binding assays similar to those described in, for example, Ausubel et al., supra, 2000, and by in vivo methods including methods such as yeast two-hybrid assays, or other protein-interaction assays and methods known in the art.

Normal association of CARD-containing polypeptide and a CAP polypeptide in a cell can be altered due, for example, to the expression in the cell of a variant CAP or CARD-containing polypeptide, respectively, either of which can compete with the normal binding function of a CARD-containing polypeptide and, therefore, can decrease the association of CAP and CARD-containing polypeptides in a cell. The term "variant" is used generally herein to mean a polypeptide that is different from the CAP or CARD-containing polypeptide that normally is found in a particular cell type. Thus, a variant can include a mutated protein or a naturally occurring protein, such as an isoform, that is not normally found in a particular cell type.

CARD-containing polypeptides and CARD-associated polypeptides of the invention can be characterized, for example, using in vitro binding assays or the yeast two hybrid system. An in vivo transcription activation assay such as the yeast two hybrid system is particularly useful for identifying and manipulating the association of proteins. In addition, the results observed in such an assay likely mirror the events that naturally occur in a cell. Thus, the results obtained in such an in vivo assay can be predictive of results that can occur in a cell in a subject such as a human subject.

A transcription activation assay such as the yeast two hybrid system is based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two proteins. The DNA-binding domain and trans-activation domain can be bridged, for example, by expressing the DNA-binding domain and trans-activation domain as fusion proteins (hybrids), provided that the proteins that are fused to the domains can associate with each other. The non-covalent bridging of the two hybrids brings the DNA-binding and trans-activation domains together and creates a transcriptionally competent complex. The association of the proteins is determined by observing transcriptional activation of a reporter gene.

The yeast two hybrid systems exemplified herein use various strains of S. cerevisiae as host cells for vectors that express the hybrid proteins. A transcription activation assay also can be performed using, for example, mammalian cells. However, the yeast two hybrid system is particularly useful due to the ease of working with yeast and the speed with which the assay can be performed. For example, yeast host cells containing a lacZ reporter gene linked to a LexA operator sequence can be used to demonstrate that a CARD domain of an invention CARD-containing polypeptide can interact with itself or other CARD-containing polypeptides. For example, the DNA-binding domain can consist of the LexA DNA-binding domain, which binds the LexA promoter, fused to the CARD domain of a CARD-containing polypeptide of the invention and the trans-activation domain can consist of the B42 acidic region separately fused to several cDNA sequences which encode known CARD-containing polypeptides. When the LexA domain is non-covalently bridged to a trans-activation domain fused to a CARD-containing polypeptide, the association can activate transcription of the reporter gene.

A CAP; for example, a CARD-containing polypeptide, an NB-ARC-containing polypeptide or a LRR-containing polypeptide, also can be identified using well known in vitro assays, for example, an assay utilizing a glutathione-5-transferase (GST) fusion protein. Such an in vitro assay provides a simple, rapid and inexpensive method for identifying and isolating a CAP. Such an in vitro assay is particularly useful in confirming results obtained in vivo and can be used to characterize specific binding domains of a CAP. For example, a GST can be fused to a CARD-containing polypeptide of the invention, and expressed and purified by binding to an affinity matrix containing immobilized glutathione. If desired, a sample that can contain a CAP or active fragments of a CAP can be passed over an affinity column containing bound GST/CARD and a CAP that binds to a CARD-containing polypeptide can be obtained. In addition, GST/CARD can be used to screen a cDNA expression library, wherein binding of the GST/CARD fusion protein to a clone indicates that the clone contains a cDNA encoding a CAP.

Thus, one of skill in the art will recognize that using the CARD-containing polypeptides described herein, a variety of methods, such as protein purification, protein interaction cloning, or protein mass-spectrometry, can be used to identify a CAP.

Although the term "CAP" is used generally, it should be recognized that a CAP that is identified using the novel polypeptides described herein can be a fragment of a protein. Thus, as used herein, a CAP also includes a polypeptide that specifically associates to a portion of an invention CARD-containing polypeptide that does not include a CARD domain. For example, a CAP can associate with the NB-ARC domain of CLAN or CARD3X. As used herein, a "candidate CAP" refers to a polypeptide containing a polypeptide sequence know or suspected of binding one or more CARD-containing polypeptides of the invention. Thus, a CAP can represent a full-length protein or a CARD-associating fragment thereof. Since a CAP polypeptide can be a full-length protein or a CARD-associating fragment thereof, one of skill in the art will recognize that a CAP-encoding nucleic acid, such as the genomic sequence, an mRNA sequence or a cDNA sequence need not encode the full-length protein. Thus, a cDNA can encode a polypeptide that is a fragment of a full-length CAP which, nevertheless, binds one or more invention CARD-containing polypeptides. It is also within the scope of the invention that a full-length CAP can assume a conformation that does not, absent some post-translational modification, bind a CARD-containing polypeptide of the invention, due, for example, to steric blocking of the binding site. Thus, a CAP can be a protein or a polypeptide portion of a protein that can bind one of the CARD-containing polypeptides of the invention. Also, it should be recognized that a CAP can be identified by using a minimal polypeptide derived from the sequences of the CARD-containing polypeptides of the invention, and does not necessarily require that the full-length molecules be employed for identifying such CAPs.

Since CARD-containing polypeptides can be involved in apoptosis, the association of a CAP with a CARD-containing polypeptide can affect the sensitivity or resistance of a cell to apoptosis or can induce or block apoptosis induced by external or internal stimuli. The identification of various CAPs by use of known methods can be used to determine the function of these CAPs in cell death or signal transduction pathways controlled by CARD-containing polypeptides, allowing for the development of assays that are useful for identifying agents that effectively alter the association of a CAP with a CARD-containing polypeptide. Such agents can be useful for providing effective therapy for conditions caused, at least in part, by insufficient apoptosis, such as a cancer, autoimmune disease or certain viral infections. Such agents can also be useful for providing an effective therapy for diseases where excessive apoptosis is known to occur, such as stroke, heart failure, or AIDS.

Assays of the invention can be used for identification of agents that alter the self-association of the CARD-containing polypeptides of the invention. Thus, the methods of the invention can be used to identify agents that alter the self-association of CARD2X, CARD3X, CLAN A, CLAN B, CLAN C, CLAN D, COP-1 and COP-2 (set forth in SEQ ID NOS: 12, 188, 97, 99, 101, 103, 86 and 90) via their CARD domains, NB-ARC domains, LRR domains, or other domains within these polypeptides.

The ATP-binding and hydrolysis of the NB-ARC domains can be critical for function of a NAC polypeptide, for example, by altering the oligomerization of the NAC. Thus, agents that interfere with or enhance ATP or nucleotide binding and/or hydrolysis by the NB-ARC domain of a NAC polypeptide of the invention, such as CLAN (SEQ ID NOS: 97, 99, 101 or 103) can also be useful for altering the activity of these polypeptides in cells.

A further embodiment of the invention provides a method to identify agents that can effectively alter CARD-containing polypeptide activity, for example the ability of CARD-containing polypeptides to associate with one or more heterologous proteins. Thus, the present invention provides a screening assay useful for identifying an effective agent, which can alter the association of a CARD-containing polypeptide with a CARD-associated polypeptide (CAP), such as a heterologous ARD-containing polypeptide. Since CARD-containing polypeptides are involved in biochemical processes such as apoptosis, the identification of such effective agents can be useful for altering the level of a biochemical process such as apoptosis in a cell, for example in a cell of a subject having a pathology characterized by an increased or decreased level of apoptosis.

Further, effective agents can be useful for alteration of other biochemical process modulated by a CARD-containing polypeptide of the invention. Additional biochemical processes modulated by CARD-containing polypeptide include, for example, NF-kB induction, cytokine processing, cytokine receptor signaling, cJUN N-terminal kinase induction, and caspase-mediated proteolysis activation/inhibition, transcription, inflammation and cell adhesion.

As used herein, the term "agent" means a chemical or biological molecule such as a simple or complex organic molecule, a peptide, a peptido-mimetic, a polypeptide, a protein or an oligonucleotide that has the potential for altering the association of a CARD-containing polypeptide with a heterologous protein or altering the ability of a CARD-containing polypeptide to self-associate or altering the ligand binding or catalytic activity of a CARD-containing polypeptide. An exemplary ligand binding activity is nucleotide binding activity, such as ADP or ATP binding activity; and exemplary catalytic activities are nucleotide hydrolytic activity and proteolytic activity. In addition, the term "effective agent" is used herein to mean an agent that is confirmed as capable of altering the association of a CARD-containing polypeptide with a heterologous protein or altering the ability of a CARD-containing polypeptide to self-associate or altering the ligand binding or catalytic activity of a CARD-containing polypeptide. For example, an effective agent may be an anti-CARD antibody, a CARD-associated polypeptide, a caspase inhibitor, and the like.

As used herein, the term "alter the association" means that the association between two specifically interacting polypeptides either is increased or decreased due to the presence of an effective agent. As a result of an altered association of CARD-containing polypeptide with another polypeptide in a cell, the activity of the CARD-containing polypeptide or the CAP can be increased or decreased, thereby altering a biochemical process, for example, the level of apoptosis in the cell. As used herein, the term "alter the activity" means that the agent can increase or decrease the activity of a CARD-containing polypeptide in a cell, thereby modulating a biochemical process in a cell, for example, the level of apoptosis in the cell. Similarly, the term "alter the level" of a biological process modulated by a CARD-containing polypeptide refers to an increase or decrease a biochemical process which occurs upon altering the activity of a CARD-containing polypeptide. For example, an effective agent can increase or decrease the CARD:CARD-associating activity of a CARD-containing polypeptide, which can result in decreased apoptosis. In another example, alteration of the ATP hydrolysis activity can modulate the ability of the NB-ARC domain of a CARD-containing polypeptide to associate with other NB-ARC-containing polypeptides, such as Apaf-1, thereby altering any process effected by such association between a CARD-containing polypeptide and an NB-ARC-containing polypeptide.

An effective agent can act by interfering with the ability of a CARD-containing polypeptide to associate with another polypeptide, or can act by causing the dissociation of a CARD-containing polypeptide from a complex with a CARD-associated polypeptide, wherein the ratio of bound CARD-containing polypeptide to free CARD-containing polypeptide is related to the level of a biochemical process, such as, apoptosis, in a cell. For example, binding of a ligand to a CAP can allow the CAP, in turn, to bind a specific CARD-containing polypeptide such that all of the specific CARD-containing polypeptide is bound to a CAP, and can result in decreased apoptosis. The association, for example, of a CARD-containing polypeptide and a CARD-containing polypeptide can result in activation or inhibition of the NB-ARC:NB-ARC-associating activity of a CARD-containing polypeptide. In the presence of an effective agent, the association of a CARD-containing polypeptide and a CAP can be altered, which can, for example, alter the activation of caspases in the cell. As a result of the altered caspase activation, the level of apoptosis in a cell can be increased or decreased. Thus, the identification of an effective agent that alters the association of a CARD-containing polypeptide with another polypeptide can allow for the use of the effective agent to increase or decrease the level of a biological process such as apoptosis.

An effective agent can be useful, for example, to increase the level of apoptosis in a cell such as a cancer cell, which is characterized by having a decreased level of apoptosis as compared to its normal cell counterpart. An effective agent also can be useful, for example, to decrease the level of apoptosis in a cell such as a T lymphocyte in a subject having a viral disease such as acquired immunodeficiency syndrome, which is characterized by an increased level of apoptosis in an infected T cell as compared to a normal T cell. Thus, an effective agent can be useful as a medicament for altering the level of apoptosis in a subject having a pathology characterized by increased or decreased apoptosis. In addition, an effective agent can be used, for example, to decrease the level of apoptosis and, therefore, increase the survival time of a cell such as a hybridoma cell in culture. The use of an effective agent to prolong the survival of a cell in vitro can significantly improve bioproduction yields in industrial tissue culture applications.

A CARD-containing polypeptide that lacks the ability to bind the NB-ARC domain or LRR domain of another polypeptide but retains the ability to self-associate via its CARD domain or to bind to other CARD-containing polypeptides is an example of an effective agent, since the expression of a non-NB-ARC-associating or non-catalytically active CARD-containing polypeptide in a cell can alter the association of a the endogenous CARD-containing polypeptide with itself or with CAPs.

Thus, it should be recognized that a mutation of a CARD-containing polypeptide can be an effective agent, depending, for example, on the normal levels of CARD-containing polypeptide and CARD-associated polypeptide that occur in a particular cell type. In addition, an active fragment of a CARD-containing polypeptide can be an effective agent, provided the active fragment can alter the association of a CARD-containing polypeptide and another polypeptide in a cell. Such active fragments, which can be peptides as small as about five amino acids, can be identified, for example, by screening a peptide library (see, for example, Ladner et al., U.S. Pat. No. 5,223,409) to identify peptides that can bind a CARD-associated polypeptide.

Similarly, a fragment of a CARD-associated polypeptide also can be an effective agent. A fragment of CARD-associated polypeptide can be useful, for example, for decreasing the association of a CARD-containing polypeptide with a CAP in a cell by competing for binding to the CARD-containing polypeptide. A non-naturally occurring peptido-mimetic also can be useful as an effective agent. Such a peptido-mimetic can include, for example, a peptoid, which is peptide-like sequence containing N-substituted glycines, or an oligocarbamate. A peptido-mimetic can be particularly useful as an effective agent due, for example, to having an increased stability to enzymatic degradation in vivo.

In accordance with another embodiment of the present invention, there is provided a method of identifying an effective agent that alters the association of an invention CARD-containing polypeptide with a CARD-associated polypeptide (CAP), by the steps of:

(a) contacting a CARD-containing polypeptide and a CAP polypeptide, under conditions that allow the CARD-containing polypeptide and CAP polypeptide to associate, with an agent suspected of being able to alter the association of the CARD-containing polypeptide and CAP polypeptides; and (b) detecting the altered association of the CARD-containing polypeptide and CAP polypeptide, where the altered association identifies an effective agent.

Methods well-known in the art for detecting the altered association of the CARD-containing polypeptide and CAP polypeptides, for example, measuring protein:protein binding, protein degradation or apoptotic activity can be employed in bioassays described herein to identify agents as agonists or antagonists of CARD-containing polypeptides. As described herein, CARD-containing polypeptides have the ability to self-associate. Thus, methods for identifying effective agents that alter the association of a CARD-containing polypeptide with a CAP are useful for identifying effective agents that alter the ability of a CARD-containing polypeptide to self-associate.

As used herein, "conditions that allow said CARD-containing polypeptide and CAP polypeptide to associate" refers to environmental conditions in which a CARD-containing polypeptide and CAP specifically associate. Such conditions will typically be aqueous conditions, with a pH between 3.0 and 11.0, and temperature below 100° C. Preferably, the conditions will be aqueous conditions with salt concentrations below the equivalent of 1 M NaCl, and pH between 5.0 and 9.0, and temperatures between 0° C. and 50° C. Most preferably, the conditions will range from physiological conditions of normal yeast or mammalian cells, or conditions favorable for carrying out in vitro assays such as immunoprecipitation and GST protein:protein association assays, and the like.

In another embodiment of the invention, a method is provided for identifying agents that modulate a ligand binding or catalytic activity of an invention CARD-containing polypeptide. The method contains the steps of contacting an invention CARD-containing polypeptide with an agent suspected of modulating a ligand binding or catalytic activity of the CARD-containing polypeptide and measuring a ligand binding or catalytic activity of the CARD-containing polypeptide, where modulated ligand binding or catalytic activity identifies the agent as an agent that alters the ligand binding or catalytic activity of a CARD-containing polypeptide.

As used herein in regard to ligand binding or catalytic activity, "modulate" refers to an increase or decrease in ligand binding or catalytic activity. Thus, modulation encompasses inhibition of ligand binding or catalytic activity as well as activation or enhancement of ligand binding or catalytic activity. Exemplary ligand binding activities include nucleotide binding activity. Exemplary catalytic binding activities include nucleotide hydrolysis and proteolysis activities.

Methods for measuring ligand binding or catalytic activities are well known in the art, as disclosed herein. For example, an agent known or suspected of modulating ligand binding or catalytic activity can be contacted with an invention CARD-containing polypeptide in vivo or in vitro, and the ligand binding or catalytic activity can be measured using known methods. For example, enzymatic activity can be measured using a cleavable reporter, where the cleavable reporter generates or alters a measurable signal such as absorption, fluorescence or radioactive decay. Exemplary agents that can modulate ligand binding or catalytic activity include peptides, peptidomimetics and other peptide analogs, non-peptide organic molecules such as naturally occurring protease inhibitors and derivatives thereof, nucleotides and nucleotide analogs, and the like. Such inhibitors can be either reversible or irreversible, as is well known in the art.

Agents that modulate the ligand binding or catalytic activity of a CARD-containing polypeptide identified using the invention methods can be used to modulate the activity of a CARD-containing polypeptide. For example, and agent can modulate the nucleotide binding or nucleotide hydrolytic activity of an NB-ARC domain of a CARD-containing polypeptide. In another example, an agent can modulate the catalytic activity of a protease domain such as a caspase domain. Methods of modulating the ligand binding or catalytic activities of invention CARD-containing proteins can be used in methods of altering biochemical processes modulated by CARD-containing proteins, such as the biochemical processes disclosed herein.

In yet another embodiment of the present invention, there are provided methods for altering ligand binding or catalytic activity of a CARD-containing polypeptide of the invention, the method comprising:

contacting an CARD-containing polypeptide with an effective amount of an agent identified by the herein-described bioassays.

The present invention also provides in vitro screening assays. Such screening assays are particularly useful in that they can be automated, which allows for high through-put screening, for example, of randomly or rationally designed agents such as drugs, peptidomimetics or peptides in order to identify those agents that effectively alter the association of a CARD-containing polypeptide and a CAP or the catalytic or ligand binding activity of a CARD-containing polypeptide and, thereby, alter a biochemical process modulated by a CARD-containing polypeptide such as apoptosis. An in vitro screening assay can utilize, for example, a CARD-containing polypeptide including a CARD-containing fusion protein such as a CARD-glutathione-5-transferase fusion protein. For use in the in vitro screening assay, the CARD-containing polypeptide should have an affinity for a solid substrate as well as the ability to associate with a CARD-associated polypeptide. For example, when a CARD-containing polypeptide is used in the assay, the solid substrate can contain a covalently attached anti-CARD antibody. Alternatively, a GST/CARD fusion protein can be used in the assay and the solid substrate can contain covalently attached glutathione, which is bound by the GST component of the GST/CARD fusion protein. Similarly, a CARD-associated polypeptide, or GST/NB-ARC-containing polypeptide fusion protein can be used in any of a variety of in vitro enzymatic or in vitro binding assays known in the art and described in texts such as Ausubel et al., supra, 2000.

An in vitro screening assay can be performed by allowing a CARD-containing polypeptide, for example, to bind to the solid support, then adding a CARD-associated polypeptide and an agent to be tested. Reference reactions, which do not contain an agent, can be performed in parallel. Following incubation under suitable conditions, which include, for example, an appropriate buffer concentration and pH and time and temperature that permit binding of the particular CARD-containing polypeptide and CARD-associated polypeptide, the amount of protein that has associated in the absence of an agent and in the presence of an agent can be determined. The association of a CARD-associated polypeptide with a CARD-containing polypeptide can be detected, for example, by attaching a detectable moiety such as a radionuclide or a fluorescent label to a CARD-associated polypeptide and measuring the amount of label that is associated with the solid support, wherein the amount of label detected indicates the amount of association of the CARD-associated polypeptide with a CARD-containing polypeptide. An effective agent is determined by comparing the amount of specific binding in the presence of an agent as compared to a reference level of binding, wherein an effective agent alters the association of CARD-containing polypeptide with the CARD-associated polypeptide. Such an assay is particularly useful for screening a panel of agents such as a peptide library in order to detect an effective agent.

Various binding assays to identify cellular proteins that interact with protein binding domains are known in the art and include, for example, yeast two-hybrid screening assays (see, for example, U.S. Pat. Nos. 5,283,173, 5,468,614 and 5,667, 973; Ausubel et al., supra, 2000; Luban et al., *Curr. Opin. Biotechnol.* 6:59-64 (1995)) and affinity column chromatography methods using cellular extracts. By synthesizing or expressing polypeptide fragments containing various CARD-associating sequences or deletions, the CARD binding interface can be readily identified.

Another assay for screening of agents that alter the activity of a CARD-containing polypeptide is based on altering the phenotype of yeast by expressing a CARD-containing polypeptide. In one embodiment, expression of a CARD-containing polypeptide can be inducible (Tao et al., *J. Biol. Chem.* 273:23704-23708 (1998), and the compounds can be screened when CARD-containing polypeptide expression is induced. CARD-containing polypeptides of the invention can also be co-expressed in yeast with CAP polypeptides used to screen for compounds that antagonize the activity of the CARD-containing polypeptide.

Also provided with the present invention are assays to identify agents that alter CARD-containing polypeptide expression. Methods to determine CARD-containing polypeptide expression can involve detecting a change in CARD-containing polypeptide abundance in response to contacting the cell with an agent that modulates CARD-containing polypeptide expression. Assays for detecting changes in polypeptide expression include, for example, immunoassays with CARD-specific antibodies, such as immunoblotting, immunofluorescence, immunohistochemistry and immunoprecipitation assays, as described herein.

As understood by those of skill in the art, assay methods for identifying agents that alter CARD-containing polypeptide activity generally require comparison to a reference. One type of a "reference" is a cell or culture that is treated substantially the same as the test cell or test culture exposed to the agent, with the distinction that the "reference" cell or culture is not exposed to the agent. Another type of "reference" cell or culture can be a cell or culture that is identical to the test cells, with the exception that the "reference" cells or culture do not express a CARD-containing polypeptide. Accordingly, the response of the transfected cell to an agent is compared to the response, or lack thereof, of the "reference" cell or culture to the same agent under the same reaction conditions.

Methods for producing pluralities of agents to use in screening for compounds that alter the activity of a CARD-containing polypeptide, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.,* 2:363-371 (1998); Sofia, *Mol. Divers.* 3:75-94 (1998); Eichler et al., *Med. Res. Rev.* 15:481-496 (1995); and the like. Libraries containing large numbers of natural and synthetic agents also can be obtained from commercial sources. Combinatorial libraries of molecules can be prepared using well known combinatorial chemistry methods (Gordon et al., *J. Med. Chem.* 37: 12331251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997)).

The invention further provides a method of diagnosing or predicting clinical prognosis of a pathology characterized by an increased or decreased level of a CARD-containing polypeptide in a subject. The method includes the steps of (a) obtaining a test sample from the subject; (b) contacting the sample with an agent that can bind a CARD-containing polypeptide of the invention under suitable conditions, wherein the conditions allow specific binding of the agent to the CARD-containing polypeptide; and (c) comparing the amount of the specific binding in the test sample with the amount of specific binding in a reference sample, wherein an increased or decreased amount of the specific binding in the test sample as compared to the reference sample is diagnostic of, or predictive of the clinical prognosis of, a pathology. The agent can be, for example, an anti-CARD antibody, a CARD-associated-polypeptide (CAP), or a CARD-encoding nucleic acid.

Exemplary pathologies for diagnosis or the prediction of clinical prognosis include any of the pathologies described herein, such as neoplastic pathologies (e.g. cancer), autoimmune diseases, and other pathologies related to abnormal cell proliferation or abnormal cell death (e.g. apoptosis), as disclosed herein.

The invention also provides a method of diagnosing cancer or monitoring cancer therapy by contacting a test sample from a patient with a CARD-specific antibody. The invention additionally provides a method of assessing prognosis (e.g., predicting the clinical prognosis) of patients with cancer comprising contacting a test sample from a patient with a CARD-specific antibody.

The invention additionally provides a method of diagnosing cancer or monitoring cancer therapy by contacting a test sample from a patient with a oligonucleotide that selectively hybridizes to a CARD-encoding nucleic acid molecule. The invention further provides a method of assessing prognosis (e.g., predicting the clinical prognosis) of patients with cancer by contacting a test sample from a patient with a oligonucleotide that selectively hybridizes to a CARD-encoding nucleic acid molecule.

The methods of the invention for diagnosing cancer or monitoring cancer therapy using a CARD-specific antibody or oligonucleotide or nucleic acid that selectively hybridizes to a CARD-encoding nucleic acid molecule can be used, for example, to segregate patients into a high risk group or a low risk group for diagnosing cancer or predicting risk of metastasis or risk of failure to respond to therapy. Therefore, the methods of the invention can be advantageously used to determine, for example, the risk of metastasis in a cancer patient, or the risk of an autoimmune disease of a patient, or as a prognostic indicator of survival or disease progression in a cancer patient or patient with an autoimmune disease. One of ordinary skill in the art would appreciate that the prognostic indicators of survival for cancer patients suffering from stage I cancer can be different from those for cancer patients suffering from stage IV cancer. For example, prognosis for stage I cancer patients can be oriented toward the likelihood of continued growth and/or metastasis of the cancer, whereas prognosis for stage IV cancer patients can be oriented toward the likely effectiveness of therapeutic methods for treating the cancer. Accordingly, the methods of the invention directed to measuring the level of or determining the presence of a CARD-containing polypeptide or CARD-encoding nucleic acid can be used advantageously as a prognostic indicator for the presence or progression of a cancer or response to therapy.

The invention further provides methods for introducing a CARD-encoding nucleic acid into a cell in a subject, for example, for gene therapy. Viruses are specialized infectious agents that can elude host defense mechanisms and can infect and propagate in specific cell types. Viral based systems provide the advantage of being able to introduce relatively high levels of the heterologous nucleic acid into a variety of cells. Suitable viral vectors for introducing an invention CARD-encoding nucleic acid into mammalian cells (e.g., vascular tissue segments) are well known in the art. These viral vectors include, for example, Herpes simplex virus vectors (e.g., Geller et al., *Science*, 241:1667-1669 (1988)), Vaccinia virus vectors (e.g., Piccini et al., *Meth. in Enzymology*, 153:545-563 (1987); Cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78-84), Moloney murine leukemia virus vectors (Danos et al., *Proc. Natl. Acad. Sci., USA*, 85:6469 (1980)), adenovirus vectors (e.g., Logan et al., *Proc. Natl. Acad. Sci., USA*, 81:3655-3659 (1984); Jones et al., *Cell*, 17:683-689 (1979); Berkner, *Biotechniues*. 6:616-626 (1988); Cotten et al., *Proc. Natl. Acad. Sci. USA*, 89:6094-6098 (1992); Graham et al., *Meth. Mol. Biol.*, 7:109-127 (1991)), adeno-associated virus vectors, retrovirus vectors (see, e.g., U.S. Pat. Nos. 4,405,712 and 4,650,764), and the like. Especially preferred viral vectors are the adenovirus and retroviral vectors.

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., *Proc. Natl. Acad. Sci. USA*, 85:9655-9659 (1988)), and the like.

In particular, the specificity of viral vectors for particular cell types can be utilized to target predetermined cell types. Thus, the selection of a viral vector will depend, in part, on the cell type to be targeted. For example, if a neurodegenerative disease is to be treated by increasing the level of a CARD-containing polypeptide in neuronal cells affected by the disease, then a viral vector that targets neuronal cells can be used. A vector derived from a herpes simplex virus is an example of a viral vector that targets neuronal cells (Battleman et al., *J. Neurosci.* 13:941-951 (1993), which is incorporated herein by reference). Similarly, if a disease or pathological condition of the hematopoietic system is to be treated, then a viral vector that is specific for a particular blood cell or its precursor cell can be used. A vector based on a human immunodeficiency virus is an example of such a viral vector (Carroll et al., *J. Cell. Biochem.* 17E:241 (1993), which is incorporated herein by reference). In addition, a viral vector or other vector can be constructed to express a CARD-encoding nucleic acid in a tissue specific manner by incorporating a tissue-specific promoter or enhancer into the vector (Dai et al., *Proc. Natl. Acad. Sci. USA* 89:10892-10895 (1992), which is incorporated herein by reference).

For gene therapy, a vector containing a CARD-encoding nucleic acid or an antisense nucleotide sequence can be administered to a subject by various methods. For example, if viral vectors are used, administration can take advantage of the target specificity of the vectors. In such cases, there in no need to administer the vector locally at the diseased site. However, local administration can be a particularly effective method of administering a CARD-encoding nucleic acid. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a CARD-encoding nucleic acid molecule into cells in a tissue-specific manner using a tissue-specific ligand or an antibody that is non-covalently complexed with the nucleic acid molecule via a bridging molecule (Curiel et al., Hum. Gene Ther. 3:147-154 (1992); Wu and Wu, J. Biol. Chem. 262:4429-4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., Science 259: 1745-1748 (1993), which is incorporated herein by reference). In addition, a CARD-encoding nucleic acid molecule can be transferred into a variety of tissues using the particle bombardment method (Williams et al., Proc. Natl. Acad. Sci. USA 88:2726-2730 (1991), which is incorporated herein by reference). Such nucleic acid molecules can be linked to the appropriate nucleotide sequences required for transcription and translation.

A particularly useful mode of administration of a CARD-encoding nucleic acid is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promoter, an enhancer or other expression element specific for the desired subset of cells can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

The present invention also provides therapeutic compositions useful for practicing the therapeutic methods described herein. Therapeutic compositions of the present invention, such as pharmaceutical compositions, contain a physiologically compatible carrier together with an invention CARD-containing polypeptide (or functional fragment thereof), an invention CARD-encoding nucleic acid, an agent that alters CARD activity or expression identified by the methods described herein, or an anti-CARD antibody, as described herein, dissolved or dispersed therein as an active ingredient. In a preferred embodiment, the therapeutic composition is not immunogenic when administered to a mammal or human patient for therapeutic purposes.

As used herein, the terms “pharmaceutically acceptable”, “physiologically compatible” and grammatical variations thereof, as they refer to compositions, carriers, diluents and reagents, are used interchangeably and represent that the materials are capable of administration to a mammal without the production of undesirable physiological effects.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an “effective amount” is a predetermined amount calculated to achieve the desired therapeutic effect, i.e., to alter the protein binding activity of a CARD-containing polypeptide or the catalytic activity of a CARD-containing polypeptide, resulting in altered biochemical process modulated by a CARD-containing polypeptide. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such agents in depot or long-lasting form as discussed herein. A therapeutically effective amount is typically an amount of an agent identified herein that, when administered in a physiologically acceptable composition, is sufficient to achieve a plasma concentration of from about 0.1 μg/ml to about 100 μg/ml, preferably from about 1.0 μg/ml to about 50 μg/ml, more preferably at least about 2 μg/ml and usually 5 to 10 μg/ml. Therapeutic invention anti-CARD antibodies can be administered in proportionately appropriate amounts in accordance with known practices in this art.

Also provided herein are methods of treating pathologies characterized by abnormal cell proliferation, abnormal cell death, or inflammation said method comprising administering an effective amount of an invention therapeutic composition. Such compositions are typically administered in a physiologically compatible composition.

Exemplary abnormal cell proliferation diseases associated with CARD-containing polypeptides contemplated herein for treatment according to the present invention include cancer pathologies, keratinocyte hyperplasia, neoplasia, keloid, benign prostatic hypertrophy, inflammatory hyperplasia, fibrosis, smooth muscle cell proliferation in arteries following balloon angioplasty (restenosis), and the like. Exemplary cancer pathologies contemplated herein for treatment include, gliomas, carcinomas, adenocarcinomas, sarcomas, melanomas, hamartomas, leukemias, lymphomas, and the like. Further diseases associated with CARD-containing polypeptides contemplated herein for treatment according to the present invention include inflammatory diseases and diseases of cell loss. Such diseases include allergies, inflammatory diseases including arthritis, lupus, Schrogen's syndrome, Crohn's disease, ulcerative colitis, as well as allograft rejection, such as graft-versus-host disease, and the like. CARD-containing polypeptides can also be useful in design of strategies for preventing diseases related to abnormal cell death in conditions such as stroke, myocardial infarction, heart failure, neurodegenerative diseases such as Parkinson's and Alzheimer's diseases, and for immunodeficiency associated diseases such as HIV infection, HIV-related disease, and the like.

Methods of treating pathologies can include methods of modulating the activity of one or more oncogenic proteins, wherein the oncogenic proteins specifically interact with a CARD-containing polypeptide of the invention. Methods of modulating the activity of such oncogenic proteins will include contacting the oncogenic protein with a substantially pure CARD-containing polypeptide or an active fragment (i.e., oncogenic protein-binding fragment) thereof. This contacting will alter the activity of the oncogenic protein, thereby providing a method of treating a pathology caused by the oncogenic protein. Further methods of modulating the activity of oncogenic proteins will include contacting the oncogenic protein with an agent, wherein the agent alters interaction between a CARD-containing polypeptide and an oncogenic protein.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like.

The present invention also provides methods for diagnosing a pathology that is characterized by an increased or decreased level of a biochemical process to determine whether the increased or decreased level of the biochemical process is due, for example, to increased or decreased expression of a CARD-containing polypeptide or to expression of a variant CARD-containing polypeptide. As disclosed herein, such biochemical processes include apoptosis, NF-kB induction, cytokine processing, caspase-mediated proteolysis, transcription, inflammation, cell adhesion, and the like. The identification of such a pathology, which can be due to altered association of a CARD-containing polypeptide with a CARD-associated polypeptide in a cell, or altered ligand binding or catalytic activity of a CARD-containing polypeptide, can allow for intervention therapy using an effective agent, or a nucleic acid molecule or an antisense nucleotide sequence as described herein. In general, a test sample can be obtained from a subject having a pathology characterized by having or suspected of having increased or decreased apoptosis and can be compared to a reference sample from a normal subject to determine whether a cell in the test sample has, for example, increased or decreased expression of a CARD-encoding gene. The level of a CARD-containing polypeptide in a cell can be determined by contacting a sample with a reagent such as an anti-CARD antibody or a CARD-associated polypeptide, either of which can specifically bind a CARD-containing polypeptide. For example, the level of a CARD-containing polypeptide in a cell can determined by well known immunoassay or immunohistochemical methods using an anti-CARD antibody (see, for example, Reed et al., *Anal. Biochem.* 205:70-76 (1992); see, also, Harlow and Lane, supra, (1988)). As used herein, the term "reagent" means a chemical or biological molecule that can specifically bind to a CARD-containing polypeptide or to a bound CARD/CARD-associated polypeptide complex. For example, either an anti-CARD antibody or a CARD-associated polypeptide can be a reagent for a CARD-containing polypeptide, whereas either an anti-CARD antibody or an anti-CARD-associated polypeptide antibody can be a reagent for a CARD/CARD-associated polypeptide complex.

As used herein, the term "test sample" means a cell or tissue specimen that is obtained from a subject and is to be examined for expression of a CARD-encoding gene in a cell in the sample. A test sample can be obtained, for example, during surgery or by needle biopsy and can be examined using the methods described herein to diagnose a pathology characterized by increased or decreased apoptosis. Increased or decreased expression of a CARD-encoding gene in a cell in a test sample can be determined, for example, by comparison to an expected normal level of CARD-containing polypeptide or CARD-encoding mRNA in a particular cell type. A normal range of CARD-containing polypeptide or CARD-encoding mRNA levels in various cell types can be determined by sampling a statistically significant number of normal subjects. In addition, a reference sample can be evaluated in parallel with a test sample in order to determine whether a pathology characterized by increased or decreased apoptosis is due to increased or decreased expression of a CARD-encoding gene. The test sample can be examined using, for example, immunohistochemical methods as described above or the sample can be further processed and examined. For example, an extract of a test sample can be prepared and examined to determine whether a CARD-containing polypeptide in the sample can associate with a CARD-associated polypeptide in the same manner as a CARD-containing polypeptide from a reference cell or whether, instead, a variant CARD-containing polypeptide is expressed in the cell.

In accordance with another embodiment of the present invention, there are provided diagnostic systems, preferably in kit form, comprising at least one invention CARD-encoding nucleic acid, CARD-containing polypeptide, and/or anti-CARD antibody described herein, in a suitable packaging material. In one embodiment, for example, the diagnostic nucleic acids are derived from any of SEQ ID NOS:11, 187, 96, 98, 100, 102, 85 and 89. Invention diagnostic systems are useful for assaying for the presence or absence of CARD-encoding nucleic acid in either genomic DNA or in transcribed CARD-encoding nucleic acid, such as mRNA or cDNA.

A suitable diagnostic system includes at least one invention CARD-encoding nucleic acid, CARD-containing polypeptide, and/or anti-CARD antibody, preferably two or more invention nucleic acids, proteins and/or antibodies, as a separately packaged chemical reagent(s) in an amount sufficient for at least one assay. Instructions for use of the packaged reagent are also typically included. Those of skill in the art can readily incorporate invention nucleic acid probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular CARD-encoding sequence including the nucleotide sequences set forth in SEQ ID NOS: 11, 187, 96, 98, 100, 102, 85 and 89 or mutations or deletions therein, thereby diagnosing the presence of, or a predisposition for a pathology such as cancer or an autoimmune disease. In addition, the packaging material contains instructions indicating how the materials within the kit are employed both to detect a particular sequence and diagnose the presence of, or a predisposition for a pathology such as cancer or an autoimmune disease.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

A diagnostic assay should include a simple method for detecting the amount of a CARD-containing polypeptide or CARD-encoding nucleic acid in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a labeled reagent with a test sample and, if desired, a control sample, specifically bound reagent can be identified by detecting the particular moiety.

A labeled antibody that can specifically bind the reagent also can be used to identify specific binding of an unlabeled reagent. For example, if the reagent is an anti-CARD antibody, a second antibody can be used to detect specific binding of the anti-CARD antibody. A second antibody generally will be specific for the particular class of the first antibody. For example, if an anti-CARD antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample.

In accordance with another embodiment of the invention, there are provided methods for determining a prognosis of disease free or overall survival in a patient suffering from cancer. For example, it is contemplated herein that abnormal levels of CARD-containing polypeptides (either higher or lower) in primary tumor tissue show a high correlation with either increased or decreased tumor recurrence or spread, and therefore indicates the likelihood of disease free or overall survival. Thus, the present invention advantageously provides a significant advancement in cancer management because early identification of patients at risk for tumor recurrence or spread will permit aggressive early treatment with significantly enhanced potential for survival. Also provided are methods for predicting the risk of tumor recurrence or spread in an individual having a cancer tumor; methods for screening a cancer patient to determine the risk of tumor metastasis; and methods for determining the proper course of treatment for a patient suffering from cancer. These methods are carried out by collecting a sample from a patient and comparing the level of CARD-encoding gene expression in the patient to the level of expression in a control or to a reference level of CARD-encoding gene expression as defined by patient population sampling, tissue culture analysis, or any other method known for determining reference levels for determination of disease prognosis. The level of CARD-encoding gene expression in the patient is then classified as higher than the reference level or lower than the reference level, wherein the prognosis of survival or tumor recurrence is different for patients with higher levels than the prognosis for patients with lower levels.

All U.S. patents and all publications mentioned herein are incorporated in their entirety by reference thereto. The invention will now be described in greater detail by reference to the following non-limiting examples.

EXAMPLES 1.0 Identification of CARD-Containing Polypeptides

The process of gene identification and assembling include the following steps:

A) Identification of new candidate CARD containing polypeptides. A database search was performed using the TBLASTN program with the CARD domain of caspase-1 and caspase-12 as the query in the following NCBI databases: high throughput genome sequence (HTGS), genomic survey sequence (GSS) and expressed sequence tag (EST) databases.

B) Verification that the new candidate CARD containing polypeptide is novel. Using PSI-BLAST, each new candidate CARD gene was queried in the annotated non-redundant (NR) database at NCBI. When the new candidate gene showed significant but not identical homology with other known CARD containing polypeptides during this search, the CARD containing polypeptide candidate was kept for further analysis.

C) 3-D-Model Building of new candidate CARD polypeptide: When the sequence homology was low (<25% identity), three-dimensional criteria was added to characterization of new CARD-containing polypeptides. The candidate CARD fragment was analyzed by a profile-profile sequence comparison method which aligns the candidate CARD domain with a database of sequences of known three-dimensional structure. From this analysis, a sequence alignment was produced and a three-dimensional model was built according to the known structure of CARD domain of IAP-1. In most cases, the best score was produced using CARD domain sequences having known three-dimensional structures. The quality of the three-dimensional model obtained from the alignments confirmed that novel CARD-domain containing polypeptides had been identified.

D) Identification of additional domains in the full length protein. Full length protein sequences were obtained using the closest full-length caspase homolog of the new CARD identified in step B as query. TBLASTN searches of the sequences containing the newly identified CARD domains were performed. Longer aligned fragments or multiple aligned fragments in the accession number corresponding to the newly identified CARD containing polypeptides indicated a longer protein.

E) These additional domains were assembled using the following gene building procedure:

Genomic DNA fragments were identified by T-BLAST-N analysis using mouse caspase-12 and human caspase-1 full length protein as query and scanning HTGS database from NCBI of incomplete DNA genomics sequences. New fragments homologous to caspase-12 and caspase-1 were further confirmed by psi-blast analysis using the TBLASTN genomic DNA homolog fragment as query and scanning NR database. The boundary of each fragment was identified according to the following criteria:

Disruption of sequence similarity between the protein alignment of the target fragment and the query.

Extension of the protein sequence alignment between query and target using ORF finder.

Protein sequence overlap between two contiguous fragments in sequence relative to the query.

Conservation of exon-intron junction between DNA sequence of the target and query.

Orientation of the ORF of the different genomic DNA fragment.

Presence of contiguous fragments, based on sequence alignment with the query, on the same contig.

Finally, the reconstituted sequences were aligned by CLUSTALW with the query and exon-intron junctions further refined by repeating the above process.

2.0 Identification of CARD2X, CARD3X and CLAN

Nucleic acids encoding CARD containing proteins CARD2X, CARD3X and CLAN were identified from different CARD queries using tblastn and systematically scanning gss, htgs, and all EST databases at NCBI. Further analysis using translated genomic fragment containing CARD domains larger than the CARD domain itself as query were performed to identify additional domains. Genomic DNA were translated in all reading frames and examined for additional domains using psi-blast and nr database.

3.0 Cloning and Sequencing of Large cDNA

For cDNA larger than 1500 bp, cloning is accomplished by amplification of multiple fragments of the cDNA. Jurkat total RNA is reverse-transcribed to complementary DNAs using MMLV reverse transcriptase (Stratagene) and random hexanucleotide primers. Overlapping cDNA fragments of a CARD-containing polypeptide are amplified from the Jurkat complementary DNAs with Pfu Turbo™ DNA polymerase (Stratagene) using an oligonucleotide primer set for every 1500 bp of cDNA, where the amplified cDNA fragment contains a unique restriction site near the end that is to be ligated with an adjacent amplified cDNA fragment.

The resultant cDNA fragments are ligated into mammalian expression vector pcDNA™ myc (Invitrogen, modified as described in Roy et al., *EMBO J.* 16:6914-6925 (1997)) and assembled to full-length cDNA by consecutively ligating adjacent fragments at the unique endonuclease sites form the full-length cDNA. Sequencing analysis of the assembled full-length cDNA is carried out, and splice isoforms of CARD-containing polypeptides can be identified.

4.0 Plasmid Constructions

Complementary DNA encoding a CARD-containing polypeptide, or a functional fragment thereof is amplified from Jurkat cDNAs with Pfu Turbo™ DNA polymerase (Stratagene) and desired primers, such as those described above. The resultant PCR fragments are digested with restriction enzymes such as EcoRI and Xho I and ligated into pGEX-4T1 (Pharmacia) and pcDNA-myc vectors.

5.0 In vitro Protein Binding Assays

CARD-containing or fragments thereof encoded in pGEX-4T1 are expressed in XL-1 blue *E. coli* cells (Stratagene), and affinity-purified using glutathione (GSH) Sepharose™ according to known methods, such as those in *Current Protocols in Molecular Biology*, Ausubel et al. eds., John Wiley and Sons (1999). For GST pull-down assays, purified CARD-GST fusion proteins and GST alone (0.1-0.5 µg immobilized on 10-15 µl GSH Sepharose™ beads) are incubated with 1 mg/ml of BSA in 100 µl Co-IP buffer (142.4 mM KCl, 5 mM $MgCl_2$, 10 mM HEPES (pH 7.4), 0.5 mM EGTA, 0.2% NP-40, 1 mM DTT, and 1 mH PMSF) for 30 min. at room temperature. The beads are then incubated with 1 µl of rat reticulocyte lysates (TnT-lysate; Promega, Inc.) containing $^{35}$S-labeled, in vitro translated CARD-containing or control protein Skp-1 in 100 µl Co-IP buffer supplemented with 0.5 mg/ml BSA for overnight at 4° C. The beads are washed four times in 500 µl Co-IP buffer, followed by boiling in 20 µl Laemmli-SDS sample buffer. The eluted proteins are analyzed by SDS-PAGE. The bands of SDS-PAGE gels are detected by fluorography.

The resultant oligomerization pattern will reveal that CARD:CARD and other protein:protein interactions occur with CARD-containing polypeptides or fragments thereof.

In vitro translated candidate CARD-associated polypeptides such as Apaf-1 (lacking its WD domain), CED4, and control Skp-1 are subjected to GST pull-down assay using GSH-Sepharose™ beads conjugated with GST and GST-CARD-containing polypeptides as described above. Lanes containing GST-CARD yield significant signals when incubated with a CARD-associated polypeptide whereas, the controls GST alone and Skp-1 yield negligible signals.

6.0 Protein Interaction Studies in Yeast

EGY48 yeast cells (*Saccharomyces cerevisiae*: MATa, trp1, ura3, his, leu2::plexApo6-leu2) are transformed with pGilda-CARD plasmids (his marker) encoding the LexA DNA binding domain fused to: CARD-containing polypeptides, fragments thereof, or CARD-associated polypeptides. EGY48 are also transformed with a LexA-LacZ reporter plasmid pSH1840 (ura3 marker), as previously described (Durfee et al., 1993; Sato et al., 1995). Sources for cells and plasmids are described previously in U.S. Pat. No. 5,632,994, and in Zervous et al., *Cell* 72:223-232 (1993); Gyuris et al., *Cell* 75:791-803 (1993); Golemis et al., In *Current Protocols in Molecular Biology* (ed. Ausubel et al.; Green Publ.; NY 1994), each of which is incorporated herein by reference. Transformants are replica-plated on Burkholder's minimal medium (BMM) plates supplemented with leucine and 2% glucose as previously described (Sato et al., *Gene* 140:291-292 (1994)). Protein-protein interactions are scored by growth of transformants on leucine deficient BMM plates containing 2% galactose and 1% raffinose.

Protein-protein interactions are also evaluated using β-galactosidase activity assays. Colonies grown on BMM/Leu/Glucose plates are filter-lifted onto nitrocellulose membranes, and incubated over-night on BMM/Leu/galactose plates. Yeast cells are lysed by soaking filters in liquid nitrogen and thawing at room temperature. β-galactosidase activity is measured by incubating the filter in 3.2 ml Z buffer (60 mM, $Na_2HPO_4$, 40 mM $Na_2HPO_4$, 10 mM KCl, 1 mM $MGSO_4$) supplemented with 50 µl X-gal solution (20 mg/ml). Levels of β-galactosidase activity are scaled according to the intensity of blue color generated for each transformant.

The results of this experiment will show colonies on leucine deficient plates for yeast containing CARD/LexA fusions together with CARD-associated polypeptide/B42. In addition, the CARD/LexA:CARD-associated polypeptide/B42 cells will have significant amounts of LacZ activity.

7.0 Self-Association of NB-ARC Domain of CARD-Containing Polypeptides

In vitro translated, $^{35}S$-labeled rat reticulocyte lysates (1 µl) containing NB-ARC or Skp-1 (used as a control) are incubated with GSH-Sepharose™ beads conjugated with purified GST-NB-ARC or GST alone for GST pull-down assay, resolved on SDS-PAGE and visualized by fluorography as described above. One tenth of input is loaded for NB-ARC or Skp-1 as controls.

8.0 Protein-Protein Interactions of CARD-Containing Polypeptides

Transient transfection of 293T, a human embryonic kidney fibroblast cell line, are conducted using SuperFect™ reagents (Qiagen) according to manufacturer's instructions. The cDNA fragments encoding full-length CED4 and the truncated form of Apaf-1 (Apaf-1ΔWD) comprising amino acids 1-420 of the human Apaf-1 protein are amplified by PCR and subcloned into pcDNA3HA at EcoRI and Xho I sites. Expression plasmids encoding catalytically inactive forms of caspases such as pro-Casp8 (pro-Casp8 (C/A)) are prepared by replacing Cys 377 with an Ala using site-directed mutagenesis and pro-Casp9 (pro-Casp9 (C/A)) has been described previously, Cardone et al., *Science* 282:1318-1321 (1998)). 293T cells are transiently transfected with an expression plasmid (2 µg) encoding HA-tagged human Apaf-1ΔWD, CED4, pro-Casp8 (C/A) or C-Terminal FLAG™-tagged pro-Casp9 (C/A) in the presence or absence of a plasmid (2 µg) encoding myc-tagged CARD-containing polypeptide. After 24 hr growth in culture, transfected cells are collected and lysed in Co-IP buffer (142.4 mM KCl, 5 mM $MgCl_2$, 10 mlvi HEPES (pH 7.4), 0.5 mM EGTA, 0.1% NP-40, and 1 mM DTT) supplemented with 12.5 mM β-glycerolphosphate, 2 mM NaF, 1 mM $Na_3VO_4$, 1 mlvi PMSF, and 1× protenase inhibitor mix (Boehringer Mannheim). Cell lysates are clarified by microcentrifugation and subjected to immunoprecipitation using either a mouse monoclonal antibody to myc (Santa Cruz Biotechnologies, Inc) or a control mouse IgG. Proteins from the immune complexes are resolved by SDS-PAGE, transferred to nitrocellulose membranes, and subjected to immunoblot analysis using anti-HA antibodies followed by anti-myc antibodies using a standard Western blotting procedure and ECL reagents from Amersham-Pharmacia Biotechnologies, Inc. (Krajewski et al., *Proc. Natl. Acad. Sci. USA* 96:5752-5757 (1999)).

9.0 Cloning and Characterization of CARD2X

CARD2X-encoding cDNA was obtained by PCR using primers CGGAATTCATGGCTACCGAGAGTACTCC (SEQ ID NO:76) and GTAAAACGACGGCCAGT (SEQ ID NO:77) to amplify a 0.9 kb cDNA molecule from a human skeletal muscle cDNA library (Clontech). The PCR products was then purified by agarose gel electrophoresis and the purified products subcloned into pBluescript™ II SK vector (Stratagene). Using the forward primers, the PCR fragments were directly sequenced using the ABI PRISM™ Big Dye Terminal Cycle sequencing kit, according to manufacturer's instructions (Perkin Elmer). Based on the sequence obtained, a third CARD2X-specific primer was generated having the sequence GCAGAAGCCACTGTGGAAGAGGAGGTT (SEQ ID NO:78). In identifying the 3'end of the CARD2X-encoding cDNA, this third CARD2X-specific primer was used in conjunction with a phage-specific primer having the sequence ATACGACTCACTATAGGGCGAATTGGCC (SEQ ID NO:79) to amplify a 0.3 kb cDNA molecule using methods described above. The 0.3 kb cDNA molecule was cloned and sequenced as described above, and the sequences of the 0.3 and 0.9 kb cDNA molecules were merged to produce a 1.0 kb cDNA sequence.

The sequence of CARD2X was confirmed. Additional 5' untranslated sequence was identified (nucleotide sequence of CARD2X including 5' untranslated sequence, SEQ ID NO:84). The CARD domain extends from amino acids 4 to 78 of SEQ ID NO:12.

The association between CARD2X and other CARD-containing proteins was determined. HEK 293T cells in 6-well plates were transfected using SuperFect™ (Qiagen) with pairwise combinations of Myc-tagged or FLAG™-tagged CARD2X, CARDIAK or NOD1 (total DNA 2 µg). After 24 hours, cells were collected in 400 µl of lysis buffer (20 mM Tris, pH 7.4, 150 mM NaCl, 1% NP-40, and 1 mM EDTA supplemented with 1× protease inhibitors mix (Roche/Boehringer Mannheim)). Cell lysates were clarified by centrifugation and subjected to immunoprecipitation using Agarose-beads conjugated with anti-FLAG™ M2 antibody (Sigma). Immune-complexes were washed three times with wash buffer (20 mM Tris, pH 7.4, 100 mM NaCl, 0.05% NP-40, and 1 mM EDTA), and resolved on SDS-PAGE gels. Proteins in the gels were transferred to nitrocellulose membranes, immunoblotted with anti-Myc antibodies, and detected with ECL (Amersham-Pharmacia Biotech). Epitope-specific antibodies for myc, FLAG™, or HA tag were obtained from Santa Cruz Biotech, Roche/Boehringer Mannheim, and Sigma. The results of these co-immunoprecipitation assays demonstrated that CARD2X specifically associates with both NOD1 and with CARDIAK.

The effect of CARDIAK on CARD2X phosphorylation was next determined. HEK 293T cells transiently expressing FLAG™-CARDIAK were lysed and immunoprecipitated with Agarose-beads conjugated with anti-FLAG™ M2 antibody. In vitro phosphorylation was performed in the immune complex with or without purified Myc-CARD-2X as a substrate. The kinase reaction was initiated by adding 1 µM of [γ-$^{32}$P]ATP in 10 µl of kinase buffer (50 mM Tris, pH7.4, 100 mM NaCl, 6 mM MgCl$_2$, 1 mM MnCl, and 1 mM EDTA). After 20 mm at 37° C., the reaction was stopped by adding 10 µl of 2×SDS sample buffer, and subjected to SDS-PAGE and autoradiography. The results of these assays indicated that CARD2X is not phosphorylated directly by CARDIAK.

Phosphatase assays were also performed to examine phosphorylation of CARD2X. HEK 293 cells were transfected with plasmids encoding Myc-CARD-2× with or without FLAG™-CARDIAK or FLAG™-CARDIAK (K47M), which is a kinase deficient mutant of CARDIAK. The cleared lysates were diluted 1:20 with 20 µl of reaction buffer (25 mM Tris, pH8.0, 50 mM NaCl, 5 mM MgCl$_9$, and optionally treated with 2 units of calf intestine alkaline phosphatase (Gibco BRL) for 30 mm at 37° C. The reaction was terminated by adding 7 µl 4×SDS sample buffer, and subjected to SDS-PAGE and immunoblot. The phosphorylated form of CARD2X migrates more slowly that CARD2X, and is not observed after phosphatase treatment. The results of these assays indicated that CARD2X is phosphorylated in vivo in the presence of either CARDIAK or kinase-deficient CARDIAK, but not in their absence. Taken together with the in vitro phosphorylation results above, these results indicate that CARDIAK is indirectly involved in CARD2X phosphorylation.

The 30-35 residues at the carboxy terminus of CARD2X have homology to human Alu family sequences and RhoGAP. Thus, this region can have activity similar to that observed in human Alu family sequences and RhoGAP.

10.0 Cloning and characterization of CLAN

CLAN encoding cDNA was obtained by polymerase chain reaction (PCR) using primers CXF1:TACTTACTTTGTC-CCTTCA (SEQ ID NO:74) and CXR2:TATTTGTC-CCCATCTCGTC (SEQ ID NO:75) to amplify cDNA from a human genomic library. Thirty cycles of PCR were carried out using Pfu Turbo™ DNA polymerase (Stratagene) at annealing temperature 47° C. and extension temperature 72° C. The PCR product was then purified by agarose gel electrophoresis and the purified product subcloned into pGEM™-T vector (Promega).

The HTSG database of human genomic DNA sequence data was searched for regions capable of encoding CARDs using the CARD amino-acid sequence of cIAP-1 as a query with the TBLASTn method. This search revealed strong homology with a human genomic clone (Accession number: AQ889169) that mapped to human chromosome 2p21-22. This locus was not recognized in the human genomic database and was not previously annotated. In initial studies, two genes encoding CARD domain containing polypeptides, designated CARD4X and CARD5X, were identified. Upon further characterization, it was determined that CARD4X (also known as NAC-X or NAC-4) and CARD5X were actually encoded by the same gene, which is therefore referenced as CARD4/5X. CARD4/5X was subsequently designated CLAN, which stands for "CARD, LRR and NACHT-containing protein," because at least one of the proteins encoded by it contains CARD, Leucine Rich Repeat (LRR) and NACHT (NB-ARC) domains, as described below.

The CLAN gene locus lies in close proximity to the gene encoding Spastin (on chromosome 2p21-22), a AAA protein which is frequently mutated in autosomal dominant hereditary spastic paraplegia (AD-HSP). The CLAN locus is found on the strand opposite the SPG4 (SPAST) locus but with no overlapping regions. This result suggests that mutations in the CLAN gene potentially occur in patients with this neurodegenerative disorder.

Using GENESCAN for exon prediction, additional regions potentially encoding a NACHT (NB-ARC) domain and regions corresponding to Leucine-Rich Repeat (LRR) domains were also recognized 3' to the potential CARD-encoding sequences, suggesting the presence of a CED4-like gene.

10.1 Cloning of CLAN cDNAs

CLAN-specific primers corresponding to sequences within the putative CARD and NACHT (NB-ARC) regions (as determined from genomic DNA sequence data) were used in conjunction with 2 universal primers to isolate CLAN cDNAs from first-strand liver and lung cDNA by nested PCR according to the manufacturer's protocol (SMART RACE, Clontech). Primers used for amplification are 5' RACE primers (5'-CATGTGAATGATCCCTCTAGCAG-3' (SEQ ID NO:153); nested 5'-GGGCTCGGCTATCGTGCTCTA-3' (SEQ ID NO:154)) and 3' RACE primers (5'-ACGATAGC-CGAGCCCTTATTC-3' (SEQ ID NO:155); nested 5'-GTATGGAATGTTCTGAATCGC-3' (SEQ ID NO; 156)). Amplification products were purified from agarose gels, ligated into the TA cloning vector (Promega), and sequenced. Four open reading frames were deduced and multiple clones of each isoform were sequenced to ensure fidelity of PCR products.

The longest transcript, termed CLAN-A, was 3.370 kilobasepairs (kbp) in length (SEQ ID NO:96) with an open reading frame (ORF) coding for a 1024 amino-acid protein (SEQ ID NO:97) containing a CARD, NACHT (NB-ARC), and LRR-domains, as well as a predicted SAM domain. A second transcript, termed CLAN-B, was 1.374 kbp in length (SEQ ID NO:98), with an ORF coding for a 359 amino-acid protein (SEQ ID NO:99) containing an identical CARD directly spliced to the LRRs. CLAN-C, the third transcript isolated, was 0.768 kbp in length (SEQ ID NO:102) and encoded a 156 amino acid protein (SEQ ID NO:103) containing the CARD and an additional region lacking homology to recognizable domains. Finally, the shortest transcript found, CLAN-D, was 0.578 kbp in length (SEQ ID NO:100) and contained an ORF encoding a 92 amino-acid protein (SEQ ID NO:101) encompassing only the CARD followed by 9 amino acids.

Comparisons of these cDNA sequence data with the genomic DNA sequence data found in the HTSG database suggested that the CLAN gene consists of 12 exons, spanning 41.3 kbp on chromosome 2p21-22 (FIG. 1A). Six differences were found between the sequence of the CLAN cDNA and the sequence within the public database. Additionally, nucleotide regions 1-12 and 3372-3396 do not have equivalent fragments in the public database.

Figure 1B:
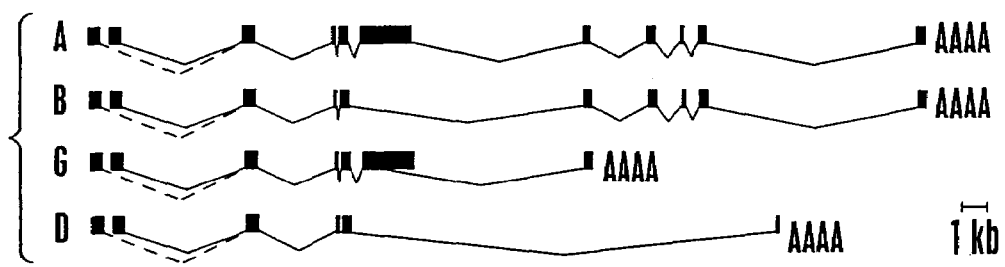
FIG. 1B shows mRNA splicing generating CLAN A, B, C and D.
Figure 1C:
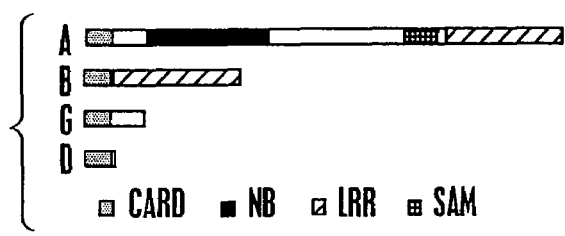
FIG. 1C shows the deduced domain structure for the splice forms of CARD4/5X (CLAN A, B, C and D).

Southern blot analysis was also performed. For Southern blot analysis, 10 µg of restriction endonuclease (EcoRI or PstI) digested genomic DNA was loaded per lane and hybridized with the CARD domain of CLAN as a probe. The probe was derived from the CLAN A-isoform (see. FIGS. 1 and 2), nucleotides 276 to 507 plus an additional 20 upstream nucleotides, which are not present in the cDNA but are present in the genomic DNA. CLAN was found to be a single copy gene.

Two different transcriptional start sites are utilized (corresponding to the beginning of either exon 1 or 2); however both are spliced to exon 3 at the beginning of the CARD. Exons 6 and 7 contain additional internal splice donor sites which are utilized to generate CLAN-G. FIG. 1B shows the pattern of mRNA splicing events predicted to give rise to the CLAN-A, CLAN-B, CLAN-C, and CLAN-D transcripts and encoded proteins. All the exon/intron splice junctions follow the conserved GT/AG consensus rule.

As predicted by SMART (EMBL, Heidelberg, Germany), CLAN contains a CARD (amino acids 1-87 of SEQ ID NO:97). A ψ-BLAST search of the non-redundant database using the CLAN CARD as query identified several homologous CARDs including those from cIAP1 and 2 (58%), caspase-1 and ICEBERG (50%), Nod1, Nod2, and Card8 (~38%) and caspase-13, Ced3, caspase-9, Bcl10 (CIPER) and CARKIAK/RIP2 (~30%).

Following the CARD, a domain containing consensus sequences for Walker A and B boxes is present (Walker et al., EMBO J. 8:945-951 (1982)) as well as additional characteristics of the family of NTPases termed the NACHT family (Koonin et al., *Trends. Biochem. Sci.* 25:2230224 (2000)). By ψ-BLAST search the NACHT domain of CLAN ("NB" in FIG. 1, amino acids 161-457 of SEQ ID NO:97) shows highest similarity to the NACHT domain of NAIP (60%), followed by Nod1 (49%) and Nod2 (47%).

Leucine Rich Repeat (LRR) domains are also found near the C-terminus of the A and B isoforms of the protein. The C-terminal end consists of four repeated LRRs, each containing a predicted β sheet and a helical structure, which is in agreement with the prototypical horseshoe-shaped structure of LRRs (Kobe et al., *Curr. Opin. Struct. Biol.* 5:409-416 (1999). LRR 1 (amino acids 760-791 of SEQ ID NO:97) represents a non-Kobe and Deisenhofer (non-K/D) LRR, whereas LRRs 2, 3, and 4 (amino acids 817-848; 845-876; and 934-965 of SEQ ID NO:97, respectively) are in accordance with Kobe and Deisenhofer (K/D) LRR. LRR 2 also shares sequence homology to a prototypical Ribonuclease Inhibitor type A (RI type A). By 1-BLAST searches the LRRs show 49% sequence identity to the placental ribonuclease/angiogenin inhibitor (RAI).

Sequences located between the NACHT (NB-ARC) and LRR domains show some similarity to the sterile alpha motif (SAM) (amino acids 642-696 of SEQ ID NO:97), a domain built of five alpha helices originally found in proteins involved in numerous developmental processes. The SAM domain has been shown to function as a protein-protein interaction domain, with ability to homo-as well as hetero-oligomerize with other SAMs (Stapleton et al., *Nat. Struct. Biol.* 6:44-49 (1999)).

10.2 In vivo expression of CLAN

In order to determine which of the various splice variants of CLAN are expressed in adult human tissues, Northern blot analysis was performed. Hybridization probes corresponding to the common CARD domain of all 4 CLAN isoforms or the NACHT and LRR regions were radiolabeled by random priming with hexanucleotides (Roche) and α-$^{32}$P-dCTP, or Digoxigenin-labeled with a commercially available kit (Roche), incubated with blots containing human poly(A)$^+$ RNA derived from various human tissues (Origene), washed at high stringency, and exposed to X-ray film. Positive signals were detected by autoradiography or by immunoblotting with HRP-conjugated anti-DIG antibody and an enhanced chemiluminescence method (ECL) (Amersham).

Northern blot analysis with CARD of CLAN revealed expression of an approximately 1.5 kbp transcript corresponding to CLAN-B in nearly all tissues examined, with highest expression in lung and spleen. Northern blot analysis using the NACHT and LRR of CLAN-A as a probe revealed expression of an approximately 3.5 kbp mRNA corresponding to CLAN-A primarily in the lung.

To further explore the tissue-specific patterns of expression of CLAN splicing variants, RT-PCR assays were devised specific for the A, B, C, and D isoforms. A panel of cDNA specimens derived from various human tissues was utilized (Clontech), as well as blood cells, prepared as followed. Peripheral blood leukocytes were obtained from heparinized venous blood by Ficoll-Paque (Amersham) density-gradient centrifugation. Red blood cells were removed from granulocytes by short incubation in hypotonic lysis buffer. Monocytes were separated from lymphocytes by adherence to plastic dishes. Total RNA was isolated from cells using TRIZOL™ reagent (BRL) and 2 µg was used to generate cDNA in a reverse transcription reaction with Superscript™ II (BRL).

PCR was carried out on the cDNA samples in an Eppendorf thermal cycler using Taq polymerase (BRL) and the following isoform-specific primer pairs: CLAN-A 5'-GGTGGAG-CAGGATGCTGCTAGAGG-3' (SEQ ID NO:159), 5'-CA-CAGTGGTCCAGGCTCCGAATGAAGTCA-3' (SEQ ID NO:160); CLAN-B 5'-CATCATTTGCTGCGAGAAGGTG-GAG-3' (SEQ ID NO:161), 5'-TTAACTTGGATAACACT-TGGCTAAG-3' (SEQ ID NO:162); CLAN-C5'-GTAAA-CATCATTTGCTGCGAGAA-3' (SEQ ID NO:163), 5'-CCCGGGCAGGTAGAAGATGCTAT-3' (SEQ ID NO:164); CLAN-D 5'AATTTCATAAAGGACAATAGC-CGAG-3' (SEQ ID NO:165), 5'-TGTCTACTG-TACTTTCTAAGCTGTT-3' (SEQ ID NO:166).

RT-PCR analysis showed that CLAN-B was present throughout human tissues (brain, heart, kidney, liver, lung, pancreas, placenta, skeletal muscle, colon, ovary, leukocytes, prostate, small intestine, spleen, testis, thymus), consistent with the Northern blot analysis. In contrast, CLAN-A was restricted to lung, colon, brain, prostate, spleen and leukocytes, but not other tissues. Further analysis of leukocyte sub-populations revealed expression of the CLAN-A isoform predominantly in the monocyte cell fraction, with lower expression found in granulocytes and no expression in lymphocytes. Expression of CLAN-C was absent in all normal tissues tested, however, expression was evident in the cell line HEK293T, suggesting this transcript can be produced under some circumstances. CLAN-D transcripts were detected only in brain by RT-PCR.

RT-PCR was also performed on cell lines. RT-PCR was performed using the same CLAN primers as used for RT-PCR in normal tissues, as described above. RT-PCR was performed in various tumor derived cell lines: M2, OVCAR3, HEY, HaCaT, 293T, SKOV-3, Jurkat, BG-1, 697, HL-60, PC3, DU145, MDA-MB-231, MCF-7, MDA-MB-4, HS578T, BT-549, and T-47D. Beta-actin primers were used as a control. In contrast to normal tissue, the transcript for CLAN was mostly absent in the cell lines tested. Weak expression was found in the cell lines 697, MDA-MB-231, MVF-7, MDA-MB-4, HS578T, and T-47D.

10.3 CLAN protein interactions

Interactions between the CARD of CLAN and known CARD domains were tested in vitro and in vivo.

To test CLAN interactions with other molecules, an in vitro binding assay was performed. CLAN was in vitro translated in the absence of label (i.e., cold). Other cellular proteins were labeled in vitro with $^{35}$S-Met: CLAN, caspase1, caspase2, caspase8, caspase9, caspase10, Apaf1, Apaf1-CARD, NACa, NAC-CARD, Bcl10, ASC, cIAP1, cIAP2, XIAP, Nod1, Ced4, RAIDD, and CARDIAK. The in vitro translated proteins were mixed separately with unlabeled CLAN and co-immunoprecipitated using an antibody against an epitope tag fused to CARD5X, either myc or hemaglutinin (HA). CLAN associated proteins were eluted by boiling in Laemmli denaturing buffer and separated by 12% SDS-PAGE. The radioactive bands were visualized by fluorography.

Weak binding to CLAN was observed with caspase2 and cIAP1, with stronger binding to Nod1 and Cardiak. The strongest binding was observed with Ced4. Caspase8 binding is possibly due to its stickiness. There was no association detected between CLAN and itself.

To prepare appropriate expression vectors for in vivo interaction studies, a cDNA encoding the CLAN CARD domain was amplified using PFU polymerase and specific primers (5'-CCCGGATCCATGAATTTCATAAAGGACAATAGC-3' (SEQ ID NO:153); 5'-CCCTTCGAACAAGTCCT-GAAATAGAGGATA-3' (SEQ ID NO:154)) containing BamHI and HindIII sites. The resulting PCR product was ligated into pcDNA™ 3.1(−)/Myc-His6A (Invitrogen) which places the myc-His$_6$ tag at the C-terminus of expressed proteins. pcDNA™ 3/HA-CLAN (CARD) was created using a similar strategy. Authenticity of all vectors was confirmed by DNA sequencing.

The CARD of CLAN was expressed as an epitope-tagged protein in HEK293T cells in co-transfections with a variety of other epitope-tagged CARD-containing proteins, and lysates derived from these cells were used for co-immunoprecipitation assays. Briefly, HEK293T cells were seeded onto six-well plates (35 mm wells) and transfected with 0.2-2 mg plasmid DNA using Superfect™ (Qiagen) 24 hr later. After culturing for a day, cells were collected and lysed in isotonic lysis buffer (142.4 mM KCl, 5 mM MgCl$_2$, 10 mM HEPES (pH 7.4), 0.5 mM EGTA, 0.2% NP-40, 12.5 mM J3-glycero-phosphate, 2 mM NaF, 1 mM Na$_3$VO$_4$, 1 mM PMSF, and 1× protease inhibitor mix (Roche)). Lysates were clarified by centrifugation and subjected to immunoprecipitation using agarose-conjugated anti-c-myc antibodies (Santa Cruz), or non-specific control antibodies and Protein G-agarose for 2-24 hr at 4° C. Immune-complexes were washed four times with lysis buffer, boiled in Laemmli buffer, and separated by 12-15% PAGE. Immune-complexes were then transferred to PVDF membranes and immunoblotted with anti-c-myc (Santa Cruz), anti-HA (Roche), or anti-FLAG™ (Sigma) antibodies. Membranes were washed, incubated with HRP-conjugated secondary antibodies, and reactive proteins were detected using ECL.

Co-immunoprecipitation analysis indicated that the CARD of CLAN bound readily to full-length pro-caspase-1 but did not significantly bind another CARD-containing caspase, caspase-9. Among the other CED-4 family members which contain a CARD in conjunction with a nucleotide-binding domain, CLAN interacted with the CARDs of Nod2 and NAC, but not with Apaf-1 or Nod-1. Finally, the CLAN CARD was found to associate with Bcl-10, but not with another adapter protein, RAIDD.

11.0 Cloning and Characterization of CARD3X

Based on an analysis of the overlapping genomic contigs GI 8575872 and GI 5001450, a cDNA sequence for CARD3X was predicted (SEQ ID NO:82), that encoded amino acid sequences designated SEQ ID NOS:83 and 107.

For identification of novel domains in CARD3X, the sequence of the CARD domain of polypeptide CARD3X was used as a query for a tblastn search in the HTGS database, and two overlapping genomic contigs were found (GI numbers 5001450 and 8575872). This contig was analyzed using the GenScan server (http://ccr-081.mit.edu/GENSCAN.html) for the presence of exons. (Burge and Karlin, *J. Mol. Biol.* 268:78-94 (1997)). The predicted protein sequences coded by the exons were analyzed by comparison with the NCBI nr protein sequence database using PSI-BLAST. The predicted protein sequences coded by the exons were analyzed also by comparison with a database of proteins with known three-dimensional structures and apoptosis related domains using the profile-profile comparison server at http://bioinformatics-.burnham-inst.org/FFAS_apoptosis (Rychlewski, et al., *Protein Science* 9:232-241 (2000)).

CARD3X contains two CARD domains, a CARD-A and CARD-B domain (see FIG. 3). An NB-ARC domain was also observed (see FIG. 3). The NB-ARC is similar to both the CLAN and APAF-1 NB-ARC domains and to NB-ARC domains from several plant disease resistance proteins (Aravind et al., *Trends Biochem. Sci.* 24:47-53 (1999); Young, *Curr. Opin. Plant Biol.* 4:285-289 (2000)).

An angio-R domain was also identified at amino acids 457-839 of SEQ ID NO:107. An "angio-R" is a new domain that can be defined as a region of a polypeptide chain that bears substantial similarity (e.g. 25, 30, 40% sequence identity) to the 514-reside long protein "angiotensin II/vaso-pressin receptor" (described in Ruiz-Opazo et al., *Nature Med.* 1:1074-1081 (1995)). The "angio-R" domain has not been previously described in any protein.

To confirm the predicted sequences, cDNAs were cloned and sequenced. The CARD3X cDNA was cloned using a Rapid-Screen™ Arrayed Placenta cDNA Library Panel from Origene Technologies, Inc. The library cDNAs had been pre-selected for long clones, unidirectionally cloned into the vector pCMV6-XL4, and arrayed in a 96-well format. An initial Master Plate containing 500,000 cDNA clones was screened by PCR, using the forward primer 5'-GAAATGTGCTCG-CAGGAGG-3' (SEQ ID NO:185) and the reverse primer 5'-GATGAGCTTCTGACAGGCCC-3' (SEQ ID NO:186). A set of 5000 clones that were initially positive by PCR were screened again with the same set of primers. Positive clones were plated on LB/Amp plates, and a further round of single colony PCRs was performed in order to obtain the desired clone.

Three independent clones were sequenced, each of which corresponded to the nucleotide sequence SEQ ID NO:187. The cDNA sequence differed at both the N— and C— terminal ends from the CARD3X sequence predicted from analysis of genomic exons. SEQ ID NO:187 encodes a polypeptide of 795 amino acids (SEQ ID NO:188), followed by a stop codon. A second open reading frame begins after the stop codon, and in the same reading frame, and encodes a polypeptide of 180 amino acids (SEQ ID NO:189). SEQ ID NO:189 contains several leucine rich repeats.

Subsequent to the identification of the two polypeptides encoded by SEQ ID NO:187, a publication reported the cloning of a gene designated Nod2 cloned (Ogura et al., *J. Biol. Chem.* 276:4812-4818 (2001)). The published Nod2 sequence has additional N-terminal amino acids relative to SEQ ID NO:188 and, instead of the stop codon between the residues that encode SEQ ID NO:188 and SEQ ID NO:189, additional coding sequence is present, which encodes several additional leucine rich repeats. The published Nod2 sequence is 1040 amino acids.

It is proposed that SEQ ID NO:188 is a splice variant form of CARD3X/Nod2 that does not contain an LRR domain. The LRR of Nod2 has been shown to interfere with the ability of the protein to activate NFκB (Ogura et al., supra (2001)).

Therefore, SEQ ID NO:188 is likely expressed under physiological conditions in which activation of NFκB is required.

Human CARD3X cDNA sequences were used as a query for BLAST searches of several mouse databases. A genomic sequence, SEQ ID NO:190, was identified. Nucleotides 191-614 of SEQ ID NO:190 are homologous to the ANGIO-R coding region of human CARD3X. Nucleotides 193-612 of SEQ ID NO:191 were predicted to encode SEQ ID NO:191, which is highly homologous to amino acids 214-341 of the ANGIO-R domain of human CARD3X (SEQ ID NO:176).

PCR was then performed on mouse genomic DNA obtained from C57B6 and NIH3T3 cell lines, using the following primers: Forward primer: 5'-CTGCAGAAGGCT-GAGCCACACAACCT-3' (SEQ ID NO:194), Reverse primer: 5'-ACAGAGTTGTAATCCAGCTGTAGGGC-CACA-3' (SEQ ID NO:195). The PCR product so obtained was sequenced (SEQ ID NO:192), and shown to have several nucleotide differences as compared to the corresponding region of SEQ ID NO:190. The predicted amino acid sequence encoded by SEQ ID NO:192 (designated SEQ ID NO:193) had a single amino acid difference in comparison with SEQ ID NO:191.

Both the CARD-A and CARD-B domains are independently cloned into pcDNA3 with epitope tags such as myc or HA, as described above, and binding of the CARD domains is tested with co-immunoprecipitation to test binding of CARD3X CARD domains with other known CARD domains, as described above.

The NB-ARC domain is cloned into a yeast two-hybrid vector and into pcDNA™ 3 with two alternative epitope tags (e.g., myc and FLAG™) to determine whether the NB-ARC domain self-associates in an ATP-dependent manner/P-loop mutation. The P-loop, which binds the gamma phosphate of ATP in the NB-ARC domain, is mutated to remove a conserved Lys in the consensus P-loop sequence G-S/T-K, where Lys is generally mutated to Met. The NB-ARC domain is also tested for binding to the NB-domains of other CED-4 like proteins (e.g., apaf1, nod1, nac).

12.0 Characterization of COP-1

Using the amino-acid sequence of the caspase-1 pro-domain as a query for BLASTn searches of the public databases, a human EST clone (GenBank accession number AA070591) was identified containing an ORF encoding a 97 amino-acid protein (SEQ ID NO:86) predicted to share 92% sequence identity with the CARD of pro-caspase-1 (SEQ ID NO:87). The predicted protein contains a CARD (residues 1-91), which is followed by 6 amino-acids and then a stop-codon. The CARD region of COP-1 showed 97% identity to the CARD of pro-caspase-1.

To confirm the predicted sequences, cDNAs were amplified from various adult human tissues and sequenced. The sequenced COP-1 cDNA (SEQ ID NO:85) had the same nucleotide sequence as the original EST.

The start codon initiating the ORF in the COP-1 cDNA clones resides in a favorable context for translation, and is preceded by an in-frame stop codon. The 3'-untranslated region contains TAAA and TATA motifs, typical of short-lived mRNAs which are subject to post-transcriptional regulation, and a candidate polyadenylation signal sequence (AATAAA). Thus, this protein contains essentially only a CARD, prompting the moniker CARD Only Protein (COP-1).

To determine the genomic organization of the COP-1 gene, the COP-1 cDNA nucleotide sequence was employed for searches of the High Throughput Genomic Sequence (HTGS) database, resulting in identification of three genomic clones containing the COP-1 gene (GenBank accessions numbers AC027011, AP001153 and AP002787). Comparison of the COP-1 cDNA and genomic DNA sequences suggests a three exon structure, in which only the first two amino-acids are encoded in exon 1 and only the last 5 residues are encoded in exon 3, such that most of the coding regions (including the entire CARD) are derived from exon 2. The introns separating exons 1, 2, and 3 are 631 and 844 bp in length, respectively, containing consensus dinucleotide splice donor (GT) and splice acceptor (AG) motifs.

The COP-1 genomic clones identified in the HTSG database have been mapped to human chromosome 11q22, which is the same chromosomal region where the pro-caspase-1 gene resides, as well as pro-caspase-4, pro-caspase-5, and ICEBERG. To address the genomic localization of COP, pro-caspase-4, pro-caspase-5, and ICEBERG genes in chromosome 11, the public database of Human Genome Project Working Draft (www.genome.cse.ucsc.edu) was searched, and the order of these genes from centromere to telomere was determined to be pro-caspase-4, pro-caspase-5, pro-caspase-1, COP, and ICEBERG. This result suggests that COP-1 is a separate gene, presumably arising from duplication of other homologous genes in this locus.

14.1 COP-1 expression

To study the expression of COP-1, Northern blot analysis was performed using RNA derived from several adult human tissues and a $^{32}$P-labeled COP-1 cDNA probe. Blots containing polyA-selected mRNA from various adult tissues (Clontech, Palo Alto, Calif.) were hybridized using a $^{32}$P-labeled COP-1 cDNA probe. The probe represented a 570 bp length cDNA containing portions of the 5'-untranslated region, the complete ORF, and portions of the 3'-untranslated region of COP. The COP-1 probe (from the EST clone corresponding to AA070591 obtained from the I.M.A.G.E. Consortium (Washington University School of Medicine, St. Louis, Mo.)) was excised from the plasmid by restriction digestion with EcoRI and XhoI, gel-purified, and radiolabeled by the random priming method using [α-32P] dCTP and a kit from Ambion (Austin, Tex.). After hybridization, heat-denatured probe was annealed for 1 hr at 68° C. with QuikHyb™ Hybridization Solution (Stratagene, La Jolla, Calif.) and then blots were washed with solutions containing 2×SSC, 0.1% (w/v) SDS (twice each for 15 min at 25° C.) followed by 0.1×SSC, 0.1% (w/v) SDS (twice for 10 mm at 40° C.). Bands were visualized by autoradiography.

Hybridizing bands of approximately 0.6 kbp, 1.5 kbp and 2.6 kbp were identified, with the 0.6 kbp band representing the most abundant of these transcripts and presumably corresponding to the fully-spliced COP-1 mRNA. The less abundant larger 1.5 kbp and 2.6 kbp transcripts could represent unspliced precursors. Alternatively, the 2.6 kbp mRNA could represent pro-caspase-1 mRNA, resulting from probe cross-hybridization. The 0.6 kbp COP-1 mRNA was most abundant in spleen, followed by liver, placenta, and peripheral blood leukocytes (PBL). However, most tissues (including heart, muscle, colon, kidney, intestine and lung) were shown to contain at least some detectable 0.6 kbp COP-1 mRNA.

To corroborate the Northern blot analysis, COP-1 mRNA expression in adult human tissues was also examined using RT-PCR and COP-specific primers. cDNA samples derived from multiple human adult tissues (Clontech, Palo Alto, Calif.) were amplified using a set of COP-specific primers (a forward primer 5'-GAAGACAGTTACCTGGCAGA-3' (SEQ ID NO:147) and a reverse primer 5'-TTGTATTCT- GAACATGGCACC-3' (SEQ ID NO:148)). The resulting PCR products were size-fractionated by electrophoresis in 1.5% agarose gels, then stained with ethidium bromide for UV-photography. In some cases, bands were excised from gels, purified, and sequenced, thus verifying amplification of the correct product by the RT-PCR assay.

RT-PCR analysis showed that COP-1 mRNA was expressed in all tissues analyzed (brain, heart, muscle, colon, spleen, kidney, liver, intestine, placenta, lung and PBL), except thymus. Parallel RT-PCR analysis of β-actin mRNA served as a control. In general, the relative levels of COP-1 mRNA detected by RT-PCR were in agreement with the Northern blot data.

14.2 COP-1 interactions

The prodomain of pro-caspase-1 is required for dimerization and activation of this zymogen. Since the prodomain of COP-1 shares a high-degree of amino-acid sequence identity with the prodomain of caspase-1, the possibility that COP-1 interacts with pro-caspase-1 in co-immunoprecipitation assays was tested. Interactions with several other CARD-containing proteins were also tested, including COP-1 itself, RIP2, Bcl-10, cIAP1, cIAP2 and pro-caspase-9.

For these experiments, the entire open reading frame (ORF) of COP-1 was amplified by PCR using the primers (5'-CCAGAATTCATGGCCGACAAGGTCCTGAAG-3' (SEQ ID NO: 145) (forward) and 5'-CCACTC-GAGCTAATTTCCAGGTATCGGACC-3' (SEQ ID NO: 146) (reverse). The COP-1 PCR product was digested with EcoRI/XhoI and ligated into mammalian expression vectors pcDNA™ 3-Myc, pcDNA™ 3-HA and pcDNA™ 3-FLAG™ at the EcoRI/XhoI cloning sites. Plasmids encoding wild-type pro-caspase-1, RIP2, and pro-IL-1β were as described in Thome et al., *Curr. Biol.* 8:885-888 (1998); Nett-Fiordalisi et al, *J. Leukoc. Biol.* 58:717-724 (1995); and Wang et al., *J. Biol. Chem.* 271:20580-20587 (1996).

A pro-caspase-1 Cys 285 Ala mutant was made from wild-type caspase-1 plasmid by site-directed mutagenesis, using a commercially available kit (Stratagene, La Jolla, Calif.) and the primers 5'-GATCATCATCCAGGCCGCCCGTGGTGA-CAGCCCTGG-3' (SEQ ID NO:149) and 5'-CCAGGGCT-GTCACCACGGGCGGCCTGGATGATGATC-3' (SEQ ID NO:150). A truncation mutant of pro-caspase-1 in which a stop codon was introduced downstream of the CARD was created by PCR using primers 5'-CGGAATTCATGGCCGA-CAAGGTCCTG-3' (SEQ ID NO:151) and CGCTCGAGT-TAGTCTTGCATATTAAGGTAATTTCCAGA-3' (SEQ ID NO:152).

Human embryonic kidney 293T cells were cultured at 37° C. in 5% $CO_2$ in Dulbecco's Modified Eagle's Medium (DMEM) with 10% heat-inactivated fetal bovine serum (FBS). Cells in log phase were transfected in 60 mm diameter dishes with expression plasmids (5 μg total DNA) using Superfect™ Transfection Reagent (Qiagen, Valencia, Calif.) according to the manufacturer's recommendations. Cells were harvested 2 days later and lysed in ice-cold NP-40 lysis buffer (10 mM HEPES [pH 7.4], 142.5 mM KCl, 0.2% NP-40, 5 mM EGTA), supplemented with 1 mM DTT, 12.5 mM β-glycerophosphate, 1 μM $Na_3$ $VO_4$, 1 mM PMSF, and 1× protease inhibitor mix (Roche, Indianapolis, Ind.). Cell lysates (0.5 ml) were clarified by centrifugation at 16,000×g for 5 minutes, and subjected to immunoprecipitation using specific antibodies, including anti-Myc antibodies (Santa Cruz Biotechnology, Santa Cruz, Calif.), and anti-FLAG™ antibodies (Sigma, St. Louis, Mo.), in combination with 15 μl Protein A- or B-Sepharose™ (Zymed, South San Francisco, Calif.).

Immune-complexes were fractionated by sodium dodecyl sulfate-polyacrylamide gel electrophoresis (SDS-PAGE), and transferred to nitrocellulose membranes. The resulting blots were incubated with various antibodies, including anti-HA antibodies (1:1000 v/v; Roche, Indianapolis, Ind.), anti-Myc antibodies (1:100 v/v; Santa Cruz Biotechnology, Santa Cruz, Calif.) and anti-Flag antibodies (1: 1000 v/v; Sigma, St. Louis, Mo.), followed by horseradish peroxidase-conjugated secondary antibodies, and detection by an enhanced chemi-luminescence (ECL) method (Amersham-Pharmacia, Piscataway, N. J.). Alternatively, lysates were analyzed directly by immunoblotting after normalization for total protein content.

The co-immunoprecipitation results showed that HA-COP-1 co-immunoprecipitated with Myc-COP, indicating that this protein can self-associate. In addition, HA-COP-1 co-immunoprecipitated with Myc-tagged pro-caspase-1 (C285A mutant) as well as with a fragment of pro-caspase-1 containing only its CARD-carrying prodomain. Thus, COP-1 binds pro-caspase-1 through its CARD domain. For these co-immunoprecipitation experiments, the active site cysteine of pro-caspase-1 was mutated to avoid induction of apoptosis, which can occur when over-expressing this protease. Additionally, Myc-COP-1 co-immunoprecipitated with Flag-RIP2. In contrast, COP-1 did not co-immunoprecipitate with the CARD-containing proteins Bcl-10, cIAP1, cIAP2, or pro-caspase-9, thus demonstrating the specificity of these results.

RIP2 has been shown to bind and activate caspase-1 through the interaction of their CARDS, resulting in oligomerization of pro-caspase-1 and its activation via the "induced proximity" mechanism. The data demonstrating that COP-1 binds to both pro-caspase-1 and RIP2 therefore suggested that COP-1 might function as a modulator of RIP2-induced pro-caspase-1 oligomerization.

To test this hypothesis, experiments were performed in which 293T cells were transiently transfected with expression plasmids encoding Myc-tagged pro-caspase-1 (C285A mutant) and HA-tagged pro-caspase-1 (C285A mutant), with or without FLAG™-tagged RIP2 and COP, after which Myc-pro-caspase-1 and HA-pro-caspase-1 association was monitored by co-immunoprecipitation assays.

As determined by this co-immunoprecipitation assay, pro-caspase-1 self-associated and this was enhanced by co-expression of RIP2. However, when COP-1 was also co-expressed, this RIP2-mediated effect on pro-caspase-1 self-association was negated. These findings suggested the possibility of a competitive mechanism, in which COP-1 competes with RIP2 for binding to pro-caspase-1. To test this hypothesis, therefore, transfection experiments were preformed in which FLAG™-RIP2 and Myc-tagged pro-caspase-1 (C285A mutant) were expressed in 293T cells in the presence of increasing amounts of HA-tagged COP-1. The effects of COP-1 on association of RIP2 with pro-caspase-1 were then evaluated by co-immunoprecipitation assays in which immunoprecipitations were performed using anti-FLAG™ antibody to recover FLAG™-RIP2 protein and the resulting immune-complexes were analyzed by SDS-PAGE/immunoblotting using anti-Myc antibody to detect associated Myc-pro-caspase-1.

The results from these experiments indicated that COP-1 inhibited association of pro-caspase-1 with RIP2 in a dose-dependent manner. Immunoblot analysis of lysates from these same cells demonstrated that COP-1 did not affect the total levels of pro-caspase-1 or RIP2, but rather just their association. These results therefore confirm that COP-1 can interfere with binding of pro-caspase-1 to RIP2.

14.3 COP-1 inhibition of caspase-1-mediated activation of pro-IL-1β

Active caspase-1 cleaves pro-IL-1β, resulting in the generation of bioactive IL-1β which is secreted from cells. It was hypothesized that COP-1 could suppress caspase-1-induced pro-IL-1β processing and thus reduce secretion of IL-1β.

To test this hypothesis, COS-7, 293T, or 293HEK cells were co-transfected in 12 well (22 mm in diameter) plates using Lipofectamine™ Plus Reagent (GIBCO BRL, Grand Island, N.Y.) with plasmids encoding mouse pro-IL-1β, human caspase-1, RIP2, or COP-1, in various amounts (total DNA=2.0 μg). At 1 day after transfection, supernatants were collected and stored at −80° C. or used immediately to quantify secretion of mature murine IL-1β into the culture medium by an ELISA assay, according to the manufacturer's protocol (R&D systems, Minneapolis, Minn.).

Figure 6:
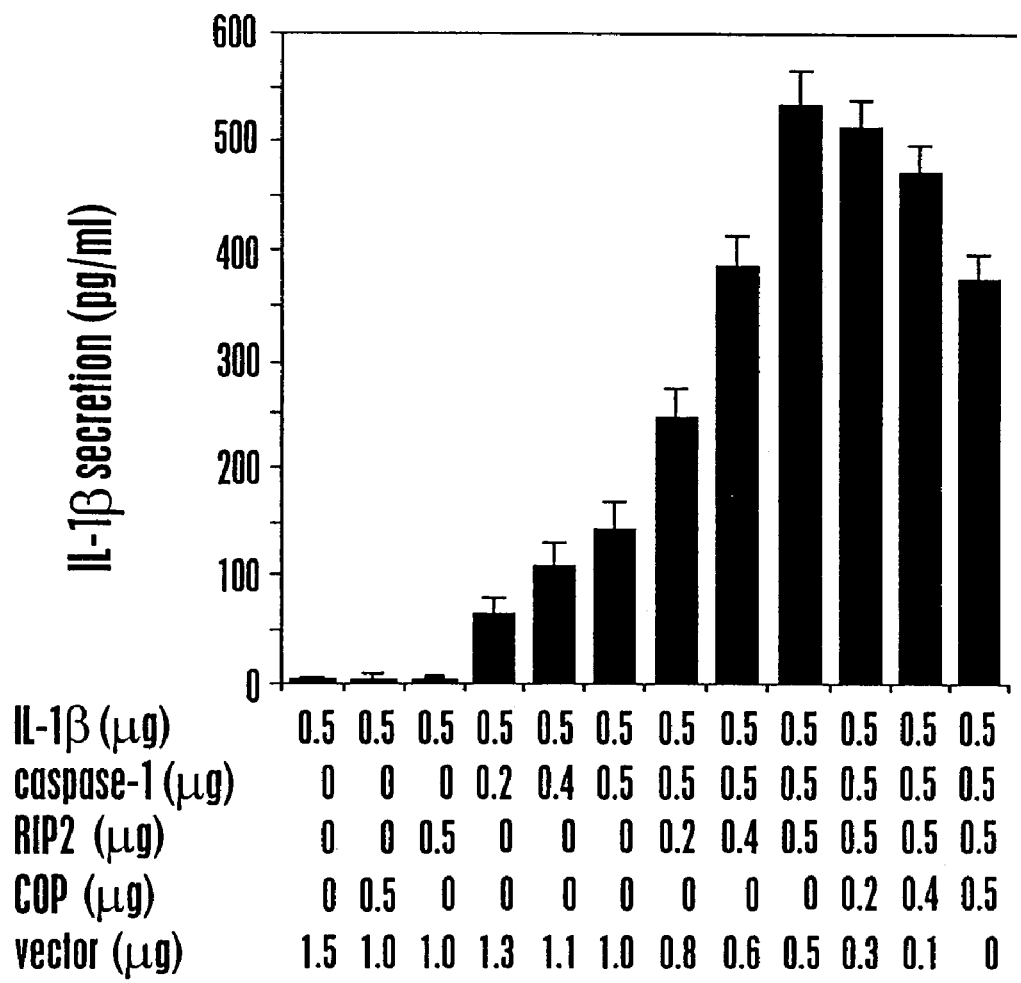
FIG. 6 shows IL-1β secretion by COS7 cells transfected with the indicated amounts of expression vectors encoding the indicated proteins.

Co-expression of pro-caspase-1 and pro-IL-1β in COS-7 cells resulted in secretion of mature IL-1β ranging from 80 pg/ml to 250 pg/ml, which was proportional to the amount of pro-caspase-1 plasmid used (FIG. 17). This IL-1β secretion was enhanced by co-expression of RIP2 plasmid. In contrast, expression of COP-1 together with pro-caspase-1, pro-IL-1β, and RIP2 resulted in a dose-dependent decrease in the amount of mature IL-1β secretion, proportional to the amount of COP-1-encoding plasmid used (FIG. 6). Similar results were obtained using 293T or 293HEK cells. These results indicate that COP-1 is capable of suppressing the caspase-1-mediated secretion of IL-1β.

15.0 Identification of COP-2

A human CARD-containing proteins, designated COP-2, for CARD-only protein 2, was identified and the gene and cDNA cloned. The predicted protein of COP-2 has high sequence similarity to the CARD-domain of human caspase-1. For COP-2, two primers based on the caspase-15 genomic sequence were designed, one in the middle of the CARD domain (5'-aagaagagacggctgcttatcaat-3'; SEQ ID NO:104) and the other in the catalytic domain (5'-ccacagcaggcctcgaagatgatc-3'; SEQ ID NO:105). RT-RTR was performed, and a single band was observed, although the band size was smaller than expected for caspase-15. The PCR product was sequenced, and it was found that two exons were deleted and the catalytic domain was directly connected to the CARD domain. However, due to a frameshift, a stop codon occurs just after the CARD domain, resulting in truncated protein and no translation of the catalytic domain.

To clone the N-terminal region, a primer (5'-atgatcctcct-gaagaagag-3'; SEQ ID NO:106) was designed with the genomic sequence in the most N-terminal portion of the CARD domain including ATG. RT-PCR was performed, and the PCR product was sequenced and found to be the same as in the genomic DNA. A merged construct containing both the N-terminal fragment and the CARD domain sequence was made by PCR.

The COP-2 cDNA sequence identified contained 321 nucleotides (SEQ ID NO:89), and the deduced amino acid sequence (SEQ ID NO:90) had a high level of identity with caspase-1. An alignment of COP-2 (SEQ ID NO:90) and caspase-1 (SEQ ID NO:87) is shown in FIG. 5, with the consensus sequence (SEQ ID NO:91) shown above the aligned sequences. The amino acids shaded in black are identical. The stipled shading represents a match within 3 distance units. COP-2 is encoded by the caspase-15 gene (FIG. 3), but COP-2 is a CARD only protein that lacks the caspase catalytic domain.

COP-2 cDNA encodes a polypeptide with downstream termination codons, which result in shorter proteins containing a CARD domain without associated catalytic protease domains. COP-2 is therefore expected to function as transdominant inhibitor that likely prevents caspase activation by binding to the CARD-domains (pro-domains) in pro-enzymes such as pro-caspase-1.

COP-2 polypeptide is expected to function as A regulator of caspase-1 activation by enhancing or suppressing the activation of caspase-1. COP-2 binding activity is tested, for example, by making epitope tagged fusions with COP-2 and caspase-1 and co-immunoprecipitating to determine binding interactions with caspase-1. Antibodies specific for COP-2 are also made.

The effect of COP-2 on caspase-1 proteolytic activity is also tested. Methods for measuring caspase activity are well known (see, for example, Thornberry, *Nature* 356:768-774 (1992); Thornberry and Molineaux, *Protein Science* 4:3-12 (1995); Rano et al., *Chem. Biol.* 4:149-155 (1997); Fletcher et al., *J. Interferon Cytokine Res.* 15:243-248 (1995)), and are also described above.

Although the invention has been described with reference to the examples above, it should be understood that various modifications can be made without departing from the spirit of the invention.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

We claim:

1. An isolated CARD-containing polypeptide consisting of the amino acid sequence of SEQ ID NO:97.

2. A composition comprising the polypeptide of claim 1 and a pharmaceutically acceptable carrier.

3. An isolated polypeptide comprising an NB-ARC domain, said polypeptide consisting of SEQ ID NO:180.

4. A composition comprising the polypeptide of claim 3 and a pharmaceutically acceptable carrier.

* * * * *